(12) United States Patent
Koyuncu et al.

(10) Patent No.: US 12,138,243 B2
(45) Date of Patent: *Nov. 12, 2024

(54) ANTIVIRAL USE OF FABP4 MODULATING COMPOUNDS

(71) Applicant: CRESCENTA BIOSCIENCES, Union, NJ (US)

(72) Inventors: Emre Koyuncu, Irvine, CA (US); Hahn Kim, Princeton, NJ (US); Gokhan Hotamisligil, Weston, MA (US)

(73) Assignee: CRESCENTA BIOSCIENCES, Union, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/566,695

(22) Filed: Dec. 31, 2021

(65) Prior Publication Data

US 2023/0241025 A1    Aug. 3, 2023

(51) Int. Cl.
*A61K 31/404* (2006.01)
*A61K 45/06* (2006.01)
*A61P 31/12* (2006.01)

(52) U.S. Cl.
CPC ............ *A61K 31/404* (2013.01); *A61K 45/06* (2013.01); *A61P 31/12* (2018.01)

(58) Field of Classification Search
CPC ........ A61K 31/404; A61K 45/06; A61P 31/12
See application file for complete search history.

(56) References Cited

U.S. PATENT DOCUMENTS 3,542,785 A    11/1970   William et al.
3,555,034 A    1/1971    Diebold et al.
(Continued)

FOREIGN PATENT DOCUMENTS

DE    2431292 A1    1/1976
EP    0307077 A1    3/1989
(Continued)

OTHER PUBLICATIONS

Conrad, Marker of immune activation in COVID-19, retrieved from https://medicine.osu.edu/news/marker-of-immune-activation-in-covid-19, Feb. 1, 2021 (Year: 2021).*

(Continued)

*Primary Examiner* — Kortney L. Klinkel
*Assistant Examiner* — Padmaja S Rao
(74) *Attorney, Agent, or Firm* — Gearhart Law, LLC

(57) ABSTRACT

A method for treating a viral disease in a subject comprising administering to said subject a therapeutically effective dose of one or more compounds that bind to fatty acid binding protein FABP4, with compounds described in the specification some having the general formula, Formula I-Formula XII, where $W_1$-$W_4$, $Z_1$-$Z_4$, $Z_1$-$Z_5$, X, Y, n, and $R_1$-$R_5$ are as defined in the claims and description of embodiments. In examples, the ring Z contains $Z_1$-$Z_4$. In other examples, the ring Z contains $Z_1$-$Z_5$.

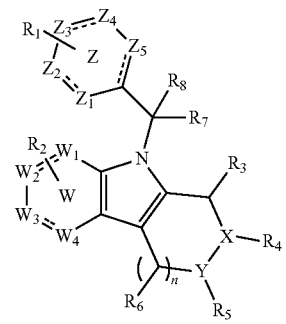

50 Claims, 2 Drawing Sheets

(56) References Cited

U.S. PATENT DOCUMENTS

| | | | |
|---|---|---|---|
| 3,668,207 | A | 6/1972 | William et al. |
| 4,009,181 | A | 2/1977 | Berger et al. |
| 4,775,680 | A | 10/1988 | Gillard et al. |
| 5,492,915 | A | 2/1996 | Dereu et al. |
| 5,522,385 | A | 6/1996 | Lloyd et al. |
| 5,541,196 | A | 7/1996 | Fournet et al. |
| 5,755,218 | A | 5/1998 | Johansson et al. |
| 5,819,726 | A | 10/1998 | Rubsamen et al. |
| 5,855,913 | A | 1/1999 | Hanes et al. |
| 5,906,202 | A | 5/1999 | Schuster et al. |
| 5,957,124 | A | 9/1999 | Lloyd et al. |
| 5,971,951 | A | 10/1999 | Ruskewicz |
| 5,985,309 | A | 11/1999 | Edwards et al. |
| 5,985,320 | A | 11/1999 | Edwards et al. |
| 6,098,620 | A | 8/2000 | Lloyd et al. |
| 6,138,668 | A | 10/2000 | Patton et al. |
| 6,167,880 | B1 | 1/2001 | Gonda et al. |
| 6,228,383 | B1 | 5/2001 | Hansen et al. |
| 6,303,582 | B1 | 10/2001 | Eljamal et al. |
| 6,349,719 | B2 | 2/2002 | Gonda |
| 6,387,390 | B1 | 5/2002 | Deaver et al. |
| 6,408,854 | B1 | 6/2002 | Gonda et al. |
| 6,423,344 | B1 | 7/2002 | Platz et al. |
| 6,427,682 | B1 | 8/2002 | Klimowicz et al. |
| 6,431,167 | B1 | 8/2002 | Gonda et al. |
| 6,447,753 | B2 | 9/2002 | Edwards et al. |
| 6,467,476 | B1 | 10/2002 | Ivri et al. |
| 6,503,480 | B1 | 1/2003 | Edwards et al. |
| 6,509,006 | B1 | 1/2003 | Platz et al. |
| 6,540,153 | B1 | 4/2003 | Ivri |
| 6,540,154 | B1 | 4/2003 | Ivri et al. |
| 6,543,443 | B1 | 4/2003 | Klimowicz et al. |
| 6,543,448 | B1 | 4/2003 | Smith et al. |
| 6,546,927 | B2 | 4/2003 | Litherland et al. |
| 6,546,929 | B2 | 4/2003 | Burr et al. |
| 6,550,472 | B2 | 4/2003 | Litherland et al. |
| 7,160,909 | B2 | 1/2007 | Kinnick et al. |
| 7,160,990 | B2 | 1/2007 | Guss et al. |
| 10,207,995 | B2 | 2/2019 | Slomczynska et al. |
| 2005/0009817 | A1 | 1/2005 | Savoy et al. |
| 2005/0026988 | A1 | 2/2005 | Kinnick et al. |
| 2010/0056377 | A1 | 3/2010 | Nagasawa et al. |
| 2011/0077250 | A1 | 3/2011 | Ryder |
| 2012/0122837 | A1 | 5/2012 | Cheng et al. |
| 2012/0134998 | A1 | 5/2012 | Hotamisligil et al. |
| 2013/0116231 | A1 | 5/2013 | Wilson et al. |
| 2013/0116234 | A1 | 5/2013 | Ceccarelli et al. |
| 2013/0261099 | A1 | 10/2013 | Branchaud et al. |
| 2014/0057900 | A1 | 2/2014 | McKnight et al. |
| 2015/0038530 | A1 | 2/2015 | Abraham et al. |
| 2015/0057326 | A1 | 2/2015 | Wu |
| 2016/0113937 | A1 | 4/2016 | Wan et al. |
| 2016/0346186 | A1 | 12/2016 | Cotsarels et al. |
| 2017/0216241 | A1 | 8/2017 | Ojima et al. |
| 2018/0105586 | A1 | 4/2018 | Hotamisligil et al. |

FOREIGN PATENT DOCUMENTS

| | | |
|---|---|---|
| JP | 2007302578 A | 11/2007 |
| WO | 1996015111 A1 | 5/1996 |
| WO | 00/15229 A1 | 3/2000 |
| WO | 00/15230 A1 | 3/2000 |
| WO | 00/47734 A1 | 8/2000 |
| WO | 00/59506 A1 | 10/2000 |
| WO | 2001/54694 A1 | 8/2001 |
| WO | 2002/40448 A1 | 5/2002 |
| WO | 2002044152 A1 | 6/2002 |
| WO | 2004063156 A1 | 7/2004 |
| WO | 2005072408 A2 | 8/2005 |
| WO | 2008061671 A2 | 5/2008 |
| WO | 2010056631 A1 | 5/2010 |
| WO | 2012006612 A3 | 5/2012 |
| WO | 2012/139028 A2 | 10/2012 |
| WO | 2013/062344 A1 | 5/2013 |
| WO | 2013189841 A1 | 12/2013 |
| WO | 2014029723 A1 | 2/2014 |
| WO | 2014040938 A1 | 3/2014 |
| WO | 2014093552 A1 | 6/2014 |
| WO | 2014146994 A1 | 9/2014 |
| WO | 2014177593 A1 | 11/2014 |
| WO | 2014/201327 A1 | 12/2014 |
| WO | 2014201326 A1 | 12/2014 |
| WO | 2016040222 A1 | 3/2016 |
| WO | 2016061642 A1 | 4/2016 |
| WO | 2016064683 A1 | 4/2016 |
| WO | 2017023905 A1 | 2/2017 |
| WO | 2017034986 A1 | 3/2017 |
| WO | 2017191599 A1 | 11/2017 |
| WO | 2017198756 A1 | 11/2017 |
| WO | 2018078624 A1 | 5/2018 |
| WO | 2018231772 A1 | 12/2018 |
| WO | 2019018785 A2 | 1/2019 |
| WO | 2021263246 A1 | 12/2021 |
| WO | 2022010948 A1 | 1/2022 |
| WO | 2022040604 A1 | 2/2022 |

OTHER PUBLICATIONS

Sokolowska et al., Effects of non-steroidal anti-inflammatory drugs and other eicosanoid pathway modifiers on antiviral and allergic responses. EAACI task force on eicosanoids consensus report in times of COVID-19, Preprint posted on Authorea, 1-28, Nov. 26, 2021 (Year: 2021).*

Masato Furuhashi, et al., Reduction of circulating FABP4 level by treatment with omega-3 fatty acid ethyl esters, Lipids in Health and Disease, 2016, pp. 1-9, 15(5).

Yan Li, et al., Concerted Dynamic Motions of an FABP4 Model and Its Ligands Revealed by Microsecond Molecular Dynamics Simulations, Biochemistry, 2014, pp. 6409-6417, 53.

Heying Pei, et al., Therapeutic potential of a synthetic FABP4 inhibitor 8g on atherosclerosis in ApoE-deficient mice: the inhibition of lipid accumulation and inflammation, RSC Adv., 2016, pp. 52518-52527, 6.

Min Shi, et al., Pharmacological inhibition of fatty acid-binding protein 4 (FABP4) protects against renal ischemia-reperfusion injury, RSC Adv., 2018, pp. 15207-15214, 8.

Yan Wang, et al., Discovery of FDA-Approved Drugs as Inhibitors of Fatty Acid Binding Protein 4 Using Molecular Docking Screening, Journal of Chemical Information and Modeling, 2014, pp. 3046-3050, 54.

Wanhua Lin, et al., BMS309403 Stimulates Glucose Uptake in Myotubes through Activation of AMP-Activated Protein Kinase, PLOS ONE, 2012, pp. 1-8, 7(8).

Holger Kuehne, et al., Design and synthesis of selective, dual fatty acid binding protein 4 and 5 inhibitors, Bioorganic & Medicinal Chemistry Letters, 2016, pp. 5092-5097, 26.

Ge Liu, et al., The natural compound GL22, isolated from Ganoderma mushrooms, suppresses tumor growth by altering lipid metabolism and triggering cell death, Cell Death and Disease, 2018, pp. 1-14.

Sergio Oddi, et al., The anti-inflammatory agent bindarit acts as a modulator of fatty acid-binding protein 4 in human monocytic cells, Scientific Reports, 2019, pp. 1-11.

Mika Hirose, et al., Structure of the human-heart fatty-acid-binding protein 3 in complex with the fluorescent probe 1-anilinonaphthalene-8-sulphonic acid, Journal of Synchrotron Radiation, 2013, pp. 923-928, 20.

Yan Wang, et al., Pimozide, a Novel Fatty Acid Binding Protein 4 Inhibitor, Promotes Adipogenesis of 3T3-L1 Cells by Activating PPARγ, ACS Chemical Neuroscience, 2015, pp. 211-218, 6.

Qinyuan Xu, et al., Design, synthesis and biological evaluation of thiazole- and indole-based derivatives for the treatment of type II diabetes, European Journal of Medicinal Chemistry, 2012, pp. 70-81, 52.

Hisanorj Uehara, et al., Exogenous fatty acid binding protein 4 promotes human prostate cancer cell progression, International Journal of Cancer, 2014, pp. 2558-2568, 135.

Mary Y.K. Lee, et al., Chronic administration of BMS309403 improves endothelial function in apolipoprotein E-deficient mice

(56) References Cited

OTHER PUBLICATIONS and in cultured human endothelial cells, British Journal of Pharmacology, 2011, pp. 1564-1576, 162.
Maria J. P. Van Dongen, et al., Structure-Based Screening as Applied to Human FABP4: A Highly Efficient Alternative to HTS for Hit Generation, J. Am. Chem. Soc., 2002, pp. 11874-11880, 124(40).
Ann V. Hertzel, et al., Identification and Characterization of a Small Molecule Inhibitor of Fatty Acid Binding Proteins, Journal of Medicinal Chemistry, 2009, pp. 6024-6031, 52.
William T. Berger, et al., Targeting Fatty Acid Binding Protein (FABP) Anandamide Transporters—A Novel Strategy for Development of Anti-Inflammatory and Anti-Nociceptive Drugs, PLOS ONE, 2012, pp. 1-12, 7(12).
Kantaro Nishigori, et al., Development of a Radioiodinated Triazolopyrimidine Probe for Nuclear Medical Imaging of Fatty Acid Binding Protein 4, PLOS ONE, 2014, pp. 1-10, 9(4).
P. Mosinska, et al., FABP4 blocker attenuates colonic hypomotility and modulates white adipose tissue-derived hormone levels in mouse models mimicking constipation-predominant IBS, Neurogastroenterol Motil, 2018, pp. 1-13, 30(5).
S. M. Berge, et al., Pharmaceutical salts, J. Pharm. Sci., 1977, pp. 1-19, 66(1).
Philip L. Gould, Salt selection for basic drugs, International Journal of Pharmaceutics, 1986, pp. 201-217, 33(1-3).
Mino R. Caira, et al., Preparation and crystal characterization of a polymorph, a monohydrate, and an ethyl acetate solvate of the antifungal fluconazole, Journal of Pharmaceutical Sciences, 2004, pp. 601-611, 93(3).
Elsa C. Van Tonder, et al., Preparation and physicochemical characterization of 5 niclosamide solvates and 1 hemisolvate, AAPS PharmSciTech, 2004, pp. 1-10, 5(1).
Ann Bingham, et al., delta-Sulfanilamide, Acta Crystallographica Section C Crystal Structure Communications, 2008, pp. 205-207, C64.
Hans Bundgaard, Design of Prodrugs, 1985, Oxford : Elsevier, Amsterdam; New York.
V. Stella, Pro-drugs: An Overview and Definition, ACS Symposium Series, vol. 14, 1975, pp. 1-115, Chapter 1.
Giorgio Bertolini, et al., A New Rational Hypothesis for the Pharmacophore of the Active Metabolite of Leflunomide, a Potent Immunosuppressive Drug, J. Med. Chem., 1997, pp. 2011-2016, 40(13).
D. Shan, et al., Prodrug strategies based on intramolecular cyclization reactions, J. Pharm. Sci, 1997, pp. 765-767, 86(7).
Kenneth D. Bagshawe, Antibody-directed enzyme prodrug therapy: A review, Drug Development Research, 1995, pp. 220-230, 34(2).
Thorsteinn Loftsson, et al., The pharmacokinetics and transdermal delivery of loteprednol etabonate and related soft steroids, Advanced Drug Delivery Reviews, 1994, pp. 293-299, 14(2-3).
R. Ferroni, et al., Cyclic guanidines: synthesis and antiplatelet activity of 4,6,7,8-tetrahydro-1H-imidazo[1,2-a] pyrazolo[3,4-d]pyrimidin-7-ones and 1,4,6,7,8,9-hexahydropyrazolo[3',4':4,5]pyrimido[2,1-c] [1,2,4]triazin-7-ones, Arzneimittelforschung, 1990, pp. 1328-1331, 40(12).
T. Iwaoka, et al., Determination of (+)- and (−)-nicardipine concentrations in human serum and their correlation with the antihypertensive effect after oral administration of racemic nicardipine, European Journal of Clinical Pharmacology, 1995, pp. 345-349, 48.
C. H. Lochmueller, et al., Chromatographic resolution of enantiomers selective review, J. Chromatogr., 1975, pp. 283-302, 113(3).
Peyton Jacob III, Resolution of (+/−)-5-bromonornicotine. Synthesis of (R)- and (S)-nornicotine of high enantiomeric purity, J. Org. Chem., 1982, pp. 4165-4167, 47(21).
Antoine Fakhry Abdelmassih, et al., Single cell sequencing unraveling genetic basis of severe COVID19 in obesity, Obes. Med., 2020, 20:100303.
Srinivasa Reddy Bonam, et al., Adjunct Immunotherapies for the Management of Severely Ill COVID-19 Patients, Cell Reports Medicine, 2020, 100016, 1(2).

Pierre Bost, et al., Host-Viral Infection Maps Reveal Signatures of Severe COVID-19 Patients, Cell, 2020, pp. 1475-1488, 181(7).
Blai Coll, et al., The fatty acid binding protein-4 (FABP4) is a strong biomarker of metabolic syndrome and lipodystrophy in HIV-infected patients, Atherosclerosis, 2008, pp. 147-153, 199(1).
Christophe Desterke, et al., PPARγ Cistrome Repression during Activation of Lung Monocyte-Macrophages in Severe COVID-19, iScience, 2020, p. 101611, 23(10).
Prashant Dogra, et al., Innate Immunity Plays a Key Role in Controlling Viral Load in COVID-19: Mechanistic Insights from a Whole-Body Infection Dynamics Model, ACS Pharmacol. Transl. Sci., 2021, pp. 248-265, 4(1).
Marat Fudim, et al., Implications for Neuromodulation Therapy to Control Inflammation and Related Organ Dysfunction in COVID-19, Journal of Cardiovascular Translational Research, 2020, pp. 894-899, 13.
Luis F> Garcia, Immune Response, Inflammation, and the Clinical Spectrum of COVID-19, Front. Immunol., 2020, pp. 1-13, vol. 11, Art. 1441.
Anne Geller, et al., Could the Induction of Trained Immunity by β-Glucan Serve as a Defense Against COVID-19?, Front. Immunol., 2020, pp. 1-11, vol. 11, Art. 1782.
Lara Gibellini, et al., Different origin of adipogenic stem cells influences the response to antiretroviral drugs, Experimental Cell Research, 2015, pp. 160-169, 337(2).
Lisa Giovannini-Chami, et al., The 'one airway, one disease' concept in light of Th2 inflammation, Eur. Respir. J., 2018, pp. 1-12, vol. 52, Art. 1800437.
Jean-Baptiste Gorin, et al., Plasma FABP4 is associated with liver disease recovery during treatment-induced clearance of chronic HCV infection, Sci. Rep., 2020, pp. 1-10, vol. 10, Art. 2081.
Monika Bociaga-Jasik, et al., Metabolic complications and selected cytokines in HIV-infected individuals, Polskie Archiwum Medycyny Wewnetrznej, 2014, pp. 26-35, 124 (1-2).
Rogan A. Grant, et al., Alveolitis in severe SARS-CoV-2 pneumonia is driven by self-sustaining circuits between infected alveolar macrophages and T cells, bioRXiv, 2020, pp. 1-33.
Masha Hajivalili, et al., Gaining insights on immune responses to the novel coronavirus, COVID-19 and therapeutic challenges, Life Sci., 2020, pp. 1-12, vol. 257.
Aaron W. James, et al., Lentiviral Delivery of PPARγ shRNA Alters the Balance of Osteogenesis and Adipogenesis, Improving Bone Microarchitecture, Tissue Eng. Part A., 2014, pp. 2699-2710, 20(19-20).
Yan Jiang, et al., Exploring the mechanism of Shengmai Yin for coronary heart disease based on systematic pharmacology and chemoinformatics, Bioscience Reports, 2020, pp. 1-24, 40(6).
Yong-Jiu Jin, et al., Identification of a Novel Binding Site Between HIV Type 1 Nef C-Terminal Flexible Loop and AP2 Required for Nef-Mediated CD4 Downregulation, AIDS Res. Hum. Retroviruses, 2013, pp. 725-731, 29(4).
Ashley L. St. John, et al., Early insights into immune responses during COVID-19, J. Immunol., 2020, pp. 555-564, 205.
Leila Mohamed Khosroshahi, et al., Dysregulation of the immune response in coronavirus disease 2019, Cell Biology International, 2020, pp. 1-6.
Anna Klinke, et al., Emerging therapies for right ventricular dysfunction and failure, Cardiovasc. Diagn. Ther., 2020, pp. 1735-1767, 10(5).
Minfeng Liao, et al., The landscape of lung bronchoalveolar immune cells in COVID-19 revealed by single-cell RNA sequencing, Nature Medicine, 2020, pp. 842-844, 26.
Zhongshun Liu, et al., Histone Deacetylase Inhibitor SAHA Induces Expression of Fatty Acid-Binding Protein 4 and Inhibits Replication of Human Cytomegalovirus, Virol. Sin., 2021, pp. 1352-1362, 36(6).
Yu Liu, et al., The roles of PPARγ and its agonists in autoimmune diseases: A comprehensive review, J. Autoimmun., 2020, pp. 1-12.
Jinglu Lyu, et al., Reflection on lower rates of COVID-19 in children: Does childhood immunizations offer unexpected protection?, Med. Hypotheses, 2020, 143.
Lucy MacDonald, et al., COVID-19 and Rheumatoid Arthritis share myeloid pathogenic and resolving pathways, bioRxiv, pp. 1-29.

(56) References Cited

OTHER PUBLICATIONS

L. Lamara Mahammed, et al., Immunopathological mechanisms in SARS-CoV-2 infection, ASJP, 2019, pp. 2453-3555, 5(1).
Patrick W. G. Mallon, et al., Effect of Rosiglitazone on Peroxisome Proliferator-Activated Receptor γ Gene Expression in Human Adipose Tissue Is Limited by Antiretroviral Drug-Induced Mitochondrial Dysfunction, The Journal of Infectious Diseases, 2008, pp. 1794-1803, 198(12).
Roberta Goncalves Marangoni, et al., Adipocytic Progenitor Cells Give Rise to Pathogenic Myofibroblasts: Adipocyte-to-Mesenchymal Transition and Its Emerging Role in Fibrosis in Multiple Organs, Current Rheumatology Reports, 2020, pp. 1-8, 22:79.
Pierre S. Maximus, et al., Adipocytokines: Are they the Theory of Everything?, Cytokine, 2020, pp. 1-11.
Mario Luca Morieri, et al., Adipokines levels in HIV infected patients: lipocalin-2 and fatty acid binding protein-4 as possible markers of HIV and antiretroviral therapy-related adipose tissue inflammation, BMC Infect. Dis., 2018, pp. 1-9, 18:10.
Leo Nicolai, et al., Vascular neutrophilic inflammation and immunothrombosis distinguish severe COVID-19 from influenza pneumonia, J. Thromb. Haemost., 2020, pp. 1-8.
Youdong Pan, et al., Survival of tissue-resident memory T cells requires exogenous lipid uptake and metabolism, Nature, 2017, pp. 252-256, 543(7644).
Gaetano Zirro, et al., Imperfect storm: is interleukin-33 the Achilles heel of COVID-19?, Lancet. Rheumatol, 2020, pp. e779-e790, 2(12).
Ivon Johanna Rodriguez, et al., Human immune response to SARS-CoV-2: What is known? A scoping review, Infectio, 2020, pp. 26-35, 24(3).
Constance E. Runyan, et al., Impaired phagocytic function in CX3CR1+ tissue-resident skeletal muscle macrophages prevents muscle recovery after influenza A virus-induced pneumonia in old mice, Aging Cell, 2020, pp. 1-20, 19.
Hibah Shaath, et al., Single-Cell Transcriptome Analysis Highlights a Role for Neutrophils and Inflammatory Macrophages in the Pathogenesis of Severe COVID-19, Cells, 2020, pp. 1-19, 9, 2374.
Dylan Sheerin, et al., Systematic evaluation of transcriptomic disease risk and diagnostic biomarker overlap between COVID-19 and tuberculosis: a patient-level meta-analysis, medRxiv, 2020, pp. 1-26.
Rajnish Kumar Singh, et al., HIF1α-Regulated Expression of the Fatty Acid Binding Protein Family Is Important for Hypoxic Reactivation of Kaposi's Sarcoma-Associated Herpesvirus, J. Virol., 2021, pp. e02063-20, 95(12).
Johan Smith, et al., An overview of acute lung injury in general and in particular viral infections with specific reference to nebulized surfactant and anticoagulation, Journal of Respiratory Diseases and Medicine, 2020, pp. 1-27, 2.
Chiao-Fang Teng, et al., A biphasic response pattern of lipid metabolomics in the stage progression of hepatitis B virus X tumorigenesis, Molecular Carcinogenesis, 2016, pp. 105-114, 55(1).
Prasad Tongaonkar, et al., RTD-1 therapeutically normalizes synovial gene signatures in rat autoimmune arthritis and suppresses proinflammatory mediators in RA synovial fibroblasts, Physiol. Genomics, 2019, pp. 657-667, 51(12).
Miguel A. Vega, et al., MAFB and MAF Transcription Factors as Macrophage Checkpoints for COVID-19 Severity, Front. Immunol., 2020, pp. 1-9, 11.
Li Wang, et al., Novel gene-specific translation mechanism of dysregulated, chronic inflammation reveals promising, multifaceted COVID-19 therapeutics, bioRxiv, 2020, pp. 1-36.
Jun Wu, et al., Immunity-and-matrix-regulatory cells derived from human embryonic stem cells safely and effectively treat mouse lung injury and fibrosis, Cell Research, 2020, pp. 794-809, 30.
Gang Xu, et al., The differential immune responses to COVID-19 in peripheral and lung revealed by single-cell RNA sequencing, Cell Discovery, 2020, pp. 1-14, 6:73.
Dan Zhang, et al., COVID-19 infection induces readily detectable morphologic and inflammation-related phenotypic changes in peripheral blood monocytes, J. Leukoc. Biol., 2020, pp. 1-10.
Ji-Yuan Zhang, et al., Single-cell landscape of immunological responses in patients with COVID-19, Nature Immunology, 2020, pp. 1107-1118, 21.
Bin Zhang, et al., CD127 imprints functional heterogeneity to diversify monocyte responses in human inflammatory diseases, bioRxiv, 2020, pp. 1-34.
Yuanqi Gong, et al., FABP4 inhibitors suppress inflammation and oxidative stress in murine and cell models of acute lung injury, Biochemical and Biophysical Research Communications, 2018, pp. 1115-1121, 496.
Yooju Jung, et al., Functional inhibition of fatty acid binding protein 4 ameliorates impaired ciliogenesis in GCs, Biochemical and Biophysical Research Communications, 2021, pp. 28-33, 539.
Tjeerd Barf, et al., N-Benzyl-indolo carboxylic acids: Design and synthesis of potent and selective adipocyte fatty-acid binding protein (A-FABP) inhibitors, Bioorganic & Medicinal Chemistry Letters, 2009, pp. 1745-1748, 19.
Rune Ringom, et al., Substituted benzylamino-6-(trifluoromethyl)pyrimidin-4(1H)-ones: a novel class of selective human A-FABP inhibitors, Bioorganic & Medicinal Chemistry Letters, 2004, pp. 4449-4452, 14.
Fredik Lehmann, et al., Discovery of inhibitors of human adipocyte fatty acid-binding protein, a potential type 2 diabetes target, Bioorganic & Medicinal Chemistry Letters, 2004, pp. 4445-4448, 14.
Haiyan Cai, et al., Discovery of highly selective inhibitors of human fatty acid binding protein 4 (FABP4) by virtual screening, Bioorganic & Medicinal Chemistry Letters, 2010, pp. 3675-3679, 20.
Masato Furuhashi, et al., Fatty acid-binding proteins: role in metabolic diseases and potential as drug targets, Nature Reviews Drug Discovery, 2008, pp. 489-503, 7.
Xiujie Liu, et al., New aromatic substituted pyrazoles as selective inhibitors of human adipocyte fatty acid-binding protein, Bioorganic & Medicinal Chemistry Letters, 2011, pp. 2949-2952, 21.
Yoko Beniyama, et al., Structure-guided design, synthesis and in vitro evaluation of a series of pyrazole-based fatty acid binding protein (FABP) 3 ligands, Bioorganic & Medicinal Chemistry Letters, 2013, pp. 1662-1666, 23.
An Cheng, et al., Development of FABP3 ligands that inhibit arachidonic acid-induced α-synuclein oligomerization, Brain Research, 2019, pp. 190-197.
Holger Kuehne, et al., Design and synthesis of selective, dual fatty acid binding protein 4 and 5 inhibitors, Bioorganic & Medicinal Chemistry Letters, 2016, pp. 5092-5097, 26(20).
Kazuya Matsuo, et al., Inhibition of MPTP-induced α-synuclein oligomerization by fatty acid binding protein 3 ligand in MPTP-treated mice, Neuropharmacology, 2019, pp. 164-174.
Haiyan Cai, et al., Novel fatty acid binding protein 4 (FABP4) inhibitors: Virtual screening, synthesis and crystal structure determination, European Journal of Medicinal Chemistry, 2015, pp. 241-250, 90.
Yang Zhou, et al., The discovery of novel and selective fatty acid binding protein 4 inhibitors by virtual screening and biological evaluation, Bioorganic & Medicinal Chemistry, 2016, pp. 4310-4317, 24.
Alba Bosquet, et al., FABP4 inhibitor BMS309403 decreases saturated-fatty-acid-induced endoplasmic reticulum stress-associated inflammation in skeletal muscle by reducing p38 MAPK activation, BBA—Molecular and Cell Biology of Lipids, 2018, pp. 604-613, 1863.
Yuta Okamura, et al., Vasculo-protective effect of BMS-309403 is independent of its specific inhibition of fatty acid-binding protein 4, Pflugers Arch—Eur. J. Physiol., 2017, pp. 1-12.
Toshihiko Okada, et al., Synthesis of BMS-309403-Related Compounds, Including [14C]BMS-309403, a Radioligand for Adipocyte Fatty Acid Binding Protein, Chem. Pharm. Bull, 2012, pp. 164-168, 60(1).
Hong Lan, et al., Small-molecule inhibitors of FABP4/5 ameliorate dyslipidemia but not insulin resistance in mice with diet-induced obesity, Journal of Lipid Research, 2011, pp. 646-656, 52.

(56) References Cited

OTHER PUBLICATIONS

International Search Report and Written Opinion of the International Searching Authority dated Oct. 27, 2021 for PCT/US21/39740, pp. 1-17.
Masato Furuhashi, et al., Lipid Chaperones and Metabolic Inflammation, International Journal of Inflammation, 2011, pp. 1-13.
Ding-Ding Gao, et al., From hit to lead: Structure-based discovery of naphthalene-1-sulfonamide derivatives as potent and selective inhibitors of fatty acid binding protein 4, European Journal of Medicinal Chemistry, 2018, pp. 44-59, 154.
Giuseppe Floresta, et al., 3D-QSAR assisted identification of FABP4 inhibitors: An effective scaffold hopping analysis/QSAR evaluation, Bioorganic Chemistry, 2019, pp. 276-284, 84.
Giuseppe Floresta, et al., Adipocyte fatty acid binding protein 4 (FABP4) inhibitors. A comprehensive systematic review, European Journal of Medicinal Chemistry, 2017, pp. 854-873, 138.
Thereza Cristina Lonzetti Bargut, et al., Eicosapentaenoic acid (EPA) vs. Docosahexaenoic acid (DHA): Effects in epididymal white adipose tissue of mice fed a high-fructose diet, Prostaglandins, Leukotrienes and Essential Fatty Acids, 2017, pp. 14-24, 123.
Min Shi, et al., Pharmacological inhibition of fatty acid-binding protein 4 alleviated kidney inflammation and fibrosis in hyperuricemic nephropathy, European Journal of Pharmacology, 2020, pp. 1-9, 887.
Yu-Long He, et al., Development of FABP4/5 inhibitors with potential therapeutic effect on type 2 Diabetes Mellitus, European Journal of Medicinal Chemistry, 2021, pp. 1-14, 224.
Hao-Chi Hsu, et al., The Antinociceptive Agent SBFI-26 Binds to Anandamide Transporters FABP5 and FABP7 at Two Different Sites, Biochemistry, 2017, pp. 3454-3462, 56.
Ewgenij Proschak, et al., Opportunities and Challenges for Fatty Acid Mimetics in Drug Discovery, Journal of Medicinal Chemistry, 2017, pp. 5235-5266, 60.
Haixia Su, et al., Exploration of Fragment Binding Poses Leading to Efficient Discovery of Highly Potent and Orally Effective Inhibitors of FABP4 for Anti-inflammation, Journal of Medicinal Chemistry, 2020, pp. 4090-4106, 63(8).
Bernd Kuhn, et al., A Real-World Perspective on Molecular Design, Journal of Medicinal Chemistry, 2016, pp. 4087-4102, 59(9).
Uno Tagami, et al., Interaction Analysis of FABP4 Inhibitors by X-ray Crystallography and Fragment Molecular Orbital Analysis, ACS Med. Chem. Lett., 2016, pp. 435-439, 7(4).
Hai-Yan Cai, et al., Benzbromarone, an old uricosuric drug, inhibits human fatty acid binding protein 4 in vitro and lowers the blood glucose level in db/db mice, Acta Pharmacologica Sinica, 2013, pp. 1387-1402, 34.
A. W. Zimmerman, et al., New insights into the structure and function of fatty acid-binding proteins, Cell. Mol. Life Sci., 2002, pp. 1096-1116, 59.
Christiane Look, et al., BMS309403 directly suppresses cardiac contractile function, Naunyn-Schmiedeberg's Arch Pharmacol, 2011, pp. 255-263, 384.
Gordon S. Lee, et al., Fatty Acid Binding Proteins Expressed at theHuman Blood-Brain Barrier Bind Drugs in an Isoform-Specific Manner, Pharm. Res., 2015, pp. 3432-3446, 32.
A. L. Bingham et al., Chem. Commun., 603-604 (2001).
CAS Registry No. 116475-42-4, Sep. 25, 1988.
CAS Registry No. 2129127-97-3, Sep. 22, 2017.
CAS Registry No. 2440468-27-0, Jul. 3, 2020.
Lepre et al. "Theory and Applications of NMR-Based Screening in Pharmaceutical Research", Chem. Rev. 2004. vol. 104, pp. 3641-3675, especially: p. 3666, col. 2, para 3; p. 3669, col. 2, para 2.
Dutta et al. Int. J. Mol. Sci. 2019, 20, 644; Curbing Lipids: Impacts ON Cancer and Viral Infection (Year: 2019).
Dyall et al. Antimicrobial Agents and Chemotherapy, 2014, vol. 58 No. 8, p. 4885-4893 (Year: 2014).
Hotamisligil et al., Science. Nov. 22, 1996;274(5291):1377-9.
Hu and Qiao, Endocrine. Oct. 2011;40(2):196-202.
International Search report received for PCT Appl. No. PCT/US21/40588, mailed on Dec. 7, 2021, 6 pages.
Kay, David et al., Synthesis of 2-aminomethylene-1,2-dihydroimidazo[1, 2-a] quinolin-1-ones, Chemistry and Industry, 1988, pp. 94-95.
Kuhne et al., Bioorg Med Chem Lett. Oct. 15, 2016;26(20):5092-5097.
Lan et al., J Lipid Res. Apr. 2011;52(4):646-56.
Makowski et al., Nat Med. Jun. 2001 ; 7(6): 699-705.
Masanori Tayu et al., Org. Biomol. Chem. (2013) 11, 496.
Pubchem CID 110167588 (Year 2016).
PubChem CID 1264779 (2005).
Pubchem CID 15270263 (Year 2007).
Pubchem CID 2729601 (Year 2009).
PubChem CID 398603831 (2009).
PubChem CID 82577974 (2014).
PubChem CID 83835851 (2014).
Saksi et al., Circ Cardiovasc Genet. Oct. 2014;7(5):588-98.
Sanders et al. ,JAMA. 2020;323(18):1824-1836, doi: 10.1001/jama.2020.6019, published on line Apr. 13, 2020, (Year: 2020).
Sarangi et al. Diagnosis, prevention, and treatment of coronavirus disease: a review, Expert Review of Anti-infective Therapy, 2021, https://doi.org/10.1080/14787210.2021.1944103 (Year: 2021).
Schmidt P. et al., Heilmittelchemische Studien in der heterocyclischen Reihe. 22. Mitteilung. Pyrazolo-pyrimidine, Helvitica Chimica Acta, vol. 41, Issue4 1958 pp. 1052-1060.
Shaughnessy et al., Diabetes Jun. 2000; 49(6): 904-911.
Shum et al., J Clin Invest. Aug. 2006;116(8):2183-2192.
Mansoor et al. "2-ethylpyridine, a cigarette smoke component, causes mitochondrial damage in human retinal pigment epithelial cells in vitro", Indian J Ophthalmol. 2014. vol. 62(1 ), pp. 1622, especially: abstract; p. 2, para 3.
Sulsky et al., Bioorg Med Chem Lett. Jun. 15, 2007;17(12):3511-5.
Tagami et al., ACS Med Chem Lett. Apr. 14, 2016; 7(4): 435-439.
Tuncman et al., Proc Natl Acad Sci U S A. May 2, 2006;103(18):6970-5.
Wang et al., Oncotarget. Apr. 5, 2016;7(14):18984-98.
Yan et al., Placenta. Mar. 2016;39:94-100.
Zhu et al. "From SARS and MERS to CoVID-19: a brief summary and comparison of severe acute respiratory infections caused by three highly pathogenic human coronavirus," Respiratory Research, 2020 21 :224 https://doi.org/10.1186/s12931-020-01479-w (Year: 2020).
Barf et al. "N-Benzyl-indolo carboxylic acids: Design and synthesis of potent and selective adipocyte fatty-acid binding protein (A-FABP) inhibitors", Bioorganic & Medicinal Chemistry Letters. 2009. 19, pp. 1745-1748, especially: p. 1745, col. 1, para 2; p. 1747, Table 2, Compound 18.
Escote et al. "A study of fatty acid binding protein 4 in HIV-1 infection and in combination antiretroviral therapy-related metabolic disturbances and lipodystrophy", HIV Medicine, 2011, 12, pp. 428-437, especially: abstract.
Flynn et al. "Correlation and Prediction of Mass Transport across Membranes I: Influence of Alkyl Chain Length on Flux-Determining Properties of Barrier and Diffusant", Journal of Pharmaceutical Sciences. 1972. vol. 61, No. 6, pp. 838-852, especially: p. 843, col. 2, para 2.
PubChem CID 68577135 (Year: 2012).
International Search Report & Written Opinion received for PCT Appl. No. PCT/US21/40584, mailed on Dec. 10, 2021, 10 pages.
Keith et al., "Demethylation of 2,4-dimethoxyquinolines: the synthesis of atanine", Organic & Biomolecular Chemistry, England, Dec. 4, 2003 (Dec. 4, 2003), England, pp. 4380-4383, XP055898196, Retrieved from the Internet <URL:https://pubs.rsc.org/en/content/articlepdf/2003/ob/b311281k> [retrieved on Mar. 7, 2022], DOI: 10.1039/b311281k.
Vannelli et al.: "The Antituberculosis Drug Ethionamide Is Activated by a Flavoprotein Monooxygenase", The Journal of Biological Chemistry, vol. 277, No. 15, 2002, pp. 12824-12829, XP002283431, DOI: 10.1074/jbc.M110751200.
PubChem SID 24847096 (Year: 2018).
International Search Report & Written Opinion received for PCT Appl. No. PCT/US21/39470, mailed on Oct. 27, 2021, 15 pages.
International Preliminary report of Patentability received for PCT Appl. No. PCT/US21/40588, mailed on Jan. 10, 2023, 10 pages.

(56) References Cited

OTHER PUBLICATIONS

International Search Report & Written Opinion received for PCT Appl. No. PCT/US21/14250, mailed on Jun. 9, 2021, 4 pages.
International Preliminary report of Patentability received for PCT Appl. No. PCT/US21/14250, mailed on Jul. 26, 2023, 8 pages.
PubChem-SID-24847096, Modify Date: Mar. 14, 2018 (Mar. 14, 2018), p. 2, fig.
Labaudinière et al., "ω-[(4-Phenyl-2-quinolyl)oxy]alkanoic Acid Derivatives: A New Family of Potent LTB4 Antagonists", Journal of medicinal chemistry, 1992, 35 (23), pp. 4306-4314.
Hussaini, "Therapeutic significance of quinolines: a patent review (2013-2015)", Expert Opinion on Therapeutic Patents, 2016, 26 (10), pp. 57.
Non-Final Office Action received in U.S. Appl. No. 17/566,692, Mailed on May 22, 2024, pp. 38.
Supplementary Partial European Search Report received in EP application No. 21744382, Mailed on Apr. 22, 2024, pp. 15.
Extended European Search Report received in EP application No. 21829660, Mailed on Jun. 3, 2024, pp. 5.
Escote X, et al., "A study of fatty acid binding protein 4 in HIV-1 infection and in combination antiretroviral therapy-related metabolic disturbances and lipodystrophy", Journal of HIV Medicine, vol. 12, No. 7, dated Jan. 19, 2011, pp. 428-437.
Extended European Search Report received in EP application No. 218376655, Mailed on Jul. 4, 2024, pp. 16.

\* cited by examiner

ANTIVIRAL USE OF FABP4 MODULATING COMPOUNDS

FIELD OF THE EMBODIMENTS

The field of the embodiments of the present invention relate to antiviral therapies for treatment or prophylaxis of diseases caused by coronavirus infections. Compounds in this invention particularly interact with fatty acid binding protein 4 (FABP4) and inhibit the growth of coronaviruses in cells.

BACKGROUND OF THE EMBODIMENTS

FABPs are a family of proteins that reversibly bind free fatty acids and other lipid molecules and facilitate their transport in cells. To date, nine different FABP isoforms have been identified in mammals. FABP isoforms display differential expression patterns in different tissues. Fatty acid binding protein 4 (FABP4), also often referred to as aP2 in literature, is primarily expressed in adipocytes and macrophages, and mediates key metabolic and inflammatory pathways in these cells such as lipid storage and degradation, signaling and eicosanoid production. In addition, FABP4 is also secreted to plasma and has been proposed to act as an adipose-derived factor regulating systemic glucose homeostasis.

The present invention relates to the pharmaceutical industry and medicines and presents a new therapy for the treatment and prevention of acute viral infections, particularly acute respiratory viral infections and more particularly to therapy for coronavirus and severe acute respiratory syndrome (SARS) diseases, comprising the administration of a therapeutically effective dose of a compound described herein to a subject in need thereof.

Acute respiratory viral infections are a group of infectious diseases of viral etiology and characterized by damage to the respiratory tract and exhibiting common clinical symptoms. The successes achieved by medicine in the field of infectious pathology have contributed to the development and improvement of methods for the prevention and treatment of diseases, but acute respiratory viral infections continue to be a serious public health problem due to extremely high rates of incidence and the occurrence of epidemics and pandemics.

Acute respiratory viral infections are polyetiological. Currently, more than 200 relevant pathogens are known with rhinoviruses, coronaviruses, and influenza viruses frequently seen causing a high outbreak in the autumn and winter. Other viruses causing acute respiratory viral infections at relatively higher rates include respiratory syncytial viruses (RSVs), parainfluenza, adenoviruses, Human metapneumovirus (HMPV), Human Bocavirus (HBOV) along with unidentified viruses responsible for the remainder of acute infections of the respiratory tract of viral and unspecified etiology.

Of recent concern, SARS, a form of acute respiratory viral infection, presents as one of the leading severe diseases active in children and adults, resulting in temporary disability and significant mortality. The high incidence of SARS is associated with significant economic losses due to indirect costs associated with disability and compounded by societal and economic damage from governmentally imposed lockdowns instituted to prevent viral spread. Most seasonal morbidity is affected by children, the elderly, people with concomitant diseases (various immunodeficiencies, diseases of the lungs, cardiovascular system, liver, kidneys, diabetes, etc.).

Acute respiratory diseases of coronavirus etiology can be severe and cause extensive damage to lung tissue as well as other organs. Common human coronaviruses cause varying levels of acute respiratory infections. Viruses HCoV-OC43, and HCoV-HKUI, HCOV-229E, and HCoV-NL63 cause common colds and self-limiting upper respiratory infections in immunocompetent individuals. In immunocompromised subjects and the elderly, lower respiratory tract infections can occur. Other coronaviruses can cause more severe form of acute respiratory disease and include SARS-COV, SARS-COV-2, and MERS-COV. These coronaviruses can cause epidemics and pandemics with variable clinical severity featuring respiratory and extra-respiratory manifestations.

The COVID-19 pandemic caused by SARS-COV-2 dramatically demonstrated that there is a great unmet need for effective therapeutic agents that can broadly treat or prevent coronavirus infections. This highlighted the importance of host factors, independent of the viral proteins, that are intimately related to the virus life cycle and also the disease severity and mortality associated with viral infections.

The invention and embodiments thereof disclosed herein describes a novel class of antiviral agents that interact with fatty acid binding protein 4 (FABP4) and inhibit viral replication in human cells. FABP4 is a key mediator of fatty acid metabolism and inflammation, two pathways that have been implicated in the life cycle of many viral pathogens. Furthermore, FABP4 has been particularly associated with the development of a number of metabolic conditions such as diabetes, cardiovascular disease, and airway inflammation that are known to confer susceptibility to coronavirus, influenza virus and certain other virus infections. In view of the present discovery that compounds that target FABP4 also inhibit viral replication in cells, the compounds described in this invention present a universally applicable treatment for disease caused by known viruses and variants that emerge in future.

SUMMARY OF THE EMBODIMENTS

The present inventors have found that compounds that interact with a host protein FABP4 are potent and sustained inhibitors of viral replication in a host. The inventors have found that compounds that target FABP4 also inhibit viral replication and dramatically reduce virus production and the spread of infection. The inventors further found that certain compounds described herein are particularly suited to interact with FABP4 and protect against viruses causing acute respiratory viral infections. The inventors thus recognized that such compounds have applications in treating and/or preventing viral disease in a subject. The compounds can be advantageously provided in the form of an aerosol formulation. The compounds can advantageously be used in the form of a pharmaceutical composition comprising a pharmaceutically acceptable carrier or diluent. The compounds can also be advantageously used in the form of a combination comprising an additional antiviral agent. Such combination therapies have particular relevance in the prevention or treatment of viral infection caused by highly infectious viral strains such as epidemic or pandemic coronavirus.

The invention is a method for treating a viral disease in a subject comprising administering to said subject a therapeutically effective dose of a compound suited to interact with FABP4.

In further embodiments, the invention is a method for treating a viral disease in a subject comprising administering to said subject a therapeutically effective dose of one or more of the compounds described in Formula (I):

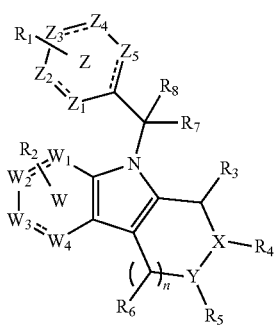

Formula (I)

Wherein:

$W_1$-4 and $Z_1$-$Z_5$ are each independently —C, —CH, $CH_2$, O, S, or N;

X is independently $CH_2$, N or $CHR_4$;

Y is independently $CH_2$, or $CHR_5$;

n is a number between 0 and 3;

One or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, wherein the substituted cycloaryl or cychloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, and $SO_2NH_2$;

One or more $R_2$'s on the ring W are independently selected from the group consisting of: CN, OH, $CHF_2$, $CH_2F$, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere;

R is alkyl;

when n is not zero, $R_3$, $R_4$, $R_5$ or $R_8$, or $R_6$ is each independently selected from:
(1) hydrogen;
(2) substituted or unsubstituted alkyl or ether having 1 to 12 carbon atoms,
(3) a substituted amine, or
(4) —$(CH_2)_m$ G, wherein m is 1 to 12 and G is independently selected from:
 (a) cycloalkyl containing 3 to 6 carbon atoms,
 (b) aryl or heteroaryl,
 (c) $CF_3$, $CF_2H$ or $CFH_2$, or
 (d) a heterocycle,
provided that $R_3$, $R_4$, $R_5$, Rx, or $R_6$ are not all hydrogen; or pharmaceutically acceptable salts or stereoisomers thereof.

In other embodiments the invention is a method for treating a viral disease in a subject comprising administering to said subject a therapeutically effective dose of a compound selected from the group consisting of: 5-[(3-cyanophenyl)methyl]-2-fluoro-7-hexyl-5H,6H, 7H, 8H,9H, 10H-cyclohepta[b]indole-4-carboxylic acid, 5-[(6-cyanopyridin-2-yl)methyl]-7-hexyl-5H,6H, 7H,8H,9H, 10H-cyclohepta[b]indole-4-carboxylic acid, 5-[(6-carbamoylpyridin-2-yl)methyl]-7-hexyl-5H,6H,7H,8H,9H, 10H-cyclohepta[b]indole-4-carboxylic acid, 6-({4-carboxy-7-hexyl-5H,6H, 7H, 8H,9H, 10H-cyclohepta[b]indol-5-yl}methyl)pyridine-2-carboxylic acid, 5-[(3-cyano-2-fluorophenyl)methyl]-7-hexyl-5H,6H,7H,8H,9H,10H-cyclohepta[b]indole-4-carboxylic acid, 5-[(1,3-benzoxazol-6-yl)methyl]-7-hexyl-5H,6H,7H,8H,9H,10H-cyclohepta[b]indole-4-carboxylic acid, 5-[(1,3-benzoxazol-5-yl)methyl]-7-hexyl-5H,6H, 7H, 8H,9H, 10H-cyclohepta[b]indole-4-carboxylic acid, 5-[(6-fluoropyridin-2-yl)methyl]-7-hexyl-5H,6H, 7H, 8H,9H, 10H-cyclohepta[b]indole-4-carboxylic acid, 5-[(2-fluoropyridin-4-yl)methyl]-7-hexyl-5H,6H,7H,8H,9H, 10H-cyclohepta[b]indole-4-carboxylic acid, 7-hexyl-5-{[6-(trifluoromethyl)pyridin-2-yl]methyl}-5H,6H, 7H,8H,9H, 10H-cyclohepta[b]indole-4-carboxylic acid, 7-hexyl-5-{[2-(trifluoromethyl)pyridin-4-yl]methyl}-5H,6H,7H,8H,9H, 10H-cyclohepta[b]indole-4-carboxylic acid, 5-[(5-cyanopyridin-3-yl)methyl]-7-hexyl-5H,6H, 7H, 8H,9H, 10H-cyclohepta[b]indole-4-carboxylic acid, 5-[(5-cyanothiophen-2-yl)methyl]-7-hexyl-5H,6H,7H,8H,9H,10H-cyclohepta[b]indole-4-carboxylic acid, 5-[(4-cyanothiophen-2-yl)methyl]-7-hexyl-5H,6H,7H,8H,9H, 10H-cyclohepta[b]indole-4-carboxylic acid, 5-[(5-cyanofuran-2-yl)methyl]-7-hexyl-5H,6H,7H,8H,9H, 10H-cyclohepta[b]indole-4-carboxylic acid, 5-[(3,5-dimethyl-1,2-oxazol-4-yl)methyl]-7-hexyl-5H,6H,7H,8H,9H,10H-cyclohepta[b]indole-4-carboxylic acid, 5-(3-cyanobenzoyl)-7-hexyl-5H,6H,7H, 8H,9H, 10H-cyclohepta[b]indole-4-carboxylic acid, 5-[(1,3-benzoxazol-7-yl)methyl]-7-hexyl-5H,6H, 7H, 8H,9H, 10H-cyclohepta[b]indole-4-carboxylic acid, 5-[(5-cyanothiophen-3-yl)methyl]-7-hexyl-5H,6H,7H,8H,9H,10H-cyclohepta[b]indole-4-carboxylic acid, 7-hexyl-5-[(1H-indol-4-yl)methyl]-5H,6H,7H,8H,9H, 10H-cyclohepta[b]indole-4-carboxylic acid, 5-[(3-carbamoylphenyl)methyl]-7-propyl-5H,6H,7H,8H,9H, 10H-cyclohepta[b]indole-4-carboxylic acid, 7-butyl-5-[(3-carbamoylphenyl)methyl]-5H,6H, 7H, 8H,9H, 10H-cyclohepta[b]indole-4-carboxylic acid, 7-butyl-5-[(3-cyanophenyl)methyl]-5H,6H, 7H,8H, 9H, 10H-cyclohepta[b]indole-4-carboxylic acid, 7-butyl-5-[(pyridin-3-yl)methyl]-5H,6H,7H,8H,9H, 10H-cyclohepta[b]indole-4-carboxylic acid, 7-butyl-5-[(3-methylphenyl)methyl]-5H,6H,7H,8H,9H,10H-cyclohepta[b]indole-4-carboxylic acid, 7-butyl-5-[(3-methoxyphenyl)methyl]-5H, 6H, 7H, 8H,9H, 10H-cyclohepta[b]indole-4-carboxylic acid, 7-butyl-5-[(3-chlorophenyl)methyl]-5H,6H, 7H,8H, 9H, 10H-cyclohepta[b]indole-4-carboxylic acid, 7-butyl-5-[(3-hydroxyphenyl)methyl]-5H,6H,7H,8H,9H,10H-cyclohepta[b]indole-4-carboxylic acid, 7-butyl-5-[(2-methoxypyridin-4-yl)methyl]-5H,6H,7H,8H,9H, 10H-cyclohepta[b]indole-4-carboxylic acid, 7-butyl-5-[(4-carbamoylphenyl)methyl]-5H,6H, 7H,8H,9H, 10H-cyclohepta[b]indole-4-carboxylic acid, 7-butyl-5-[(2-carbamoylphenyl)methyl]-5H,6H, 7H, 8H,9H, 10H-cyclohepta[b]indole-4-carboxylic acid, 7-butyl-5-[(4-methylphenyl)methyl]-5H,6H, 7H,8H,9H, 10H-cyclohepta[b]indole-4-carboxylic acid, 7-butyl-5-[(2-cyanophenyl)methyl]-5H,6H,7H,8H,9H, 10H-cyclohepta[b]indole-4-carboxylic acid, 7-butyl-5-[(2-methylphenyl)methyl]-5H, 6H, 7H,8H,9H, 10H-cyclohepta[b]indole-4-carboxylic acid, 7-butyl-5-[(2-fluorophenyl)methyl]-5H,6H,7H,8H,9H, 10H-cyclohepta[b]indole-4-carboxylic acid, 5-[(3-carbamoylphenyl)methyl]-7-pentyl-5H,6H, 7H,8H,9H, 10H-cyclohepta[b]indole-4-carboxylic acid, 5-[(3-cyanophenyl)methyl]-7-pentyl-5H,6H, 7H,8H,9H, 10H-cyclohepta[b]

indole-4-carboxylic acid, 5-[(3-carbamoylphenyl)methyl]-7-(2-phenylethyl)-5H,6H, 7H, 8H,9H, 10H-cyclohepta[b]indole-4-carboxylic acid, 5-[(3-cyanophenyl)methyl]-7-(2-phenylethyl)-5H,6H,7H,8H,9H, 10H-cyclohepta[b]indole-4-carboxylic acid, 5-[(3-carbamoylphenyl)methyl]-7-hexyl-5H,6H,7H,8H,9H,10H-cyclohepta[b]indole-4-carboxylic acid, 5-[(3-cyanophenyl)methyl]-7-hexyl-5H,6H, 7H,8H, 9H, 10H-cyclohepta[b]indole-4-carboxylic acid, 5-[(3-carbamoylphenyl)methyl]-7-octyl-5H,6H,7H,8H,9H, 10H-cyclohepta[b]indole-4-carboxylic acid, 5-[(3-cyanophenyl)methyl]-7-octyl-5H,6H, 7H, 8H, 9H, 10H-cyclohepta[b]indole-4-carboxylic acid, 5-[(3-fluorophenyl)methyl]-7-hexyl-5H,6H, 7H, 8H,9H-cyclohepta[b]indole-4-carboxylic acid, 7-hexyl-5-[(pyridin-3-yl)methyl]-5H,6H, 7H,8H,9H, 10H-cyclohepta[b]indole-4-carboxylic acid, 7-hexyl-5-[(3-methylphenyl)methyl]-5H,6H, 7H,8H,9H, 10H-cyclohepta[b]indole-4-carboxylic acid, 7-hexyl-5-[(3-methoxyphenyl)methyl]-5H,6H,7H,8H,9H, 10H-cyclohepta[b]indole-4-carboxylic acid, 5-[(3-chlorophenyl)methyl]-7-hexyl-5H,6H,7H,8H,9H, 10H-cyclohepta[b]indole-4-carboxylic acid, 7-hexyl-5-[(2-methoxypyridin-4-yl)methyl]-5H,6H,7H,8H,9H, 10H-cyclohepta[b]indole-4-carboxylic acid, 5-[(3-carboxyphenyl)methyl]-7-hexyl-5H, 6H,7H,8H,9H, 10H-cyclohepta[b]indole-4-carboxylic acid, 5-[(4-carbamoylphenyl)methyl]-7-hexyl-5H,6H, 7H, 8H,9H, 10H-cyclohepta[b]indole-4-carboxylic acid, 5-[(2-carbamoylphenyl)methyl]-7-hexyl-5H,6H, 7H,8H,9H, 10H-cyclohepta[b]indole-4-carboxylic acid, 7-hexyl-5-[(4-methylphenyl)methyl]-5H,6H, 7H,8H,9H, 10H-cyclohepta[b]indole-4-carboxylic acid, 5-[(4-cyanophenyl)methyl]-7-hexyl-5H,6H,7H,8H,9H, 10H-cyclohepta[b]indole-4-carboxylic acid, 5-[(2-cyanophenyl)methyl]-7-hexyl-5H, 6H,7H,8H,9H, 10H-cyclohepta[b]indole-4-carboxylic acid, 7-hexyl-5-[(2-methylphenyl)methyl]-5H,6H,7H,8H,9H, 10H-cyclohepta[b]indole-4-carboxylic acid, 5-[(2-fluorophenyl)methyl]-7-hexyl-5H,6H, 7H,8H,9H,10H-cyclohepta[b]indole-4-carboxylic acid, 5-[(4-fluorophenyl)methyl]-7-hexyl-5H,6H,7H,8H,9H, 10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H, 10H-cyclohepta[b]indole-4-carboxylic acid, 6-butyl-5-[(3-cyanophenyl)methyl]-5H,6H,7H,8H,9H,10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3-ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H, 10H-cyclohepta[b]indole-4-carboxylic acid, 5-[(3-cyanophenyl)methyl]-10-ethyl-5H,6H,7H,8H,9H,10H-cyclohepta[b]indole-4-carboxylic acid, 5-[(3-carbamoylphenyl)methyl]-10-propyl-5H,6H,7H,8H,9H, 10H-cyclohepta[b]indole-4-carboxylic acid, 5-[(3-cyanophenyl)methyl]-10-propyl-5H,6H, 7H, 8H,9H, 10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H,10H-cyclohepta[b]indole-4-carboxylic acid, 10-butyl-5-[(3-cyanophenyl)methyl]-5H,6H, 7H,8H,9H, 10H-cyclohepta[b]indole-4-carboxylic acid, 5-[(3-carbamoylphenyl)methyl]-10-pentyl-5H,6H,7H,8H,9H, 10H-cyclohepta[b]indole-4-carboxylic acid, 5-[(3-cyanophenyl)methyl]-10-pentyl-5H,6H,7H,8H,9H, 10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3- carbamoylphenyl)methyl]-7-ethyl-5H,6H, 7H, 8H,9H, 10H-cyclohepta[b]indole-4-carboxylic acid, 5-[(3-cyanophenyl)methyl]-7-ethyl-5H,6H, 7H,8H,9H, 10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H,10H-cyclohepta[b]indol-4-yl}formamido)acetic acid, 2-({7-butyl-5-[(3-cyanophenyl)methyl]-5H,6H,7H,8H,9H,10H-cyclohepta[b]indol-4-yl}formamido)acetic acid, 7-butyl-5-[(3-carbamoylphenyl)methyl]-N-(2-hydroxyethyl)-5H,6H, 7H, 8H,9H, 10H-cyclohepta[b]indole-4-carboxamide, 7-butyl-5-[(3-cyanophenyl)methyl]-N-(2-hydroxyethyl)-5H,6H,7H,8H, 9H, 10H-cyclohepta[b]indole-4-carboxamide, 7-butyl-5-[(3-fluorophenyl)methyl]-5H,6H,7H,8H,9H,10H-cyclohepta[b]indole-4-carboxylic acid, and 7-butyl-5-[(3-carboxyphenyl)methyl]-5H,6H,7H,8H,9H, 10H-cyclohepta[b]indole-4-carboxylic acid, or pharmaceutically acceptable salts or stereoisomers thereof.

Yet in other embodiments the invention is a method for treating a viral disease in a subject comprising administering to said subject a therapeutically effective dose of a compound selected from the group consisting of: 2-((2'-(5-Ethyl-3,4-diphenyl-1H-pyrazol-1-yl)-[1,1'-biphenyl]-3-yl)oxy)acetic acid, 6-chloro-4-phenyl-2-(piperidin-1-yl)-3-(1H-tetrazol-5-yl)quinoline, 5-((3-chloro-2-methylphenoxy)methyl)-2-phenyl-[1,2,4]triazolo[1,5-a]pyrimidin-7(4H)-one, and 3-(5-cyclopropyl-3-(3,5-dimethyl-1H-pyrazol-4-yl)-2-(3-isopropoxyphenyl)-1H-indol-1-yl)propanoic acid, or pharmaceutically acceptable salts or stereoisomers thereof. It should be appreciated that WO 00/59506, U.S. 2013/0116234 A1, WO 2010/056631, PCT/US21/39470, U.S. 2013/0116231 A1, Sulsky et al., Bioorg Med Chem Lett. 2007 Jun. 15; 17(12):3511-5. doi: 10.1016/j.bmcl.2006.12.044. Epub 2006 Dec 21, Kuhne et al., Bioorg Med Chem Lett. 2016 Oct. 15; 26(20):5092-5097. doi: 10.1016/j.bmcl.2016.08.071. Epub 2016 Aug 22.), and Lan et al., J Lipid Res. 2011 April; 52(4):646-56. doi: 10.1194/jlr.M012757. Epub 2011 Feb 4.), Tagami et al., ACS Med Chem Lett. 2016 Apr. 14; 7(4): 435-439. doi: 10.1021/acsmedchemlett.6b00040) are hereby incorporated by reference in their entirety.

It is an object of the present invention to utilize the compounds described herein in the treatment of viral disorders by acting on the fatty acid binding protein (FABP4).

Yet another object of the present invention is a pharmaceutical composition comprising a compounds herein as active ingredient, in combination with a pharmaceutically acceptable diluent or carrier for use in the treatment of viral disorders by acting on FABP4. Here, the pharmaceutical composition can further comprise an additional therapeutically active agent.

Yet another object of the present invention is a method for the treatment of viral disorders by acting on the FABP4, which comprises administering to a subject in need of such treatment (preferably a human) an effective amount of the compounds herein, including, optionally, the co-administration with other therapeutic agents, either as a single (or multiple) dosing, and either simultaneously or sequentially.

Yet another object of the present invention is the use of the compounds herein for the manufacture of a medicament for use in the treatment of viral disorders by acting on the fatty acid binding protein FABP4.

Examples of such disorders include common cold, SARS, and COVID-19.

Other features and advantages of the invention will be apparent from the detailed description and the claims.

DESCRIPTION OF THE PREFERRED EMBODIMENTS

Figure 1A:
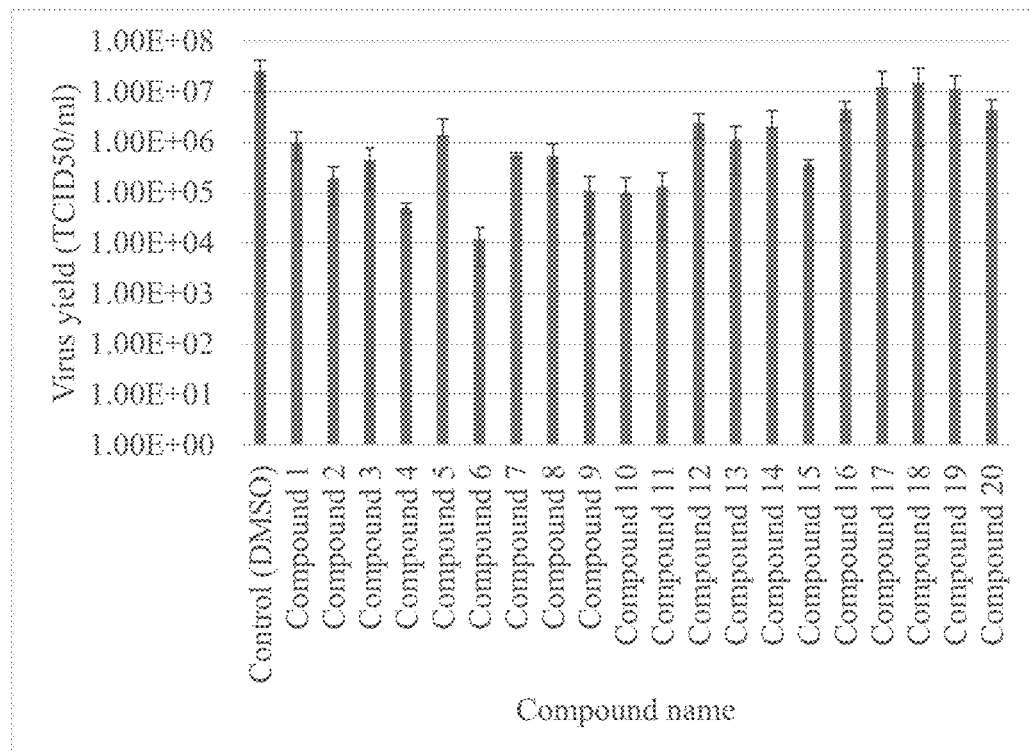
FIG. 1A and FIG. 1B depict graphical charts showing a virus yield obtained from cells treated with corresponding compounds and vehicle control (DMSO), according to at least some embodiments disclosed herein.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be.

The invention is a method for treating a viral disease in a subject comprising administering to said subject a therapeutically effective dose of one or more of the compounds described in Formula (I):

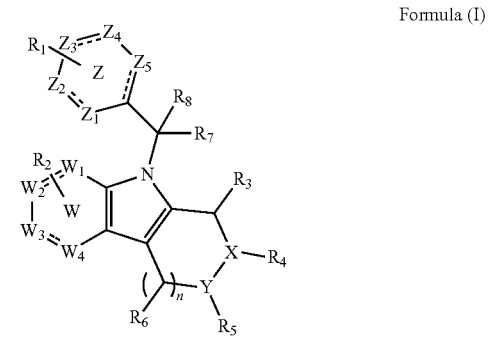

Formula (I)

Wherein:
$W_1$-4 and $Z_1$-$Z_5$ are each independently —C, —CH, $CH_2$, O, S, or N;
X is independently $CH_2$, N or $CHR_4$;
Y is independently $CH_2$, or $CHR_5$;
n is a number between 0 and 3;

One or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, wherein the substituted cycloaryl or cychloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, and $SO_2NH_2$;

One or more $R_2$'s on the ring W are independently selected from the group consisting of: CN, OH, $CHF_2$, $CH_2F$, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere;

R is alkyl;

when n is not zero, $R_3$, $R_4$, $R_5$ or $R_8$, or $R_6$ is each independently selected from:
(1) hydrogen;
(2) substituted or unsubstituted alkyl or ether having 1 to 12 carbon atoms,
(3) a substituted amine, or
(4) —$(CH_2)_m$ G, wherein m is 1 to 12 and G is independently selected from:
 (a) cycloalkyl containing 3 to 6 carbon atoms,
 (b) aryl or heteroaryl,
 (c) $CF_3$, $CF_2H$ or $CFH_2$, or
 (d) a heterocycle;
provided that $R_3$, $R_4$, $R_5$, $R_8$, or $R_6$ are not all hydrogen; or pharmaceutically acceptable salts or stereoisomers thereof.

In examples, where $R_1$ and $R_2$ are both present, each is independently CN, COOH, or $CONH_2$.

In examples, Formula I includes more than one $R_1$ and more than one $R_2$.

In examples, $R_3$, $R_4$, $R_5$ $R_8$, or $R_6$, when n is not zero, are each independently alkyl having 4 carbon atoms.

In examples, $R_3$, $R_4$, $R_5$ $R_8$, or $R_6$, when n is not zero, are each independently alkyl having 5 carbon atoms.

In examples, $R_3$, $R_4$, $R_5$ $R_8$, or $R_6$, when n is not zero, are each independently alkyl having 6 carbon atoms.

In examples, the ring Z contains $Z_1$-$Z_4$.
In examples, the ring Z contains $Z_1$-$Z_5$.
In examples, the $R_1$ on the ring Z is the halogen.
In examples, the $R_1$ on the ring Z is the CN.
In examples, the $R_1$ on the ring Z is the $CF_3$.
In examples, $R_2$ on the ring W is the halogen.
In examples, the $R_1$ on the ring Z comprise the CN and/or the halogen.

In examples, $R_1$ on the ring Z comprise the CN and/or the halogen, and the $R_2$ on the ring W comprise another halogen. In examples, the halogen is identical to the other halogen. In other examples, the halogen differs from the other halogen.

In examples, each of the one or more compounds are a pure optical isomer.

The invention also describes a method for treating a viral disease in a subject comprising administering to said subject a therapeutically effective dose of one or more compounds described in Formula (II):

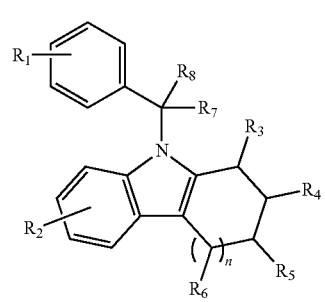

Formula (II)

Wherein:
n=0, 1, or 2;
$R_1$ is selected from the group consisting of: CN, COOH, $CONH_2$, $B(OH)_2$, $B(OR)_2$, an acid isostere, and a halogen;
$R_2$ is selected from the group consisting of: CN, COOH, $CONH_2$, $B(OH)_2$, $B(OR)_2$, an acid isostere, a halogen, and a bicyclic compound;
$R_7$ is hydrogen or CN, COOH, $CONH_2$, $B(OH)_2$, $B(OR)_2$ or an acid isostere;
R is alkyl;
$R_3$, $R_4$, $R_5$ or $R_8$, or $R_6$ when n is not zero, is each independently selected from:
(1) hydrogen;
(2) alkyl having 1 to 12 carbon atoms, or
(3) —$(CH_2)_m$G, wherein m is 1 to 12 and G is independently selected from:
 (a) cycloalkyl containing 3 to 6 carbon atoms,
 (b) aryl or heteroaryl, or
 (c) $CF_3$, $CF_2H$ or $CFH_2$;
provided that G is not a nitrogen or oxygen-containing group; and
provided that $R_3$, $R_4$, $R_5$, $R_5$, or $R_6$ are not all hydrogen; or pharmaceutically acceptable salts thereof.

In examples, when $R_1$ and $R_2$ are both present, each is independently CN, COOH, or $CONH_2$.

In examples, Formula II includes more than one $R_1$ and more than one $R_2$.

In examples, $R_3$, $R_4$, $R_5$, $R_5$, or $R_6$, when n is not zero, are each independently alkyl having 4 carbon atoms.

In examples, $R_3$, $R_4$, $R_5$, $R_5$, or $R_6$, when n is not zero, are each independently alkyl having 5 carbon atoms.

In examples, $R_3$, $R_4$, $R_5$, $R_5$, or $R_6$, when n is not zero, are each independently alkyl having 6 carbon atoms.

The present invention also describes a method for treating a viral disease in a subject comprising administering to said subject a therapeutically effective dose of one or more of the compounds described in Formula (III):

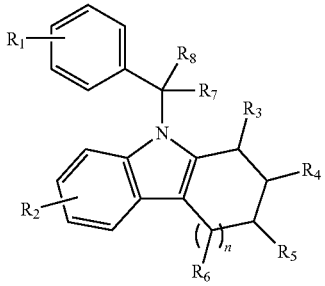

Formula (III)

Wherein:

n=0, 1, or 2;

$R_1$ and $R_2$ are each independently halogen, alkyl, cycloalkyl, aryl, heteroaryl, CN, COOH, $CONH_2$, $B(OH)_2$, $B(OR)_2$, or an acid isostere;

$R_7$ is hydrogen, alkyl, cycloalkyl, aryl, heteroaryl, CN, COOH, $CONH_2$, $B(OH)_2$, $B(OR)_2$ or an acid isostere;

R is alkyl;

$R_3$, $R_4$, $R_5$ or $R_5$, or $R_6$ when n is not zero, are each independently selected from:

(1) hydrogen;

(2) alkyl having 1 to 12 carbon atoms, or (3) —$(CH_2)_m G$, wherein m is 1 to 12 and G is independently selected from:

(a) cycloalkyl containing 3 to 6 carbon atoms;

(b) aryl or heteroaryl; or (c) $CF_3$, $CF_2H$, or $CFH_2$;

provided that $R_3$, $R_4$, $R_5$, $R_5$, or $R_6$ are not all hydrogen; or pharmaceutically acceptable salts or stereoisomers thereof.

In examples, $R_3$, $R_4$, $R_5$, $R_5$, or $R_6$, when n is 1, are each independently alkyl having 4 carbon atoms.

In examples, $R_3$, $R_4$, $R_5$, $R_5$, or $R_6$, when n is 1, are each independently alkyl having 5 carbon atoms.

In examples, $R_3$, $R_4$, $R_5$, $R_5$, or $R_6$, when n is 1, are each independently alkyl having 6 carbon atoms.

The present invention also describes a method for treating a viral disease in a subject comprising administering to said subject a therapeutically effective dose of one or more of the of compounds described in Formula (IV):

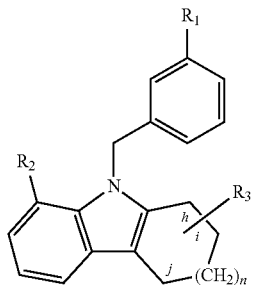

Formula (IV)

Wherein:

n=0, 1 or 2;

$R_1$ and $R_2$ are each independently CN, COOH or $CONH_2$;

$R_3$ is independently selected from:

(1) alkyl having 1 to 12 carbon atoms;

(2) —$(CH_2)_m G$, wherein m is 1 to 12 and G is independently selected from:

(a) cycloalkyl containing 3 to 6 carbon atoms;

(b) phenyl; and provided that G is not a nitrogen or oxygen-containing group;

or pharmaceutically acceptable salts thereof.

In examples, when n=0, $R_3$ is attached to the h-, i- or j-position.

In examples, when n=1, $R_3$ is attached to the h-, i- or j-position.

In examples, when n=2, $R_3$ is attached to the h-, i- or j-position.

In other embodiments the invention is a method for treating a viral disease in a subject comprising administering to said subject a therapeutically effective dose of a compound from PCT/US21/39470 filed on Jun. 28, 2021, U.S. Published Patent Application No. 2013/0116231 A1, or WO 2010/056631 A1, the entire contents of which are hereby incorporated by reference in their entirety.

In other examples, the invention provides a method for treating a viral disease in a subject comprising administering to said subject a therapeutically effective dose of one or more of the compounds selected from the group consisting of:

5-[(3-cyanophenyl)methyl]-2-fluoro-7-hexyl-5H,6H,7H, 8H,9H, 10H-cyclohepta[b]indole-4-carboxylic acid, 5-[(6-cyanopyridin-2-yl)methyl]-7-hexyl-5H,6H,7H,8H,9H,10H-cyclohepta[b]indole-4-carboxylic acid, 5-[(6-carbamoylpyridin-2-yl)methyl]-7-hexyl-5H,6H, 7H, 8H,9H, 10H-cyclohepta[b]indole-4-carboxylic acid, 6-({4-carboxy-7-hexyl-5H,6H, 7H, 8H,9H, 10H-cyclohepta[b]indol-5-yl}methyl)pyridine-2-carboxylic acid, 5-[(3-cyano-2-fluorophenyl)methyl]-7-hexyl-5H,6H,7H,8H,9H, 10H-cyclohepta[b]indole-4-carboxylic acid, 5-[(1,3-benzoxazol-6-yl)methyl]-7-hexyl-5H,6H,7H, 8H,9H, 10H-cyclohepta[b]indole-4-carboxylic acid, 5-[(1,3-benzoxazol-5-yl)methyl]-7-hexyl-5H,6H,7H,8H,9H, 10H-cyclohepta[b]indole-4-carboxylic acid, 5-[(6-fluoropyridin-2-yl)methyl]-7-hexyl-5H,6H, 7H, 8H,9H, 10H-cyclohepta[b]indole-4-carboxylic acid, 5-[(2-fluoropyridin-4-yl)methyl]-7-hexyl-5H,6H, 7H,8H,9H, 10H-cyclohepta[b]indole-4-carboxylic acid, 7-hexyl-5-{[6-(trifluoromethyl)pyridin-2-yl]methyl}-5H,6H,7H,8H,9H, 10H-cyclohepta[b]indole-4-carboxylic acid, 7-hexyl-5-{[2-(trifluoromethyl)pyridin-4-yl]methyl}-5H,6H,7H,8H,9H, 10H-cyclohepta[b]indole-4-carboxylic acid, 5-[(5-cyanopyridin-3-yl)methyl]-7-hexyl-5H,6H, 7H, 8H,9H, 10H-cyclohepta[b]indole-4-carboxylic acid, 5-[(5-cyanothiophen-2-yl)methyl]-7-hexyl-5H,6H,7H,8H,9H, 10H-cyclohepta[b]indole-4-carboxylic acid, 5-[(4-cyanothiophen-2-yl)methyl]-7-hexyl-5H,6H,7H,8H,9H, 10H-cyclohepta[b]indole-4-carboxylic acid, 5-[(5-cyanofuran-2-yl)methyl]-7-hexyl-5H,6H,7H,8H,9H, 10H-cyclohepta[b]indole-4-carboxylic acid, 5-[(3,5-dimethyl-1,2-oxazol-4-yl)methyl]-7-hexyl-5H,6H,7H,8H,9H,10H-cyclohepta[b]indole-4-carboxylic acid, 5-(3-cyanobenzoyl)-7-hexyl-5H, 6H,7H,8H,9H, 10H-cyclohepta[b]indole-4-carboxylic acid, 5-[(1,3-benzoxazol-7-yl)methyl]-7-hexyl-5H,6H, 7H, 8H,9H, 10H-cyclohepta[b]indole-4-carboxylic acid, 5-[(5-cyanothiophen-3-yl)methyl]-7-hexyl-5H,6H,7H,8H,9H, 10H-cyclohepta[b]indole-4-carboxylic acid, 7-hexyl-5-[(1H-indol-4-yl)methyl]-5H,6H,7H,8H,9H, 10H-cyclohepta[b]indole-4-carboxylic acid, 5-[(3-carbamoylphenyl)methyl]-7-propyl-5H,6H, 7H,8H,9H, 10H-cyclohepta[b]indole-4-carboxylic acid, 7-butyl-5-[(3-carbamoylphenyl)methyl]-5H,6H,7H,8H,9H,10H-cyclohepta[b]indole-4-carboxylic acid, 7-butyl-5-[(3-cyanophenyl)methyl]-5H,6H, 7H,8H,9H, 10H-cyclohepta[b]indole-4-carboxylic acid, 7-butyl-5-[(pyridin-3-yl)methyl]-5H,6H,7H,8H,9H, 10H-cyclohepta[b]indole-4-carboxylic acid, 7-butyl-5-[(3-methylphenyl)methyl]-5H,6H,7H,8H,9H, 10H-cyclohepta[b]indole-4-carboxylic acid, 7-butyl-5-[(3-methoxyphenyl)methyl]-5H,6H, 7H, 8H,9H, 10H-cyclohepta[b]indole-4-carboxylic acid, 7-butyl-5-[(3-chlorophenyl)methyl]-5H, 6H, 7H,8H,9H, 10H-cyclohepta[b]indole-4-carboxylic acid, 7-butyl-5-[(3-hydroxyphenyl)methyl]-5H,6H,7H,8H,9H, 10H-cyclohepta[b]indole-4-carboxylic acid, 7-butyl-5-[(2-methoxypyridin-4-yl)methyl]-5H,6H,7H,8H,9H, 10H-cyclohepta[b]indole-4-carboxylic acid, 7-butyl-5-[(4-carbamoylphenyl)methyl]-5H,6H, 7H,8H,9H, 10H-cyclohepta[b]indole-4-carboxylic acid, 7-butyl-5-[(2-carbamoylphenyl) methyl]-5H,6H, 7H, 8H,9H, 10H-cyclohepta[b]indole-4-carboxylic acid, 7-butyl-5-[(4-methylphenyl)methyl]-5H, 6H, 7H,8H,9H, 10H-cyclohepta[b]indole-4-carboxylic acid, 7-butyl-5-[(2-cyanophenyl)methyl]-5H,6H,7H,8H,9H, 10H-cyclohepta[b]indole-4-carboxylic acid, 7-butyl-5-[(2-methylphenyl)methyl]-5H,6H, 7H,8H,9H, 10H-cyclohepta[b]indole-4-carboxylic acid, 7-butyl-5-[(2-fluorophenyl)methyl]-5H,6H, 7H,8H,9H, 10H-cyclohepta[b]indole-4-carboxylic acid, 5-[(3-carbamoylphenyl)methyl]-7-pentyl-5H,6H,7H,8H,9H, 10H-cyclohepta[b]indole-4-carboxylic acid, 5-[(3-cyanophenyl)methyl]-7-pentyl-5H,6H, 7H,8H,9H, 10H-cyclohepta[b]indole-4-carboxylic acid, 5-[(3-carbamoylphenyl)methyl]-7-(2-phenylethyl)-5H,6H, 7H,8H,9H, 10H-cyclohepta[b]indole-4-carboxylic acid, 5-[(3-cyanophenyl)methyl]-7-(2-phenylethyl)-5H,6H,7H,8H,9H, 10H-cyclohepta[b]indole-4-carboxylic acid, 5-[(3-carbamoylphenyl)methyl]-7-hexyl-5H,6H,7H,8H,9H,10H-cyclohepta[b]indole-4-carboxylic acid, 5-[(3-cyanophenyl)methyl]-7-hexyl-5H,6H, 7H,8H,9H, 10H-cyclohepta[b]indole-4-carboxylic acid, 5-[(3-carbamoylphenyl)methyl]-7-octyl-5H,6H,7H,8H,9H,10H-cyclohepta[b]indole-4-carboxylic acid, 5-[(3-cyanophenyl)methyl]-7-octyl-5H,6H, 7H, 8H,9H, 10H-cyclohepta[b]indole-4-carboxylic acid, 5-[(3-fluorophenyl)methyl]-7-hexyl-5H,6H, 7H, 8H,9H, 10H-cyclohepta[b]indole-4-carboxylic acid, 7-hexyl-5-[(pyridin-3-yl)methyl]-5H,6H,7H,8H,9H,10H-cyclohepta[b]indole-4-carboxylic acid, 7-hexyl-5-[(3-methylphenyl)methyl]-5H,6H,7H,8H,9H, 10H-cyclohepta[b]indole-4-carboxylic acid, 7-hexyl-5-[(3-methoxyphenyl)methyl]-5H,6H,7H,8H,9H, 10H-cyclohepta[b]indole-4-carboxylic acid, 5-[(3-chlorophenyl)methyl]-7-hexyl-5H,6H,7H,8H,9H, 10H-cyclohepta[b]indole-4-carboxylic acid, 7-hexyl-5-[(2-methoxypyridin-4-yl)methyl]-5H,6H,7H,8H,9H, 10H-cyclohepta[b]indole-4-carboxylic acid, 5-[(3-carboxyphenyl)methyl]-7-hexyl-5H,6H,7H,8H,9H, 10H-cyclohepta[b]indole-4-carboxylic acid, 5-[(4-carbamoylphenyl)methyl]-7-hexyl-5H,6H, 7H, 8H,9H, 10H-cyclohepta[b]indole-4-carboxylic acid, 5-[(2-carbamoylphenyl)methyl]-7-hexyl-5H,6H, 7H,8H,9H, 10H-cyclohepta[b]indole-4-carboxylic acid, 7-hexyl-5-[(4-methylphenyl)methyl]-5H,6H, 7H,8H, 9H, 10H-cyclohepta[b]indole-4-carboxylic acid, 5-[(4-cyanophenyl)methyl]-7-hexyl-5H,6H,7H,8H,9H, 10H-cyclohepta[b]indole-4-carboxylic acid, 5-[(2-cyanophenyl)methyl]-7-hexyl-5H,6H,7H,8H,9H,10H-cyclohepta[b]indole-4-carboxylic acid, 7-hexyl-5-[(2-methylphenyl)methyl]-5H,6H, 7H,8H,9H, 10H-cyclohepta[b]indole-4-carboxylic acid, 5-[(2-fluorophenyl)methyl]-7-hexyl-5H, 6H, 7H,8H,9H, 10H-cyclohepta[b]indole-4-carboxylic acid, 5-[(4-fluorophenyl)methyl]-7-hexyl-5H,6H,7H,8H,9H, 10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H, 10H-cyclohepta[b]indole-4-carboxylic acid, 6-butyl-5-[(3-cyanophenyl)methyl]-5H,6H,7H,8H,9H, 10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3-ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H,10H-cyclohepta[b]indole-4-carboxylic acid, 5-[(3-cyanophenyl)methyl]-10-ethyl-5H,6H,7H,8H,9H, 10H-cyclohepta[b]indole-4-carboxylic acid, 5-[(3-carbamoylphenyl)methyl]-10-propyl-5H,6H,7H,8H,9H, 10H-cyclohepta[b]indole-4-carboxylic acid, 5-[(3-cyanophenyl)methyl]-10-propyl-5H,6H, 7H, 8H,9H, 10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H, 10H-cyclohepta[b]indole-4-carboxylic acid, 10-butyl-5-[(3-cyanophenyl)methyl]-5H,6H,7H,8H,9H, 10H-cyclohepta[b]indole-4-carboxylic acid, 5-[(3-carbamoylphenyl)methyl]-10-pentyl-5H,6H, 7H,8H,9H, 10H-cyclohepta[b]indole-4- carboxylic acid, 5-[(3-cyanophenyl)methyl]-10-pentyl-5H,6H,7H,8H,9H, 10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3-carbamoylphenyl)methyl]-7-ethyl-5H,6H, 7H, 8H,9H, 10H-cyclohepta[b]indole-4-carboxylic acid, 5-[(3-cyanophenyl)methyl]-7-ethyl-5H,6H, 7H,8H,9H, 10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H,10H-cyclohepta[b]indol-4-yl} formamido)acetic acid, 2-({7-butyl-5-[(3-cyanophenyl)methyl]-5H,6H,7H,8H,9H,10H-cyclohepta[b]indol-4-yl} formamido)acetic acid, 7-butyl-5-[(3-carbamoylphenyl)methyl]-N-(2-hydroxyethyl)-5H,6H, 7H, 8H,9H, 10H-cyclohepta[b]indole-4-carboxamide, 7-butyl-5-[(3-cyanophenyl)methyl]-N-(2-hydroxyethyl)-5H,6H, 7H, 8H,9H, 10H-cyclohepta[b]indole-4-carboxamide, 7-butyl-5-[(3-fluorophenyl)methyl]-5H,6H,7H,8H,9H, 10H-cyclohepta[b]indole-4-carboxylic acid, and 7-butyl-5-[(3-carboxyphenyl)methyl]-5H,6H, 7H, 8H,9H, 10H-cyclohepta[b]indole-4-carboxylic acid, or pharmaceutically acceptable salts or stereoisomers thereof.

Yet in other embodiments the invention is a method for treating a viral disease in a subject comprising administering to said subject a therapeutically effective dose of a compound selected from the group consisting of: 2-((2'-(5-Ethyl-3,4-diphenyl-1H-pyrazol-1-yl)-[1,1'-biphenyl]-3-yl)oxy) acetic acid, 6-chloro-4-phenyl-2-(piperidin-1-yl)-3-(1H-tetrazol-5-yl)quinoline, 5-((3-chloro-2-methylphenoxy) methyl)-2-phenyl-[1,2,4]triazolo[1,5-a]pyrimidin-7(4H)-one, and 3-(5-cyclopropyl-3-(3,5-dimethyl-1H-pyrazol-4-yl)-2-(3-isopropoxyphenyl)-1H-indol-1-yl)propanoic acid, or pharmaceutically acceptable salts or stereoisomers thereof. It should be appreciated that WO 00/59506, U.S. 2013/0116234 A1, WO 2010/056631, PCT/US21/39470, U.S. 2013/0116231 A1, Sulsky et al., Bioorg Med Chem Lett. 2007 Jun. 15; 17(12):3511-5. doi: 10.1016/j.bmcl.2006.12.044. Epub 2006 Dec 21, Kuhne et al., Bioorg Med Chem Lett. 2016 Oct. 15; 26(20):5092-5097. doi: 10.1016/j.bmcl.2016.08.071. Epub 2016 Aug 22.), and Lan et al., J Lipid Res. 2011 April; 52(4):646-56. doi: 10.1194/jlr.M012757. Epub 2011 Feb 4.), Tagami et al., ACS Med Chem Lett. 2016 Apr. 14; 7(4): 435-439. doi: 10.1021/acsmedchemlett.6b00040) are hereby incorporated by reference in their entirety.

The invention also describes a method for treating a viral disease in a subject comprising administering to said subject a therapeutically effective dose of one or more of the compounds described in Formula (V):

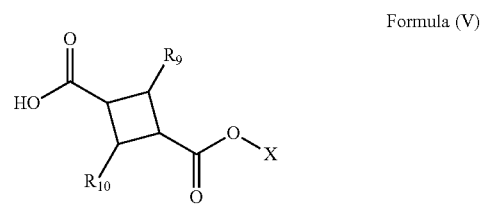

Formula (V)

Wherein:

$R_9$ and $R_{10}$ are each independently a phenyl or anisole; and

X comprises naphthalene or fluorene;

or pharmaceutically acceptable salts or stereoisomers thereof.

The invention also describes a method for treating a viral disease in a subject comprising administering to said subject a therapeutically effective dose of one or more of the compounds described in Formula (VI):

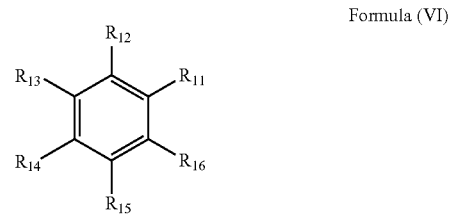

Formula (VI)

Wherein:

$R_{11}$ is —C(CH$_3$)$_2$ or

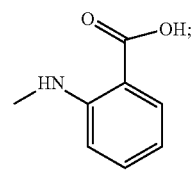

$R_{12}$ is —H, —O, a halogen, a phenyl, or piperidine;

$R_{13}$ is —C(CH$_3$)$_2$, a halogen, or

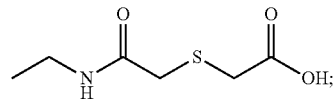

$R_{14}$ is a halogen, —$CF_3$, —$NHCH_3$, coumaran, or

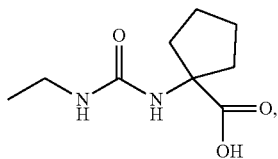

$R_{15}$ is —$C(CH_3)_2$ or a phenyl; and

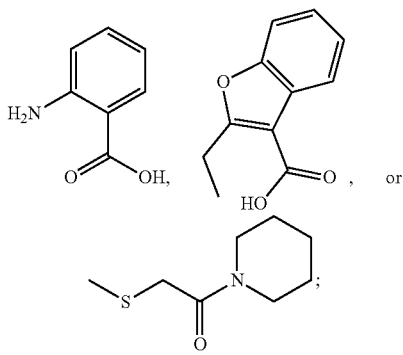

$R_{16}$ is —COOH, a halogen, —$SO_3H$, or pharmaceutically acceptable salts or stereoisomers thereof.

The invention describes a method for treating a viral disease in a subject comprising administering to said subject a therapeutically effective dose of one or more of the compounds described in Formula (VII):

Formula (VII)

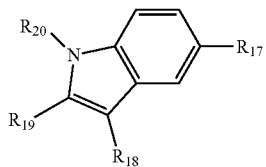

Wherein:
$R_{17}$ is cycloalkane;
$R_{18}$ is

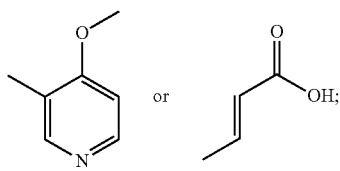

$R_{19}$ is a phenyl; and
$R_{20}$ is —$(CH_2)_2COOH$ or

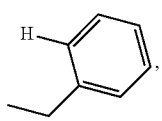

wherein H is a halogen;
or pharmaceutically acceptable salts or stereoisomers thereof.

The invention further describes a method for treating a viral disease in a subject comprising administering to said subject a therapeutically effective dose of one or more of the compounds described in Formula (VIII):

Formula (VIII)

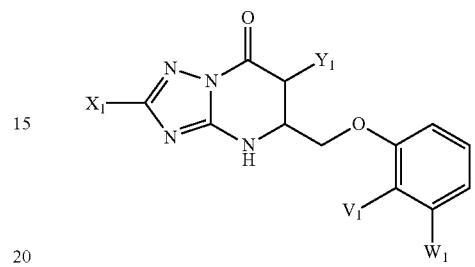

Wherein:
$X_1$ is a phenyl;
$Y_1$ and $W_1$ are independently a halogen; and
$V_1$ is —$CH_3$ or cycloalkane;
or pharmaceutically acceptable salts or stereoisomers thereof.

The invention describes a method for treating a viral disease in a subject comprising administering to said subject a therapeutically effective dose of one or more of the compounds described in Formula (IX):

Formula (IX)

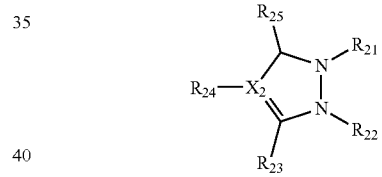

Wherein:
$X_2$ is —CH or O;

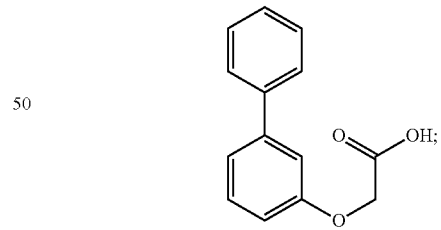

$R_{21}$ is —H or
$R_{22}$ is —H, —O, a phenyl, or

wherein H is a halogen;
R$_{23}$ is —H, thiophene, a phenyl,

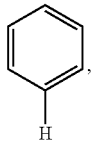

wherein H is a halogen; and
R$_{24}$ is —H or a phenyl; and
R$_{25}$ is —CH$_2$CH$_3$,

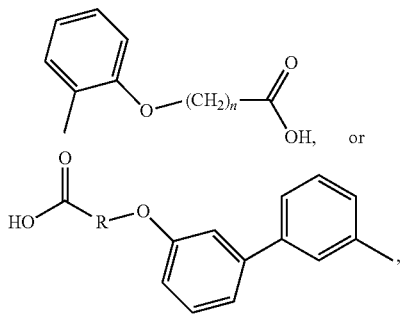

wherein n is 3 or 4, and wherein R is —CH$_2$ or —C(CH$_3$)$_2$; or pharmaceutically acceptable salts or stereoisomers thereof.

The invention describes a method for treating a viral disease in a subject comprising administering to said subject a therapeutically effective dose of a compound selected from the group consisting of: 2-((2'-(5-ethyl-3,4-diphenyl-1H-pyrazol-1-yl)-[1,1'-biphenyl]-3-yl)oxy)acetic acid, 2-((2-oxo-2-((2-(piperidin-1-yl)benzyl)amino)ethyl)thio)acetic acid, (3,5-dibromo-4-hydroxyphenyl)(2-ethylbenzofuran-3-yl)methanone, (E)-4-((5-(methoxycarbonyl)-[2,2'-bithiophen]-3-yl)amino)-4-oxobut-2-enoic acid, 2-(1-(methoxymethyl)cyclopentyl)-6-pentyl-4-phenyl-3-(2H-tetrazol-5-yl)-5,6,7,8-tetrahydroquinoline, 2-cyclohexyl-4-(2-methylpyridin-4-yl)-3-(2/-tetrazol-5-yl)-6-(trifluoromethyl)-5,6,7,8-tetrahydroquinoline, 6-chloro-4-phenyl-2-(piperidin-1-yl)-3-(2H-tetrazol-5-yl)quinoline, 6-chloro-2-methyl-4-phenylquinoline-3-carboxylic acid, N-(2-(4-(1-allyl-2,4-dioxo-2,3,4,5-tetrahydro-1H-pyrrolo[3,2-d]pyrimidin-6-yl)phenoxy)ethyl)picolinamide, (5-chloro-3-hydroxyquinoxalin-2-yl)(2-(3,5-dichlorobenzyl)pyrrolidin-1-yl)methanone, 1-(3-(4,6-dichloro-[1,1'-biphenyl]-2-yl)ureido)cyclopentane-1-carboxylic acid, 5-((3-chloro-2-methylphenoxy)methyl)-2-phenyl-[1,2,4]triazolo[1,5-a]pyrimidin-7(4H)-one, 6-chloro-5-((3-chloro-2-cyclopropylphenoxy)methyl)-2-phenyl-[1,2,4]triazolo[1,5-a]pyrimidin-7(4H)-one, 2-((3-chloro-2-(2,3-dihydrobenzofuran-5-yl)phenyl)amino)benzoic acid, 2-((6-chloro-5-(methylamino)-[1,1'-biphenyl]-2-yl)amino)benzoic acid, (1S,2R,3S,4R)-2,4-bis(2-methoxyphenyl)-3-((naphthalen-1-yloxy)carbonyl)cyclobutane-1-carboxylic acid, (1R,2R,3R,4R)-3-(((9H-fluoren-9-yl)methoxy)carbonyl)-2,4-bis(2-methoxyphenyl)cyclobutane-1-carboxylic acid, (1R,2R,3R,4R)-3-((naphthalen-1-yloxy)carbonyl)-2,4-diphenylcyclobutane-1-carboxylic acid, 1-[1-[4,4-Bis(4-fluorophenyl)butyl]-4-piperidinyl]-1,3-dihydro-2H-benzimidazole-2-one, 2,4,6-triisopropylbenzoic acid, 2,4,6-triisopropylbenzenesulfonic acid, 2-((2'-(1-(4-chlorophenyl)-5-(thiophen-2-yl)-1H-pyrazol-3-yl)-[1,1'-biphenyl]-3-yl)oxy)-2-methylpropanoic acid, (E)-3-(1-(2-fluorobenzyl)-1H-indol-3-yl)acrylic acid, 4-(2-(5-(2-chlorophenyl)-1-phenyl-1H-pyrazol-3-yl)phenoxy)butanoic acid, 5-(2-(4,5-diphenyloxazol-2-yl)phenoxy)pentanoic acid, 2-((2'-(4,5-diphenyloxazol-2-yl)-[1,1'-biphenyl]-3-yl)oxy)acetic acid, 4-(9H-carbazol-9-yl)butanoic acid, 3-((9H-carbazol-9-yl)sulfonyl)thiophene-2-carboxylic acid, 5-(3-carbamoylbenzyl)-5,6,7,8,9,10-hexahydrocyclohepta[b]indole-4-carboxylic acid, 9-(2-(trifluoromethyl)benzyl)-2,3,4,9-tetrahydro-1H-carbazole-8-carboxylic acid, 3-(5-cyclopropyl-3-(3,5-dimethyl-1H-pyrazol-4-yl)-2-(3-isopropoxyphenyl)-1H-indol-1-yl)propanoic acid, 3-(5-cyclopropyl-3-(3-methoxypyridin-4-yl)-2-phenyl-1H-indol-1-yl)propanoic acid, and 2-((2-oxo-2-(piperidin-1-yl)ethyl)thio)-6-(trifluoromethyl)pyrimidin-4(3H)-one.

The present invention also describes a method for treating a viral disease in a subject comprising administering to said subject a therapeutically effective dose of one or more of the compounds described in Formula X:

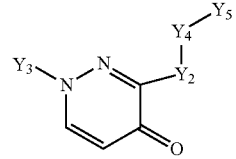

Formula X

Wherein:
Y$_2$ is CR$^{13}$R$^{13}$, 0, NR 15 or S;
Y$_3$ is heteroaryl or aryl, wherein said heteroaryl and aryl groups are optionally substituted with one to three groups independently selected from the group consisting of halo, cyano, C$_{1-6}$ alkyl, (C$_{1-6}$ alkyl)R$^{17}$, OR$^{17}$, (C=0)NR$^{15}$R$^{16}$, heterocyclyl, aryl, heteroaryl and (heteroaryl)R$^{16}$;
Y$_4$ is CR$^{14}$R$^{14}$0, C$_{2-3}$ alkenyl, 0, NR$^{15}$ or S;
Y$_5$ is heteroaryl or phenyl, wherein said heteroaryl and phenyl groups are optionally substituted with one to three groups independently selected from the group consisting of halo, cyano, oxo, C$_{1-6}$ alkyl, (C$_{1-6}$ alkyl)OR$^{16}$, OR$^{16}$, R$^{17}$, OR$^{17}$, 0(C$_{1-6}$ alkyl)OR$^{16}$, 0(C$_{1-6}$ alkyl)R$^{17}$, (C=0)R$^{16}$, (C=0)OR$^{16}$, (C=0)NHR$^{16}$, (C=0)R$^{17}$, NHR$^{16}$, NH(CO)OR$^{16}$, NH(C=0)R$^{17}$, NH(C=0)0, (C$_{1-6}$ alkyl)OR$^{16}$ and NO$_2$;
R$^{13}$ is hydrogen, halo or C$_{1-6}$ alkyl;
R$^{14}$ is hydrogen, halo, C$_1$-6 alkyl or (C=0)OR$^{16}$;
R$^{15}$ is hydrogen or C$_{1-6}$ alkyl,
R$^{16}$ is hydrogen or C$_{1-6}$ alkyl, wherein said alkyl is optionally substituted with one to three groups independently selected from the group consisting of halo and hydroxyl;
R$^{17}$ is hydrogen, heterocyclyl, aryl or heteroaryl, wherein said heterocyclyl and heteroaryl groups are optionally substituted with one to two groups independently selected from the group consisting of cyano, halo, hydroxyl, R$^{16}$, R$^{18}$, OR$^{16}$, (C$_{1-6}$ alkyl)OR$^{16}$, (C$_{1-6}$ alkyl)OR$^{18}$, SOiC$_{1-6}$ alkyl), (C=0)R$^{18}$; and
R$^{18}$ is heterocyclyl or heteroaryl, wherein said heterocyclyl group is optionally substituted with cyano, halo, hydroxyl, R$^{16}$, OR$^{16}$ or (C=0)OR$^{16}$;
or a pharmaceutically acceptable salt thereof.

The present invention also describes a method for treating a viral disease in a subject comprising administering to said subject a therapeutically effective dose of one or more of the compounds described in Formula (XI):

Formula XI

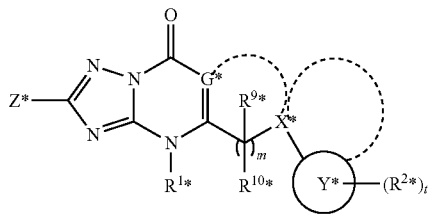

wherein:
Y* is a ring as described below;
X* is either:
(i) C(R>7'oR8$^a$), N(FT), S, S(O2), or O, and both

```
  ,-'''-.
 /       \
```
are absent; or
(ii) C(R$^7$), and X* is linked, either to the ring marked Y* as shown by the

```
  ,-'''-.
 /       \
```
towards the right of X*, or to the position marked G* on the triazolopyrimidinone ring as shown by the

```
  ,-'''-.
 /       \
```
towards the left of X*, to form a 3-8 membered cycloalkyl or a 4-8 membered heterocyclyl ring containing 1-3 heteroatoms independently selected from N, O and S, or (iii) N (with R$^3$ being absent), and X* is linked, either to the ring marked Y* as shown by the

```
  ,-'''-.
 /       \
```
towards the right of X*, or to the position marked G* on the triazolopyrimidinone ring as shown by the

```
  ,-'''-.
 /       \
```
towards the left of X*, to form a 4-8 membered heterocyclyl ring containing 1-3 heteroatoms independently selected from N, O and S, including the nitrogen atom of X*; further wherein

```
  ,-'''-.
 /       \
```
shown to the right of X* is mutually exclusive of

```
  ,-'''-.
 /       \
```
shown to the left of X*;
G* is C(R$^6$) when

```
  ,-'''-.
 /       \
```
shown to the left of X* is absent, and G* is C when

```
  ,-'''-.
 /       \
```
shown to the left of X* is present;
Ring Y* is aryl, heteroaryl, heterocyclyl or cycloalkyl, and when

```
  ,-'''-.
 /       \
```
shown to the right of X* is present, a ring atom on Y* is the point of attachment for said

```
  ,-'''-.
 /       \
```
shown to the right of X*, wherein each of said aryl, heteroaryl, heterocyclyl and cycloalkyl can be unsubstituted or optionally independently substituted with one or more substituents which can be the same or different, each substituent being independently selected from the group consisting of halo, hydroxyl, alkyl, alkoxy, CN and $CF_3$;
R$^3$ may be present or absent as stated above, and when R$^3$ is present, R$^3$ is H, alkyl or cycloalkyl, wherein each of said alkyl and cycloalkyl may be unsubstituted or optionally independently substituted with one or more substituents which can be the same or different, each substituent being independently selected from the group consisting of halo, hydroxyl, alkoxy, CN and $CF_3$;
R$^{1*}$ is H, alkyl, -alkyl-OR+, haloalkyl, haloalkoxy or -alkyl-CN; m is 1-2; t is 0-4; each
R$^{2*}$ is independently selected from the group consisting of halo, CN, —OR$^5$, alkyl, haloalkyl, haloalkoxy, aryl, heteroaryl, heterocyclyl, cycloalkyl, —NH$_2$, —NH(alkyl), —NH(aryl), —NH(heteroaryl), —NH(cycloalkyl), —S-alkyl, —S-aryl, —S-heteroaryl, —S-cycloalkyl, —C(O)OH, —C(O)—NH$_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—NH$_2$, —C(O)R$^5$, and —C(O)OR$^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxy!, cycloalkyl, alkoxy, —C(O)R$^5$, CN and $CF_3$;
R* is H, —OR$^5$, —C(O)OR$^5$, alkyl, alkenyl, alkynyl, cycloalkyl, haloalkyl, aryl or heteroaryl, wherein each of said alkyl, cycloalkyl, haloalkyl, aryl and heteroaryl may be unsubstituted or optionally independently substituted with one or more substituents which can be the same or different, each substituent being independently selected from the group consisting of halo, CN, —OR$^5$, alkyl, haloalkyl, haloalkoxy, aryl, heteroaryl, heterocyclyl, cycloalkyl, —C(O)—NH$_2$, —C(O)N(H)(CH$_3$), —NH—C(O)—NH$_2$, —C(O)R$^5$, and —C(O)OR$^5$;
R$^4$ is H, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$;
R$^5$ is H, alkyl, cycloalkyl, aryl or heteroaryl, wherein each of said alkyl, cycloalkyl, aryl and heteroaryl may be unsubstituted or optionally independently substituted with one or more substituents which can be the same or different, each substituents being independently selected from the group consisting of halo, hydroxyl, alkoxy, —OC(O)R$^4$, CN and $CF_3$; R$^6$ is H, halo, alkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; R$^7$ is H, alkyi, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$;

$R^8$ is H, alkyl, hydroxy or alkoxy, wherein each of said alkyl and alkoxy may be independently unsubstituted or optionally independently substituted with one or more substituents which can be the same or different, each substituent being independently selected from the group consisting of halo, hydroxyl, alkoxy, CN and $CF_3$;

$R^{9*}$ is H, halo, alkyl, cycloalkyl, aryl or heteroaryl, wherein each of said alkyl, aryl and heteroaryl may be unsubstituted or optionally independently substituted with one or more substituents which can be the same or different, each substituents being independently selected from the group consisting of halo, hydroxyl, alkoxy, CN and $CF_3$; and $R^{10*}$ is H, halo, alkyl, cycloalkyl, aryl or heteroaryl, —C(O)OH, —C(O)—$NH_2$, —C(O)N(H)(alkyl), —C(O)N(H)aryl, —C(O)N(H)(heteroaryl), —C(O)N(H)(heterocyclyl), —C(O)—N(H)(cycloalkyl), —C(O)N(alkyl)$_2$, —C(O)N(aryl)$_2$, —C(O)N(heteroaryl)$_2$, —C(O)N(heterocyclyl)$_2$, —C(O)—N(cycloalkyl)$_2$, —C(O)N(aryl)(alkyl), —C(O)N(heteroaryl)(aryl), —C(O)N(heterocyclyl)(heteroaryl), —C(O)N(aryl)(heterocyclyl), —C(O)—N(alkyl)(cycloalkyl), —C(O)N(cycloalkyl)(aryl), —C(O)N(cycloalkyl)(heterocyclyl), —NH—C(O)—$NH_2$, —C(O)$R^5$, and —C(O)OR$^5$, wherein each of said alkyl, aryl, heteroaryl, heterocyclyl and cycloalkyl may be unsubstituted or optionally independently substituted with one or more substituents which can be the same or different, each substituent being independently selected from the group consisting of halo, alkyl, aryl, heteroaryl, hydroxyl, cycloalkyl, alkoxy, —C(O)$R^5$, CN and $CF_3$; or alternatively, $R^{9*}$ and $R^{10*}$ can together form —O or $R^{9*}$ and $R^{10*}$ can be joined to form a spirocyclyl group.

The present invention also describes a method for treating a viral disease in a subject comprising administering to said subject a therapeutically effective dose of one or more of the compounds described in Formula (XII):

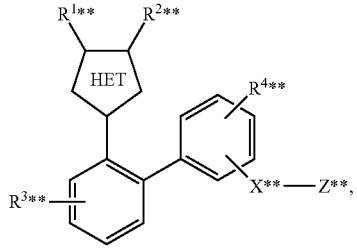

Formula XII its stereoisomers, a pharmaceutically acceptable salt or prodrug ester thereof.

wherein $R^{1}$ and $R^{2}$ are the same or different and are independently selected from, alkyl, cycloalkyl, cycloalkenyl, aryl, aralkyl, or;

$R^{3**}$ is selected from hydrogen, halogen, alkyl, alkenyl, alkynyl, alkoxy, cycloalkyl, cycloalkylalkyl, cycloalkenyl, alkylcarbonyl, cycloalkenylalkyl, haloalkyl, polyhaloalkyl, cyano, nitro, hydroxy, amino, alkanoyl, alkylthio, alkylsulfonyl, alkoxycarbonyl, alkylaminocarbonyl, alkylcarbonylamino, alkylcarbonyloxy, alkylaminosulfonyl, alkylamino, dialkylamino, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkoxycarbonylamino, alkylsulfonyl, aminosulfinyl, aniinosulfonyl, alkylsulfinyl, sulfonamido or sulfonyl;

$R^{4**}$ is selected from hydrogen, halogen, alkyl, alkenyl, alkynyl, alkoxy, aryl, arylalkyl, arylalkenyl, arylalkynyl, cycloalkyl, cycloalkylalkyl, polycycloalkyl, polycycloalkylaikyl. cycloalkenyl, cycloalkynyl, alkylcarbonyl, arylcarbonyl, cycloheteroalkyl, cycloheteroalkylalkyl, cycloalkenylalkyl, polycycloalkenyl, polycycloalkenylalkyl, polycycloalkynyl, polycycloalkynylalkyl, haloalkyl, polyhaloalkyl, cyano, nitro, hydroxy, amino, alkanoyl, aroyl, alkylsulfonyl, arylsulfonyl, alkoxycarbonyl, aryloxycarbonyl, alkylaminocarbonyl, arylaminocarbonyl, alkylcarbonylamino, alkoxycarbonyloxy, alkylaminosulfonyl, arylaminosulfonyl, alkylamino, dialkylamino, all optionally substituted through available carbon atoms with 1, 2, 3, 4 or 5 groups selected from hydrogen, halo, haloalkyl, polyhaloalkyl, alkoxy, haloalkoxy, polyhaloalkoxy, alkoxycarbonyl, alkenyl, alkynyl, cycloalkyl, cycloalkylalkyl, aryl, arylalkyl, arylcycloalkyl, arylalkenyl, arylalkynyl, aryloxy, aryloxyalkyl, arylalkoxy, arylazo, hydroxy, hydroxyalkyl, nitro, cyano, amino, substituted amino, alkylamino, dialkylamino, thiol, alkyltbio, arylthio, arylthioalkyl, alkylcarbonyl, arylcarbonyl, acyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, alkoxycarbonylamino, arylsulfinyl, arylsulfmylalkyl, arylsulfonyl, alkylsulfonyl, aminosulfinyl, aminosulfonyl, arylsulfonylamino, alkylsulfinyl, sulfonamido or sulfonyl;

$X^{}$ is a bond or a linker group selected from $(CH_2)»$, $O(CH_2)$, $S(CH_2)»$, cycloalkylene, $N(R^{5})(CH;)»$, NHCO, or CH=CH where n=0-5 and R' is hydrogen, alkyl, or alkanoyl;

$Z^{**}$ is $CO_2H$ or tetrazole of the formula

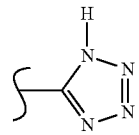

or its tautomer; and the group

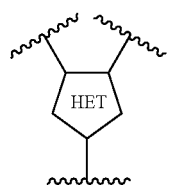 [SMILES: *C1CC(*)C(*)C1]

represents a heteroaryl group of the formula

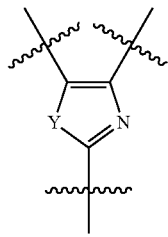

where Y is NR *** or O;
which may further be optionally substituted with one or two groups, which may be the same or different and are independently selected from alkyl, alkenyl, hydroxyalkyl, keto, carboxyalkyl, carboxy, cycloalkyl, alkoxy, formyl, alkanoyl, alkoxyalkyl or alkoxycarbonyl,
with the provisos that
(1) n≠o when Z is CO$_2$H and X is O(CH))), S(CH$_2$)n or N(R$^5$)(CH$_2$)$_n$); and
(2) when

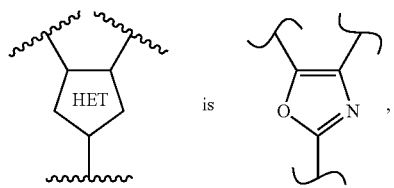

then X-Z may not be O-lower alkylene-CO$_2$H or —O— lower alkylene-CO$_2$alkyl when R$^{1}$ and R$^{2}$ are both aryl or substituted aryl and R$^{2}$ and R$^{4}$ are each hydrogen.

It is an object of the present invention to utilize the compounds described herein in the prophylaxis or treatment of viral disorders by acting on the fatty acid binding protein (FABP4), such as common cold, SARS, and COVID-19.

Yet another object of the present invention is a pharmaceutical composition comprising a compounds herein as active ingredient, in combination with a pharmaceutically acceptable diluent or carrier for use in the treatment of viral disorders by acting on FABP4. Here, the pharmaceutical composition can further comprise an additional therapeutically active agent.

Yet another object of the present invention is a method for the treatment of viral disorders by acting on the FABP4, which comprises administering to a subject in need of such treatment (preferably, a human) an effective amount of the compounds herein, including, optionally, the co-administration with other therapeutic agents, either as a single (or multiple) dosing, and either simultaneously or sequentially.

Any compound disclosed herein which is a pure optical isomer.

Any compound disclosed herein which is the (+)-isomer.

Definitions

As used herein, the term "acid isostere" includes, but is not limited to, the following functional groups where R is an alkyl group:

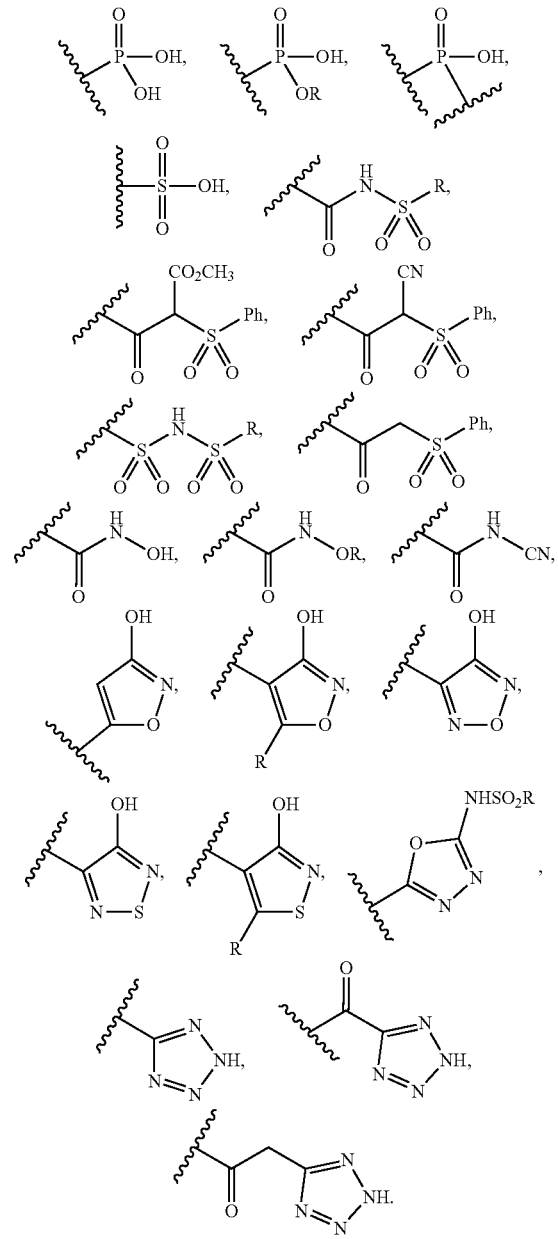

The term "alkyl" refers to a saturated, straight- or branched-chain hydrocarbon group having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylenyl" refers to a divalent alkyl group.

The term "alkoxy" as used herein includes —O-(alkyl), wherein alkyl is defined above.

The term "amino" as used herein refers to an —NH$_2$ group.

"Aryl" means a mono-, bi-, or tricyclic aromatic group, wherein all rings of the group are aromatic and all ring atoms are carbon atoms. For bi- or tricyclic systems, the individual aromatic rings are fused to one another. Examples of aryl groups are 6 and 10 membered aryls. Further examples of aryl groups include, but are not limited to, phenyl, naphthalene, and anthracene.

The term "cyano" as used herein means a substituent having a carbon atom joined to a nitrogen atom by a triple bond.

The term "deuterium" as used herein means a stable isotope of hydrogen having one proton and one neutron.

The term "halo" represents chloro, fluoro, bromo, or iodo. In some embodiments, halo is chloro, fluoro, or bromo. The term "halogen" as used herein refers to fluorine, chlorine, bromine, or iodine.

The term "hydroxy" means an —OH group.

The term "oxo" means an —O group and may be attached to a carbon atom or a sulfur atom.

The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 15 carbon ring atoms. A non-limiting category of cycloalkyl groups are saturated or partially saturated, monocyclic carbocycles having from 3 to 6 carbon atoms. Illustrative examples of cycloalkyl groups include, but are not limited to, the following moieties:

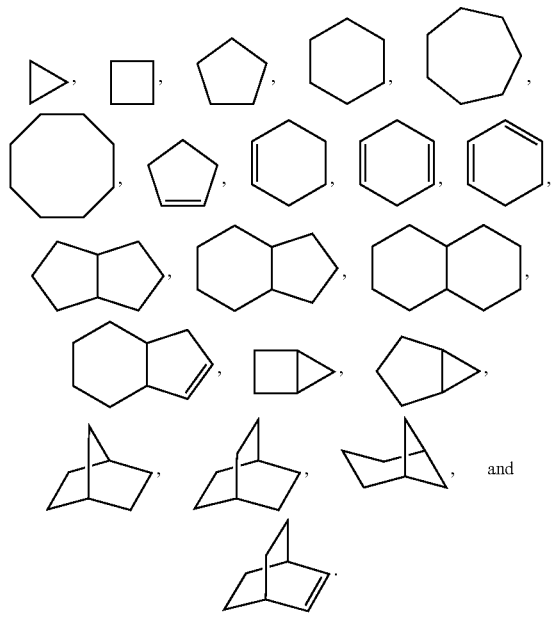

"Heterocycloalkyl" as used herein refers to a monocyclic, or fused, bridged, or spiro polycyclic ring structure that is saturated or partially saturated and has from three to 12 ring atoms selected from carbon atoms and up to three heteroatoms selected from nitrogen, oxygen, and sulfur. The ring structure may optionally contain up to two oxo groups on carbon or sulfur ring members, or an N-oxide. Illustrative heterocycloalkyl entities include, but are not limited to:

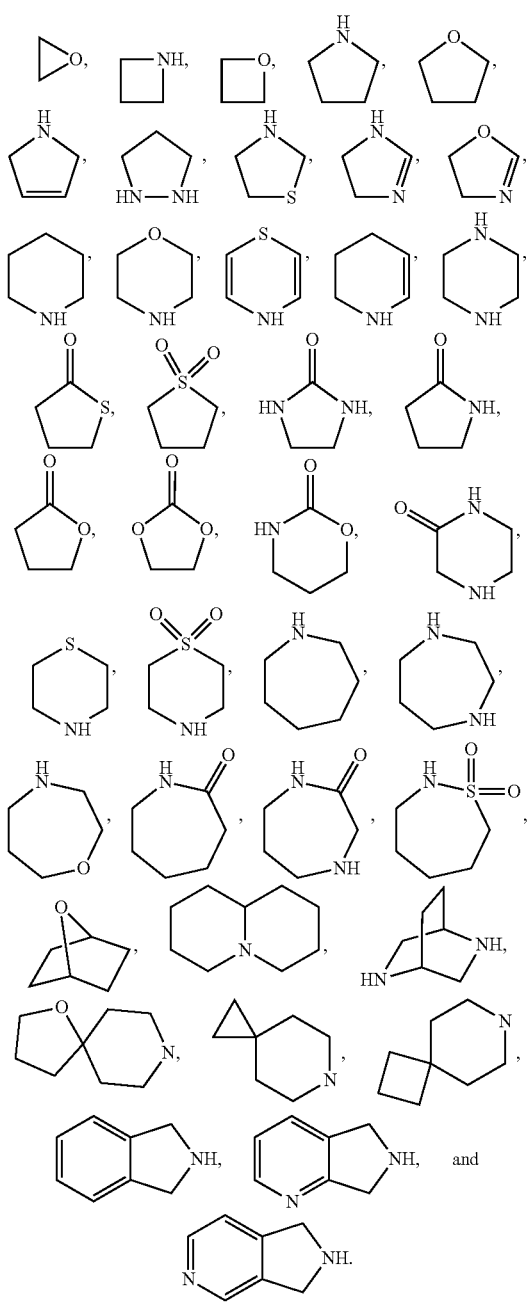

As used herein, the term "heteroaryl" refers to a monocyclic, or fused polycyclic, aromatic heterocycle having from three to 15 ring atoms that are selected from carbon, oxygen, nitrogen, and sulfur. Suitable heteroaryl groups do not include ring systems that must be charged to be aromatic, such as pyrylium. Suitable 5-membered heteroaryl rings (as a monocyclic heteroaryl or as part of a polycyclic heteroaryl) have one oxygen, sulfur, or nitrogen ring atom, or one nitrogen plus one oxygen or sulfur, or 2, 3, or 4 nitrogen ring atoms. Suitable 6-membered heteroaryl rings (as a monocyclic heteroaryl or as part of a polycyclic heteroaryl) have 1, 2, or 3 nitrogen ring atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "bicyclic heteroaryl" refers to a heteroaryl as defined above, having two constituent aromatic rings, wherein the two rings are fused to one another and at least one of the rings is a heteroaryl as defined above. Bicyclic heteroaryls include bicyclic heteroaryl groups comprising 1, 2, 3, or 4 heteroatom ring atoms selected from O, N or S. In certain embodiments, wherein the heteroatom is N it can be an N-oxide. Bicyclic heteroaryls also include 8-, 9-, or 10-membered bicyclic heteroaryl groups. Bicyclic heteroaryls also include 8-, 9-, or 10-membered bicyclic heteroaryl groups that have 1, 2, 3, or 4 heteroatom ring atoms selected from O, N or S. Illustrative examples of bicyclic heteroaryls include, but are not limited to:

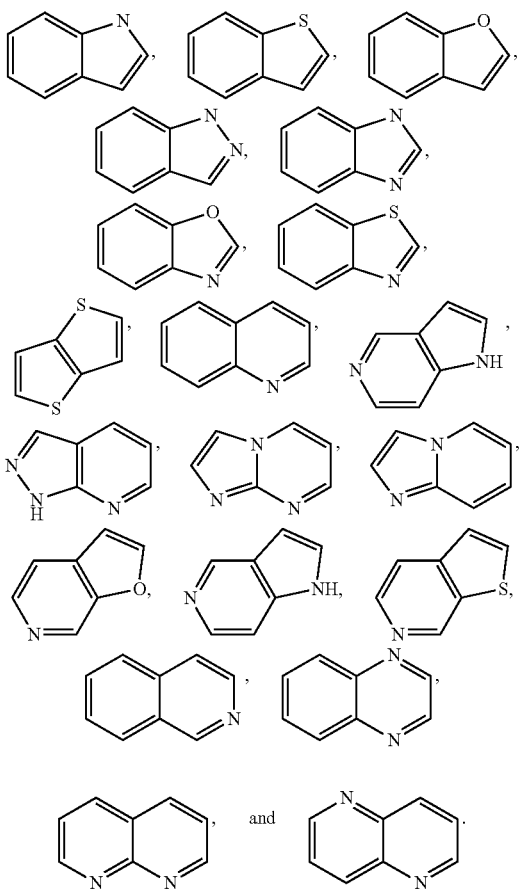

Those skilled in the art will recognize that the species of heteroaryl, cycloalkyl, and heterocycloalkyl groups listed or illustrated above are not exhaustive, and that additional species within the scope of these defined terms may also be selected.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl or Ra) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the remainder of the formula can be at any point on the multifunctional moiety. In some embodiments, the point of attachment is indicated by a line or hyphen. For example, aryloxy—refers to a moiety in which an oxygen atom is the point of attachment to the core molecule while aryl is attached to the oxygen atom.

Additional Definitions

As used herein, "proton nuclear magnetic resonance" or 1H NMR is the application of nuclear magnetic resonance in NMR spectroscopy with respect to hydrogen-1 nuclei within the molecules of a substance, in order to determine the structure of its molecules.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given enzyme or protein.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

Additional Chemical Descriptions

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column. The chiral centers of compounds of the present invention may be designated as "R" or "S" as defined by the IUPAC 1974 Recommendations.

The compounds of the invention can form pharmaceutically acceptable salts, which are also within the scope of this invention. A "pharmaceutically acceptable salt" refers to a salt of a free acid or base of a compound of the invention that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al., Camille G. (eds.) Handbook of Pharmaceutical Salts: Properties, Selection and Use. (2002) Zurich: Wiley-VCH; S. Berge et al., J. Pharm. Sci. (1977) 66(1) 1-19; P. Gould, Int. J. Pharm. (1986) 33 201-217; Anderson et al., The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., J. Pharm. Sci., 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al., AAPS PharmSciTech., 5(1), article 12 (2004); and A. L. Bingham et al., Chem. Commun., 603-604 (2001). A typical, non-limiting process involves dissolving the inventive compound in a suitable amounts of the solvent (organic solvent or water or a mixture thereof) at a higher than ambient temperature, and cooling the solution at a rate sufficient to form crystals which are then isolated by standard methods. Analytical techniques such as, for example, infrared spectroscopy, show the presence of the solvent (or water) in the crystals as a solvate (or hydrate).

The invention also relates to pharmaceutically acceptable prodrugs of the compounds of the invention, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of the invention). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985.

Examples of prodrugs include pharmaceutically acceptable esters of the compounds of the invention, which are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, $C_{1-4}$alkoxy, or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol. Additional discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press.

For example, if a compound of the invention contains a carboxylic acid functional group, a prodrug can comprise an ester formed by the replacement of the hydrogen atom of the acid group with a group such as, for example, $(C_1$-$C_8)$alkyl, $(C_2$-$C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$—$C_3)$alkyl (such as ß-dimethylaminoethyl), carbamoyl-$(C_1$-$C_2)$alkyl, N,N-di$(C_1$—$C_2)$alkylcarbamoyl-$(C_1$-$C_2)$alkyl and piperidino-, pyrrolidino- or morpholine $(C_2$-$C_3)$alkyl, and the like.

Similarly, if a compound of the invention contains an alcohol functional group, a prodrug can be formed by the replacement of the hydrogen atom of the alcohol group with a group such as, for example, $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$ alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1$-$C_6)$alkyl)$_2$ or glycosyl (the radical resulting from the removal of a hydroxyl group of the hemiacetal form of a carbohydrate), and the like.

If a compound of the invention incorporates an amine functional group, a prodrug can be formed by the replacement of a hydrogen atom in the amine group with a group such as, for example, R"-carbonyl, R"O-carbonyl, NR"R'-carbonyl where R" and R' are each independently $(C_1$-$C_{10})$ alkyl, $(C_3$-$C_7)$ cycloalkyl, benzyl, or R"-carbonyl is a natural α-aminoacyl or natural α-aminoacyl, —C(OH)C(O)OY$^1$ wherein Y$_1$ is H, $(C_1$-$C_6)$alkyl or benzyl, —C(OY$^2$)Y$_3$ wherein Y$_2$ is $(C_1$-$C_4)$ alkyl and Y$_3$ is $(C_1$-$C_6)$alkyl, carboxy $(C_1$-$C_6)$alkyl, amino$(C_1$-$C_4)$alkyl or mono-N- or di-N, N—$(C_1$-$C_6)$alkylaminoalkyl, —C(Y+)Y$_5$ wherein Y+ is H or methyl and Y$_5$ is mono-N- or di-N,N-$(C_1$-$C_6)$alkylamino morpholino, piperidin-1-yl or pyrrolidin-1-yl, and the like.

The present invention also relates to pharmaceutically active metabolites of compounds of the invention, and uses of such metabolites in the methods of the invention. A "pharmaceutically active metabolite" means a pharmacologically active product of metabolism in the body of a compound of the invention or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as 2H, 3H, 11C, 13C, 14C, 15N, 18O, 17O, 31p, 32P, 35S, 18F, 36Cl, and 125I, respectively. Such isotopically labelled compounds are useful in metabolic studies (for example with 1+C), reaction kinetic studies (with, for example 2H or 3H), detection or imaging techniques [such as positron emission tomography (PET) or single-photon emission computed tomography (SPECT)] including drug or substrate tissue distribution assays, or in radioactive treatment of patients. In particular, an 18F or 11C labeled compound may be particularly suitable for PET or SPECT studies. Further, substitution with heavier isotopes such as deuterium (i.e., 2H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," "prodrug," and the like, with respect to the compounds described herein is intended to apply equally to the salt, solvate, polymorph, and prodrug forms of enantiomers, stereoisomers, rotamers, tautomers, atropisomers, and racemates of the inventive compounds.

In other embodiments the invention is a method for treating a viral disease in a subject comprising administering to said subject a therapeutically effective dose of one or more of the compounds selected from the group consisting of: 5-[(3-cyanophenyl)methyl]-2-fluoro-7-hexyl-5H,6H,7H,8H,9H, 10H-cyclohepta[b]indole-4-carboxylic acid, 5-[(6-cyanopyridin-2-yl)methyl]-7-hexyl-5H,6H, 7H,8H,9H, 10H-cyclohepta[b]indole-4-carboxylic acid, 5-[(6-carbamoylpyridin-2-yl)methyl]-7-hexyl-5H,6H, 7H, 8H,9H, 10H-cyclohepta[b]indole-4-carboxylic acid, 6-({4-carboxy-7-hexyl-5H,6H, 7H, 8H,9H, 10H-cyclohepta[b]indol-5-yl}methyl)pyridine-2-carboxylic acid, 5-[(3-cyano-2-fluorophenyl)methyl]-7-hexyl-5H,6H,7H,8H,9H,10H-cyclohepta[b]indole-4-carboxylic acid, 5-[(1,3-benzoxazol-6-yl)methyl]-7-hexyl-5H,6H, 7H,8H,9H, 10H-cyclohepta[b]indole-4-carboxylic acid, 5-[(1,3-benzoxazol-5-yl)methyl]-7-hexyl-5H,6H,7H,8H,9H, 10H-cyclohepta[b]indole-4-carboxylic acid, 5-[(6-fluoropyridin-2-yl)methyl]-7-hexyl-5H,6H, 7H, 8H,9H, 10H-cyclohepta[b]indole-4-carboxylic acid, 5-[(2-fluoropyridin-4-yl)methyl]-7-hexyl-5H,6H, 7H,8H,9H, 10H-cyclohepta[b]indole-4-carboxylic acid, 7-hexyl-5-{[6-(trifluoromethyl)pyridin-2-yl]methyl}-5H, 6H,7H,8H,9H, 10H-cyclohepta[b]indole-4-carboxylic acid, 7-hexyl-5-{[2-(trifluoromethyl)pyridin-4-yl]methyl}-5H, 6H,7H,8H,9H, 10H-cyclohepta[b]indole-4-carboxylic acid, 5-[(5-cyanopyridin-3-yl)methyl]-7-hexyl-5H,6H, 7H, 8H,9H, 10H-cyclohepta[b]indole-4-carboxylic acid, 5-[(5-cyanothiophen-2-yl)methyl]-7-hexyl-5H,6H,7H,8H,9H, 10H-cyclohepta[b]indole-4-carboxylic acid, 5-[(4-cyanothiophen-2-yl)methyl]-7-hexyl-5H,6H,7H,8H,9H, 10H-cyclohepta[b]indole-4-carboxylic acid, 5-[(5-cyanofuran-2-yl)methyl]-7-hexyl-5H,6H,7H,8H,9H, 10H-cyclohepta[b]indole-4-carboxylic acid, 5-[(3,5-dimethyl-1,2-oxazol-4-yl)methyl]-7-hexyl-5H,6H,7H,8H,9H, 10H-cyclohepta[b]indole-4-carboxylic acid, 5-(3-cyanobenzoyl)-7-hexyl-5H, 6H,7H,8H,9H, 10H-cyclohepta[b]indole-4-carboxylic acid, 5-[(1,3-benzoxazol-7-yl)methyl]-7-hexyl-5H,6H, 7H, 8H,9H, 10H-cyclohepta[b]indole-4-carboxylic acid, 5-[(5-cyanothiophen-3-yl)methyl]-7-hexyl-5H,6H,7H,8H,9H, 10H-cyclohepta[b]indole-4-carboxylic acid, 7-hexyl-5-[(1H-indol-4-yl)methyl]-5H,6H,7H,8H,9H, 10H-cyclohepta[b]indole-4-carboxylic acid, 5-[(3-carbamoylphenyl)methyl]-7-propyl-5H,6H,7H,8H,9H,10H-cyclohepta[b]indole-4-carboxylic acid, 7-butyl-5-[(3-carbamoylphenyl)methyl]-5H,6H,7H,8H,9H, 10H-cyclohepta[b]indole-4-carboxylic acid, 7-butyl-5-[(3-cyanophenyl)methyl]-5H,6H, 7H,8H,9H, 10H-cyclohepta[b]indole-4-carboxylic acid, 7-butyl-5-[(pyridin-3-yl)methyl]-5H,6H,7H,8H,9H, 10H-cyclohepta[b]indole-4-carboxylic acid, 7-butyl-5-[(3-methylphenyl)methyl]-5H,6H,7H,8H,9H, 10H-cyclohepta[b]indole-4-carboxylic acid, 7-butyl-5-[(3-methoxyphenyl)methyl]-5H,6H, 7H, 8H,9H, 10H-cyclohepta[b]indole-4-carboxylic acid, 7-butyl-5-[(3-chlorophenyl)methyl]-5H, 6H,7H,8H,9H, 10H-cyclohepta[b]indole-4-carboxylic acid, 7-butyl-5-[(3-hydroxyphenyl)methyl]-5H,6H,7H,8H,9H, 10H-cyclohepta[b]indole-4-carboxylic acid, 7-butyl-5-[(2-methoxypyridin-4-yl)methyl]-5H,6H,7H,8H,9H, 10H-cyclohepta[b]indole-4-carboxylic acid, 7-butyl-5-[(4-carbamoylphenyl)methyl]-5H,6H,7H,8H,9H,10H-cyclohepta[b]indole-4-carboxylic acid, 7-butyl-5-[(2-carbamoylphenyl)methyl]-5H,6H, 7H, 8H,9H, 10H-cyclohepta[b]indole-4-carboxylic acid, 7-butyl-5-[(4-methylphenyl)methyl]-5H, 6H,7H,8H,9H,10H-cyclohepta[b]indole-4-carboxylic acid, 7-butyl-5-[(2-cyanophenyl)methyl]-5H,6H,7H,8H,9H, 10H-cyclohepta[b]indole-4-carboxylic acid, 7-butyl-5-[(2-methylphenyl)methyl]-5H,6H, 7H,8H,9H, 10H-cyclohepta[b]indole-4-carboxylic acid, 7-butyl-5-[(2-fluorophenyl)methyl]-5H,6H,7H,8H,9H, 10H-cyclohepta[b]indole-4-carboxylic acid, 5-[(3-carbamoylphenyl)methyl]-7-pentyl-5H,6H,7H, 8H,9H, 10H-cyclohepta[b]indole-4-carboxylic acid, 5-[(3-cyanophenyl)methyl]-7-pentyl-5H,6H,7H,8H,9H,10H-cyclohepta[b]indole-4-carboxylic acid, 5-[(3-carbamoylphenyl)methyl]-7-(2-phenylethyl)-5H,6H, 7H, 8H,9H, 10H-cyclohepta[b]indole-4-carboxylic acid, 5-[(3-cyanophenyl)methyl]-7-(2-phenylethyl)-5H,6H,7H,8H,9H, 10H-cyclohepta[b]indole-4-carboxylic acid, 5-[(3-carbamoylphenyl)methyl]-7-hexyl-5H,6H,7H,8H,9H, 10H-cyclohepta[b]indole-4-carboxylic acid, 5-[(3-cyanophenyl)methyl]-7-hexyl-5H,6H,7H,8H,9H, 10H-cyclohepta[b]indole-4-carboxylic acid, 5-[(3-carbamoylphenyl)methyl]-7-octyl-5H,6H,7H,8H,9H,10H-cyclohepta[b]indole-4-carboxylic acid, 5-[(3-cyanophenyl)methyl]-7-octyl-5H,6H, 7H, 8H,9H, 10H-cyclohepta[b]indole-4-carboxylic acid, 5-[(3-fluorophenyl)methyl]-7-hexyl-5H,6H, 7H,8H,9H, 10H-cyclohepta[b]indole-4-carboxylic acid, 7-hexyl-5-[(pyridin-3-yl)methyl]-5H,6H,7H,8H,9H, 10H-cyclohepta[b]indole-4-carboxylic acid, 7-hexyl-5-[(3-methylphenyl)methyl]-5H,6H,7H,8H,9H, 10H-cyclohepta[b]indole-4-carboxylic acid, 7-hexyl-5-[(3-methoxyphenyl)methyl]-5H, 6H,7H,8H,9H, 10H-cyclohepta[b]indole-4-carboxylic acid, 5-[(3-chlorophenyl)methyl]-7-hexyl-5H,6H,7H,8H,9H, 10H-cyclohepta[b]indole-4-carboxylic acid, 7-hexyl-5-[(2-methoxypyridin-4-yl)methyl]-5H,6H,7H,8H,9H, 10H-cyclohepta[b]indole-4-carboxylic acid, 5-[(3-carboxyphenyl)methyl]-7-hexyl-5H,6H, 7H,8H,9H, 10H-cyclohepta[b]indole-4-carboxylic acid, 5-[(4-carbamoylphenyl)methyl]-7-hexyl-5H,6H, 7H, 8H,9H, 10H-cyclohepta[b]indole-4-carboxylic acid, 5-[(2-carbamoylphenyl)methyl]-7-hexyl-5H,6H, 7H, 8H,9H, 10H-cyclohepta[b]indole-4-carboxylic acid, 7-hexyl-5-[(4-methylphenyl)methyl]-5H,6H,7H,8H, 9H,10H-cyclohepta[b]indole-4-carboxylic acid, 5-[(4-cyanophenyl)methyl]-7-hexyl-5H,6H,7H,8H,9H, 10H-cyclohepta[b]indole-4-carboxylic acid, 5-[(2-cyanophenyl)methyl]-7-hexyl-5H,6H,7H,8H,9H,10H-cyclohepta[b]indole-4-carboxylic acid, 7-hexyl-5-[(2-methylphenyl)methyl]-5H,6H,7H,8H,9H, 10H-cyclohepta[b]indole-4-carboxylic acid, 5-[(2-fluorophenyl)methyl]-7-hexyl-5H, 6H,7H,8H,9H, 10H-cyclohepta[b]indole-4-carboxylic acid, 5-[(4-fluorophenyl)methyl]-7-hexyl-5H,6H,7H,8H,9H, 10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H, 10H-cyclohepta[b]indole-4-carboxylic acid, 6-butyl-5-[(3-cyanophenyl)methyl]-5H,6H, 7H,8H,9H, 10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3-ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H,10H-cyclohepta[b]indole-4-carboxylic acid, 5-[(3-cyanophenyl)methyl]-10-ethyl-5H,6H,7H,8H,9H,10H-cyclohepta[b]indole-4-carboxylic acid, 5-[(3-carbamoylphenyl)methyl]-10-propyl-5H,6H,7H,8H,9H, 10H-cyclohepta[b]indole-4-carboxylic acid, 5-[(3-cyanophenyl)methyl]-10-propyl-5H, 6H, 7H, 8H,9H, 10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H,10H-cyclohepta[b]indole-4-carboxylic acid, 10-butyl-5-[(3-cyanophenyl)methyl]-5H, 6H,7H,8H,9H, 10H-cyclohepta[b]indole-4-carboxylic acid, 5-[(3-carbamoylphenyl)methyl]-10-pentyl-5H,6H,7H,8H, 9H, 10H-cyclohepta[b]indole-4-carboxylic acid, 5-[(3-cyanophenyl)methyl]-10-pentyl-5H,6H,7H,8H,9H, 10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3-carbamoylphenyl)methyl]-7-ethyl-5H,6H, 7H, 8H,9H, 10H-cyclohepta[b]indole-4-carboxylic acid, 5-[(3-cyanophenyl)methyl]-7-ethyl-5H,6H, 7H,8H,9H, 10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H, 10H-cyclohepta[b]indol-4-yl}formamido)acetic acid, 2-({7-butyl-5-[(3-cyanophenyl)methyl]-5H,6H,7H,8H,9H,10H-cyclohepta[b]indol-4-yl}formamido)acetic acid, 7-butyl-5-[(3-carbamoylphenyl)methyl]-N-(2-hydroxyethyl)-5H,6H, 7H, 8H,9H, 10H-cyclohepta[b]indole-4-carboxamide, 7-butyl-5-[(3-cyanophenyl)methyl]—N-(2-hydroxyethyl)-5H,6H,7H, 8H,9H, 10H-cyclohepta[b]indole-4-carboxamide, 7-butyl-5-[(3- fluorophenyl)methyl]-5H,6H,7H,8H,9H, 10H-cyclohepta[b]indole-4-carboxylic acid, and 7-butyl-5-[(3-carboxyphenyl)methyl]-5H,6H,7H,8H,9H, 10H-cyclohepta[b]indole-4-carboxylic acid, or pharmaceutically acceptable salts or stereoisomers thereof.

Yet in other embodiments the invention is a method for treating a viral disease in a subject comprising administering to said subject a therapeutically effective dose of a compound selected from the group consisting of: 2-((2'-(5-Ethyl-3,4-diphenyl-1H-pyrazol-1-yl)-[1,1'-biphenyl]-3-yl)oxy) acetic acid, 6-chloro-4-phenyl-2-(piperidin-1-yl)-3-(1H-tetrazol-5-yl)quinoline, 5-((3-chloro-2-methylphenoxy)methyl)-2-phenyl-[1,2,4]triazolo[1,5-a]pyrimidin-7(4H)-one, and 3-(5-cyclopropyl-3-(3,5-dimethyl-1H-pyrazol-4-yl)-2-(3-isopropoxyphenyl)-1H-indol-1-yl)propanoic acid, or pharmaceutically acceptable salts or stereoisomers thereof. It should be appreciated that WO 00/59506, U.S. 2013/0116234 A1, WO 2010/056631, PCT/US21/39470, U.S. 2013/0116231 A1, Sulsky et al., Bioorg Med Chem Lett. 2007 Jun. 15; 17(12):3511-5. doi: 10.1016/j.bmcl.2006.12.044. Epub 2006 Dec 21, Kuhne et al., Bioorg Med Chem Lett. 2016 Oct. 15; 26(20):5092-5097. doi: 10.1016/j.bmcl.2016.08.071. Epub 2016 Aug 22.), and Lan et al., J Lipid Res. 2011 April; 52(4):646-56. doi: 10.1194/jlr.M012757. Epub 2011 Feb 4.), Tagami et al., ACS Med Chem Lett. 2016 Apr. 14; 7(4): 435-439. doi: 10.1021/acsmedchemlett.6b00040) are hereby incorporated by reference in their entirety.

It is an object of the present invention to utilize the compounds described herein in the treatment of viral disorders by acting on the fatty acid binding protein (FABP4).

Yet another object of the present invention is a pharmaceutical composition comprising a compounds herein as active ingredient, in combination with a pharmaceutically acceptable diluent or carrier for use in the treatment of viral disorders by acting on FABP4. Here, the pharmaceutical composition can further comprise an additional therapeutically active agent.

Yet another object of the present invention is a method for the treatment of viral disorders by acting on the FABP4, which comprises administering to a subject in need of such treatment (preferably, a human) an effective amount of the compounds herein, including, optionally, the co-administration with other therapeutic agents, either as a single (or multiple) dosing, and either simultaneously or sequentially.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The compositions and formulations of the invention can be administered as sterile compositions and sterile formulations. Sterile pharmaceutical formulations are compounded or manufactured according to pharmaceutical-grade sterilization standards (e.g., United States Pharmacopeia Chapters 797, 1072, and 1211; California Business & Professions Code 4127.7; 16 California Code of Regulations 1751, 21 Code of Federal Regulations 21, or ex-U.S. counterparts to such regulations) known to those of skill in the art.

Liquid form preparations include solutions, suspensions and emulsions. As an example, may be mentioned water or water-propylene glycol solutions for parenteral injection or addition of sweeteners and opacifiers for oral solutions, suspensions, and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Methods of delivering drugs by pulmonary administration have been described. For example, each of U.S. Pat. Nos. 6,550,472, 6,546,927, 6,543,443, 6,540,154, 6,540,153, 6,467,476, 6,427,682, 6,503,480, 6,447,753, 6,387,390, 5,985,320, 5,985,309, 5,855,913, 6,431,167, 6,408,854, 6,349,719, 6,167,880, 6,098,620, 5,971,951, 5,957,124, 5,906,202, 5,819,726, 5,755,218, 5,522,385, 6,546,929, 6,543,448, 6,509,006, 6,423,344, 6,303,582, and 6,138,668 teaches methods and devices useful in the pulmonary administration of drugs and/or nasal instillation. Bioadhesives have been described for facilitating transport of medicaments across endothelial mucosa. For example, U.S. Pat. No. 6,228,383 teaches use of bioadhesive fatty acid esters for facilitating transport of drug substances across mucosa in the lung, nose and other tissues. Penetration enhancers have been described in, for example, U.S. patent application Ser. No. 09/315,298, filed on May 20, 1999. Penetration enhancers facilitate the penetration of mucosa, including pulmonary and nasal mucosa. The present invention provides, inter alia, compositions formulated for pulmonary or nasal administration of antiviral compounds, especially compounds capable of attenuating, mitigating or preventing viral infections, and especially coronavirus. In some embodiments of the invention, viral infections are treated by administering an antiviral compound of the present invention to a patient in need thereof. In some embodiments of the invention, viral infection is treated by administering an antiviral small molecule to a patient in need thereof. In some embodiments according to the present invention, an antiviral agent is administered by pulmonary or intranasal means to a patient in need thereof. In certain embodiments, the antiviral agent is a compound of the invention. In other embodiments of the invention, the antiviral agent is a mixture of antiviral compounds. In certain embodiments, the invention comprises a molecule of the invention in combination therapy, for example with one or more additional antiviral agents. In some embodiments of the present invention, the inventive composition comprises, in addition to one or more antiviral agents, a therapeutically acceptable agent for intrapulmonary or intranasal administration.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

The compound can be administered orally or intravenously.

The pharmaceutical preparation can be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, for example from about 1 mg to about 500 mg, in particular from about 1 mg to about 250 mg, or from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Treatment or Prevention of Viral Infection

The compounds of the invention are useful in human and veterinary medicine for treating or preventing a viral infection in a patient. In one embodiment, the compounds of the invention are inhibitors of viral replication. In another embodiment, the compounds of the invention can be inhibitors of influenza, rhinovirus or coronavirus replication. Accordingly, the compounds of the invention are useful for treating viral infections, such as coronavirus. In accordance with the invention, the compounds of the invention can be administered to a patient in need of treatment or prevention of a viral infection.

Accordingly, in one embodiment, the invention provides methods for treating a viral infection in a patient comprising administering to the patient an effective amount of at least one compounds of the invention or a pharmaceutically acceptable salt thereof.

The compounds of the invention are useful in the inhibition of viruses, the treatment of viral infection and/or reduction of the likelihood or severity of symptoms of viral infection and the inhibition of viral replication and/or viral production in a cell-based system. For example, the compounds of the invention are useful in treating infection by viruses after suspected past exposure to viruses by such means as airborne transmission, blood transfusion, exchange of body fluids, etc. In one embodiment, the viral infection is acute respiratory viral infection. In another embodiment, the viral infection is chronic viral infection.

Accordingly, in one embodiment, the invention provides methods for treating viral infection in a patient, the methods comprising administering to the patient an effective amount of at least one the invention or a pharmaceutically acceptable salt thereof. In a specific embodiment, the amount administered is effective to treat or prevent a viral infection in a patient. In another specific embodiment, the amount administered is effective to inhibit viral replication and/or viral production in the patient.

In particular embodiments, the viral infection is caused by influenza, coronavirus, rhinovirus, respiratory syncytial viruses (RSVs), parainfluenza, adenoviruses, Human metapneumovirus (HMPV) or Human Bocavirus (HBoV).

Combination Therapy

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In another embodiment, the present methods for treating or preventing viral infection can further comprise the administration of one or more additional therapeutic agents.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: a compound of the invention or a pharmaceutically acceptable salt thereof, and (ii) at least one additional therapeutic agent that is other than a compound of the invention, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of the invention and an additional therapeutic agent may be present in fixed amounts (dosage amounts) in a single dosage unit (e.g., a capsule, a tablet and the like).

In one embodiment, the at least one a compound of the invention is administered during a time when the additional therapeutic agent(s) exert their prophylactic or therapeutic effect, or vice versa.

In another embodiment, the at least one a compound of the invention and the additional therapeutic agent(s) are administered in doses commonly employed when such agents are used as monotherapy for treating a viral infection.

In another embodiment, the at least one a compound of the invention and the additional therapeutic agent(s) are administered in doses lower than the doses commonly employed when such agents are used as monotherapy for treating a viral infection.

In still another embodiment, the at least one a compound of the invention and the additional therapeutic agent(s) act synergistically and are administered in doses lower than the doses commonly employed when such agents are used as monotherapy for treating a viral infection.

In one embodiment, the at least one a compound of the invention and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

The at least one a compound of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one compound of the invention and the additional therapeutic agent(s) may inhibit the resistance of a viral infection to these agents.

Non-limiting examples of additional therapeutic agents useful in the present combination therapy compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the Compounds of the invention are in substantially purified form.

Other embodiments of the present invention include the following:

(a) A pharmaceutical composition comprising an effective amount of a compound of the invention or a pharmaceutically acceptable salt thereof, and a pharmaceutically acceptable carrier.
(b) The pharmaceutical composition of (a), further comprising a second therapeutic agent selected from the group consisting of antiviral agents, immunomodulators, and anti-infective agents.
(c) The pharmaceutical composition of (b), wherein the antiviral agent is an antiviral selected from the group consisting of protease inhibitors, polymerase inhibitors and other viral inhibitors.
(d) A pharmaceutical combination that is (i) a compound of the invention and (ii) a second therapeutic agent selected from the group consisting of antiviral agents, immunomodulators, and anti-infective agents; wherein the compound of the invention and the second therapeutic agent are each employed in an amount that renders the combination effective for inhibiting viral replication or disease, or for treating viral infection and/or reducing the likelihood or severity of symptoms of viral infection.
(e) The combination of (d), wherein the antiviral agent is an antiviral selected from the group consisting of protease inhibitors, polymerase inhibitors and other viral inhibitors.
(f) A method of inhibiting viral replication in a subject in need thereof which comprises administering to the subject an effective amount of a compound of the invention.
(g) A method of treating viral infection and/or reducing the likelihood or severity of symptoms of viral infection in a subject in need thereof which comprises administering to the subject an effective amount of a compound of the invention).
(h) The method of (g), wherein the compound of the invention is administered in combination with an effective amount of at least one second therapeutic agent selected from the group consisting of antiviral agents, immunomodulators, and anti-infective agents.
(i) The method of (h), wherein the antiviral agent is an antiviral selected from the group consisting of protease inhibitors, polymerase inhibitors and other viral inhibitors.
(j) A method of inhibiting viral replication in a subject in need thereof which comprises administering to the subject the pharmaceutical composition of (a), (b) or (c) or the combination of (d) or (e).
(k) A method of treating viral infection and/or reducing the likelihood or severity of symptoms of viral infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting viral replication or (c) treating viral infection and/or reducing the likelihood or severity of symptoms of viral infection. In these uses, the compounds of the present invention can optionally be employed in combination with one or more second therapeutic agents selected from antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

Schemes and Examples

Exemplary, non-limiting, chemical entities and methods useful in preparing compounds of the invention will now be described by reference to illustrative synthetic schemes for their general preparation below and the specific examples that follow. Those skilled in the art will appreciate that other synthetic routes may be used to synthesize the compounds according to the invention. Although specific starting materials and reagents are depicted and discussed herein, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in the reaction schemes is preferably run at a temperature from about 0° ° C. to the reflux temperature of the solvent used. Unless otherwise specified, the variables shown in the schemes below are as defined above in reference to Formula (I).

Compounds according to the invention may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arz-neimittel-Forschung, 40(12):1328-31, (1990), each of which are expressly incorporated by reference. Starting materials are generally available from commercial sources such as Sigma-Aldrich Chemicals (Milwaukee, WI) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Synthetic chemistry transformations and protecting group methodologies (protection and deprotection) useful in synthesizing compounds according to the invention and necessary reagents and intermediates are known in the art and include, for example, those described in R. Larock, Comprehensive Organic Transformations, VCH Publishers (1989); T. W. Greene and P. G.M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof. The need for such protection will vary depending on the nature of the remote functionality and the conditions of the preparation methods. Suitable aminoprotecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art.

Additional particularly useful reactions in preparing compounds of the present invention include alkylation, reductive amination, oxidation, reduction, and hydrolysis reactions. Such transformations are well within the ordinary skill in the art.

Compounds according to the invention may be prepared singly or as compound libraries comprising, for example, at least two, or 5 to 1,000 compounds, or 10 to 100 compounds. Libraries of compounds of the invention may be prepared by a combinatorial "split and mix" approach or by multiple parallel syntheses using either solution phase or solid phase chemistry, by procedures known to those skilled in the art. Thus, according to a further aspect of the invention there is provided a compound library comprising at least two compounds of the invention, or pharmaceutically acceptable salts thereof.

In the methods of preparing compounds according to the invention, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (-) menthyl chloroformate in the presence of base, or Mosher ester, a-methoxy-a-(trifluoromethyl)phenyl acetate of the racemic mixture and analyzing the 1H NMR spectrum for the presence of the two atropisomeric enantiomers or diastereomers (Jacob III. J. Org. Chem. (1982) 47:4165). Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

DETAILED DESCRIPTION OF EXPERIMENTS

Synthetic Method A: Fisher indole synthesis using beta substituted cyclic ketone and 2-carboxylate-phenyl hydrazine followed by esterification gave indole intermediate. Alkylation of indole nitrogen with the required alkyl bromide followed by hydrolysis gave rise to the desired product after purification.

Representative Example: 7-butyl-5-[(3-carbamoylphenyl)methyl]-5H,6H,7H,8H,9H,10H-cyclohepta[b]indole-4-carboxylic acid

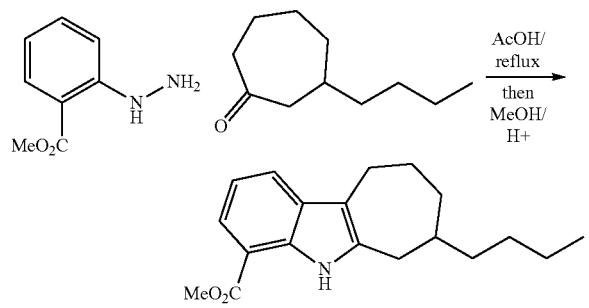

Step 1.1: Hydrazine (1.12g) and ketone(3g) was mixed in AcOH and stirred at 130° C. which after 3 hr, AcOH was distilled off. Reaction was then neutralized with saturated sodium bicarbonate and extracted with EtOAc (300 mL×3) which was dried and concentrated by rotary evaporation. Purification by column chromatography (30% EtOAc:Pet Ether) gave 1 g of desired indole product.
Step 1.2: 1 g of indole was dissolved in 15 mL of MeOH. 1 mL of $H_2SO_4$ was added and heated at 80° C. After 16 hrs, MeOH was distilled off from the reaction mixture, neutralized with saturated sodium bicarbonate and extracted with EtOAc (300 mL×3) which was dried and concentrated by rotary evaporation. Purification by column chromatography (20% EtOAc:Pet Ether) gave 900 mg of desired indole ester product

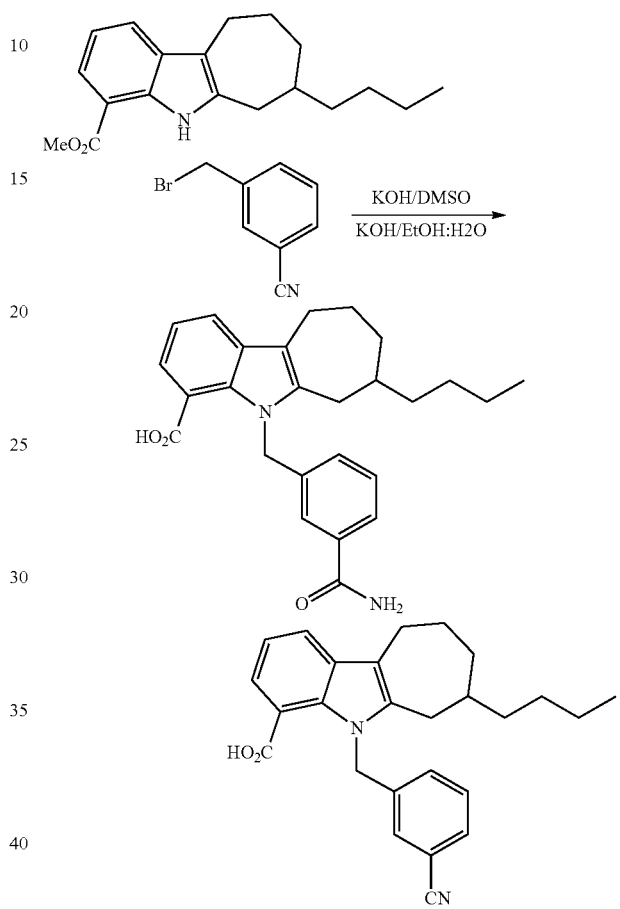

Step 2.1: The indole ester (900 mg) and the 3-Cyano-benzyl bromide(1.18g) was dissolved in DMSO (10 mL) and then KOH(842 mg) was added at room temperature and stirred. After 2 hr, reaction was diluted with water and extracted with EtOAc (300 mL×3) which was dried and concentrated by rotary evaporation. Purification by column chromatography (15% EtOAc:Pet Ether) gave 700 mg of desired indole ester product
Step 2.2: Benzyl indole was dissolved in EtOH:H2O (30:6 mL) and then KOH(473 mg) was added at room temperature and heated to 70° C. After 15 min, reaction was cooled to r.t., neutralized with 1N HCl solution and extracted with EtOAc (300 mL×3). Collected organic extract was then dried and concentrated by rotary evaporation. Purification by MS directed purification gave 110 mg of 7-butyl-5-[(3-cyanophenyl)methyl]-5H,6H,7H,8H,9H,10H-cyclohepta[b]indole-4-carboxylic acid and 105 mg of 7-butyl-5-[(3-carbamoylphenyl)methyl]-5H,6H, 7H, 8H,9H, 10H-cyclohepta[b]indole-4-carboxylic acid.
Synthetic Method B: Fisher indole synthesis using an unsubstituted cyclic ketone and 2-carboxylate-phenyl hydrazine followed by esterification gave indole intermediate. TFAA-DMSO alkylation protocol (Masanori Tayu et al., Org.

Biomol. Chem. (2013) 11 496) with the required nucleophile followed by ester hydrolysis gave rise to the desired product after purification.

Representative Example: 9-[(3-carbamoylphenyl)methyl]-2-pentyl-2,3,4,9-tetrahydro-1H-carbazole-8-carboxylic acid

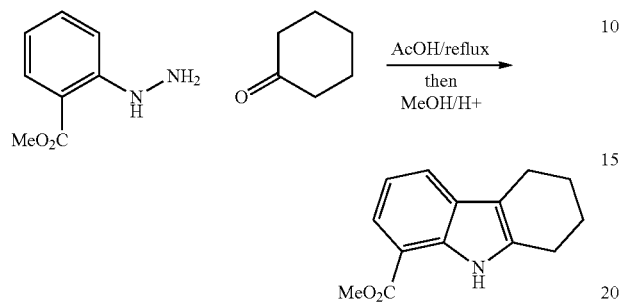

Step 1.1: Hydrazine (6.0 g) and ketone(6.2 g) was mixed in AcOH(100 mL) and stirred at 130° C. which after 3 hr, AcOH was distilled off. Reaction was then neutralized with saturated sodium bicarbonate and extracted with EtOAc (300 mL×3) which was dried and concentrated by rotary evaporation. Purification by column chromatography (30% EtOAc:Pet Ether) gave 5 g of desired indole product.

Step 1.2: 5 g of indole was dissolved in 100 mL of MeOH. 7 mL of concentrated H2SO4 was added and heated at 80° C. After 16 hours, MeOH was distilled off from the reaction mixture, neutralized with saturated sodium bicarbonate and extracted with EtOAc (300 mL×3) which was dried and concentrated by rotary evaporation. Purification by column chromatography (20% EtOAc:Pet Ether) gave 4.2 g of desired indole ester product.

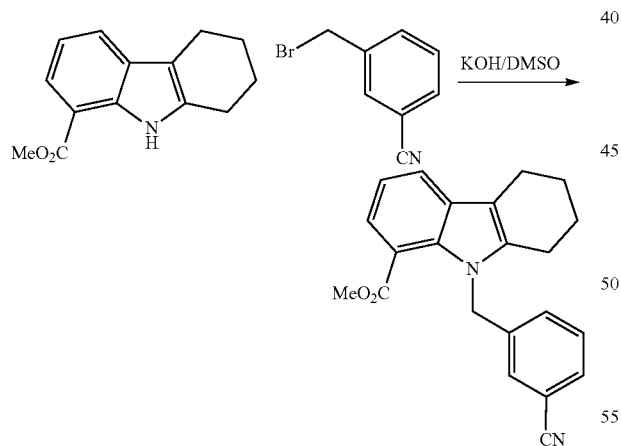

Step 2: The indole ester (3 g) was dissolved in DMSO (50 mL) and then KOH (3.675 g) was added at room temperature. 3-Cyano-benzyl bromide(5.13 g) was then added in portions and stirred. After 2 hr, reaction slowly poured into 1N HCl in flask with ice bath and then the organics were extracted with EtOAc (300 mL×3) which was dried and concentrated by rotary evaporation. Purification by column chromatography (20% EtOAc:Pet Ether) gave 3.5 g of desired indole ester product

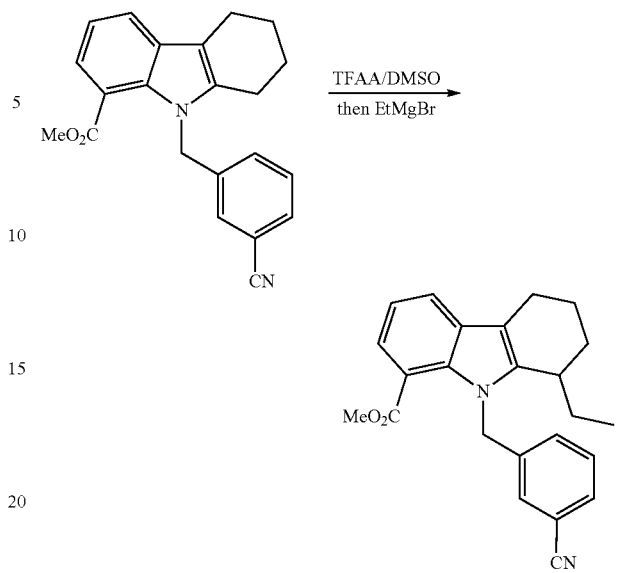

Step 3: To the solution of indole ester (500 mg) in dichloromethane(7 mL) at −40° ° C., was added DMSO (0.315 mL). to this mixture, Trifluoro-acetic anhydride (0.617 mL) was added dropwise and stirred at −40° C. After 1hr, ethyl magnesium bromide (17.647 mL, 1M) was added dropwise to this mixture. After 2 hrs, the reaction was slowly poured into a solution of 10 mL of saturated NaHCO3+20 mL H2O+30 mL of EtOAc. Organic layer was separated and dried and concentrated in vacuo. Purification by column chromatography (20% EtOAc:Pet Ether) gave 300 mg of desired product

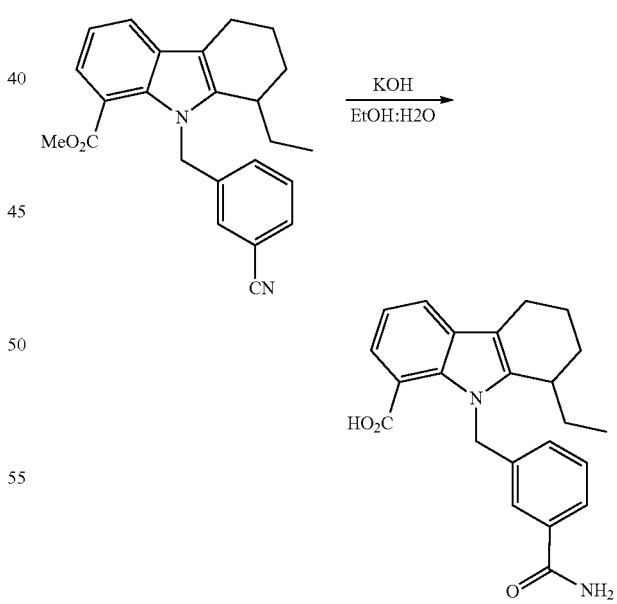

Step 4: Benzyl indole (150 mg) was dissolved in EtOH:H2O (5:2 mL) and then KOH(156 mg) was added at room temperature and stirred. After 16 hrs, reaction neutralized with 1N HCl solution and solid was filtered as 9-[(3-carbamoylphenyl)methyl]-2-pentyl-2,3,4,9-tetrahydro-1H-carbazole-8-carboxylic acid (30 mg).

Antiviral Activity

Activity of compounds affecting viral replication and disease was tested against coronavirus replication in differentiated 3T3-L1 mouse adipocyte cells using human coronavirus OC43 as a model virus. 3T3-L1 preadipocytes (ATCC) were routinely cultured in a growth medium composed of DMEM high-glucose (Sigma), 10% FBS (Gibco), 10 U/ml penicillin and 10 µg/ml streptomycin (P/S; Gibco) in a standard cell culture incubator at 37° C. To induce adipogenic differentiation, a confluent layer of 3T3-L1 cells were incubated with the growth medium containing 2 µM rosiglitazone, 1 µM dexamethasone, 500 µM IBMX, and 1 µg/ml insulin (Sigma). Forty-eight (48) hours later (on day 2) and on days 4 and 6, medium of the cells was replaced with fresh medium containing 1 µg/ml insulin. On days 8 and 10, the medium was refreshed with regular growth medium and addition of insulin was omitted. On day 11 or 12, the cells were infected with human coronavirus OC43 (ATCC) at a multiplicity of 0.05 TCID50 (tissue-culture infectious-dose 50) per cell in DMEM containing 2% heat-inactivated FBS and P/S. One hour after infection, medium of the cells were replaced with fresh medium containing either the indicated FABP4 modulating compounds or the vehicle in which the compounds were dissolved (DMSO). The final compound concentration was 10 UM and final concentration of DMSO was 0.1% (v/v). The cells were incubated at 35° C. during the course of infection and compound treatment. Twenty-four hours after infection, medium of the cells was collected, cleared by centrifugation at 2,000g for 5 minutes, and frozen at −80 degrees C. until further processing. The viral titers in the samples were determined by TCID50 assay in MRC5 cells (ATCC) using Reed-Munch method, and median fold reduction of virus titers in compound treated cells compared to vehicle control was calculated.

Table 1 shown below depicts the antiviral activity of the FABP4 modulating compounds. The compounds were categorized based on the magnitude of their antiviral activity. The compounds reduced virus titers >100-fold, between 10- to 99-fold, and between 2- to 9-fold compared to vehicle control were represented as "A", "B" and "C", respectively.

TABLE 1

| Compound | IUPAC name | Antiviral activity group |
|---|---|---|
| 1 | 7-butyl-5-[(3-carbamoylphenyl)methyl]-5H,6H,7H,8H,9H,10H-cyclohepta[b]indole-4-carboxylic acid | B |
| 2 | 7-butyl-5-[(3-cyanophenyl)methyl]-5H,6H,7H, 8H,9H,10H-cyclohepta[b]indole-4-carboxylic acid | A |
| 3 | 7-butyl-5-[(4-methylphenyl)methyl]-5H,6H,7H,8H,9H,10H-cyclohepta[b]indole-4-carboxylic acid | B |
| 4 | 7-butyl-5-[(2-methylphenyl)methyl]-5H,6H,7H,8H,9H,10H-cyclohepta[b]indole-4-carboxylic acid | A |
| 5 | 5-[(3-carbamoylphenyl)methyl]-7-hexyl-5H,6H,7H,8H,9H,10H-cyclohepta[b]indole-4-carboxylic acid | B |
| 6 | 5-[(3-cyanophenyl)methyl]-7-hexyl-5H,6H,7H,8H,9H,10H-cyclohepta[b]indole-4-carboxylic acid | A |
| 7 | 9-[(3-carbamoylphenyl)methyl]-2-hexyl-2,3,4,9-tetrahydro-1H-carbazole-8-carboxylic acid | B |
| 8 | 9-[(3-cyanophenyl)methyl]-2-hexyl-2,3,4,9-tetrahydro-1H-carbazole-8-carboxylic acid | B |
| 9 | 2-hexyl-9-[(pyridin-3-yl)methyl]-2,3,4,9-tetrahydro-1H-carbazole-8-carboxylic acid | A |
| 10 | 2-hexyl-9-[(2-methylphenyl)methyl]-2,3,4,9-tetrahydro-1H-carbazole-8-carboxylic acid | A |
| 11 | 9-[(2-fluorophenyl)methyl]-2-hexyl-2,3,4,9-tetrahydro-1H-carbazole-8-carboxylic acid | A |
| 12 | 1-butyl-9-[(3-carbamoylphenyl)methyl]-2,3,4,9-tetrahydro-1H-carbazole-8-carboxylic acid | C |
| 13 | 1-butyl-9-[(3-cyanophenyl)methyl]-2,3,4,9-tetrahydro-1H-carbazole-8-carboxylic acid | B |
| 14 | 6-butyl-5-[(3-carbamoylphenyl)methyl]-5H,6H,7H,8H,9H,10H-cyclohepta[b]indole-4-carboxylic acid | B |
| 15 | 6-butyl-5-[(3-cyanophenyl)methyl]-5H,6H,7H,8H,9H,10H-cyclohepta[b]indole-4-carboxylic acid | B |
| 16 | 3-butyl-4-[(3-carbamoylphenyl)methyl]-1H,2H,3H,4H-cyclopenta[b]indole-5-carboxylic acid | C |
| 17 | 2-butyl-4-[(3-carbamoylphenyl)methyl]-1H,2H,3H,4H-cyclopenta[b]indole-5-carboxylic acid | C |
| 18 | 2-butyl-4-[(3-cyanophenyl)methyl]-1H,2H,3H,4H-cyclopenta[b]indole-5-carboxylic acid | C |
| 19 | 10-butyl-5-[(3-carbamoylphenyl)methyl]-5H,6H,7H,8H,9H,10H-cyclohepta[b]indole-4-carboxylic acid | C |
| 20 | 3-butyl-9-[(3-carbamoylphenyl)methyl]-2,3,4,9-tetrahydro-1H-carbazole-8-carboxylic acid | C |
| 21 | 2-((2'-(5-Ethyl-3,4-diphenyl-1H-pyrazol-1-yl)-[1,1'-biphenyl]-3-yl)oxy)acetic acid | C |
| 22 | 6-chloro-4-phenyl-2-(piperidin-1-yl)-3-(1H-tetrazol-5-yl)quinoline | A |
| 23 | 5-((3-chloro-2-methylphenoxy)methyl)-2-phenyl-[1,2,4]triazolo[1,5-a]pyrimidin-7(4H)-one | B |
| 24 | 3-(5-cyclopropyl-3-(3,5-dimethyl-1H-pyrazol-4-yl)-2-(3-isopropoxyphenyl)-1H-indol-1-yl)propanoic acid | B |

Figure 1B:
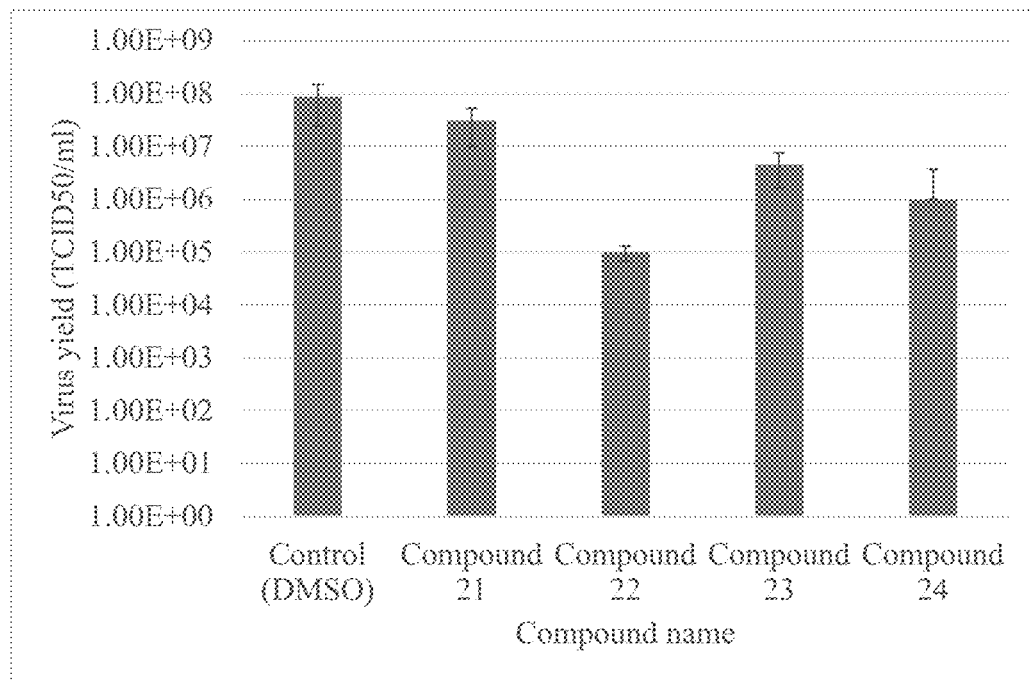
Figure 2:
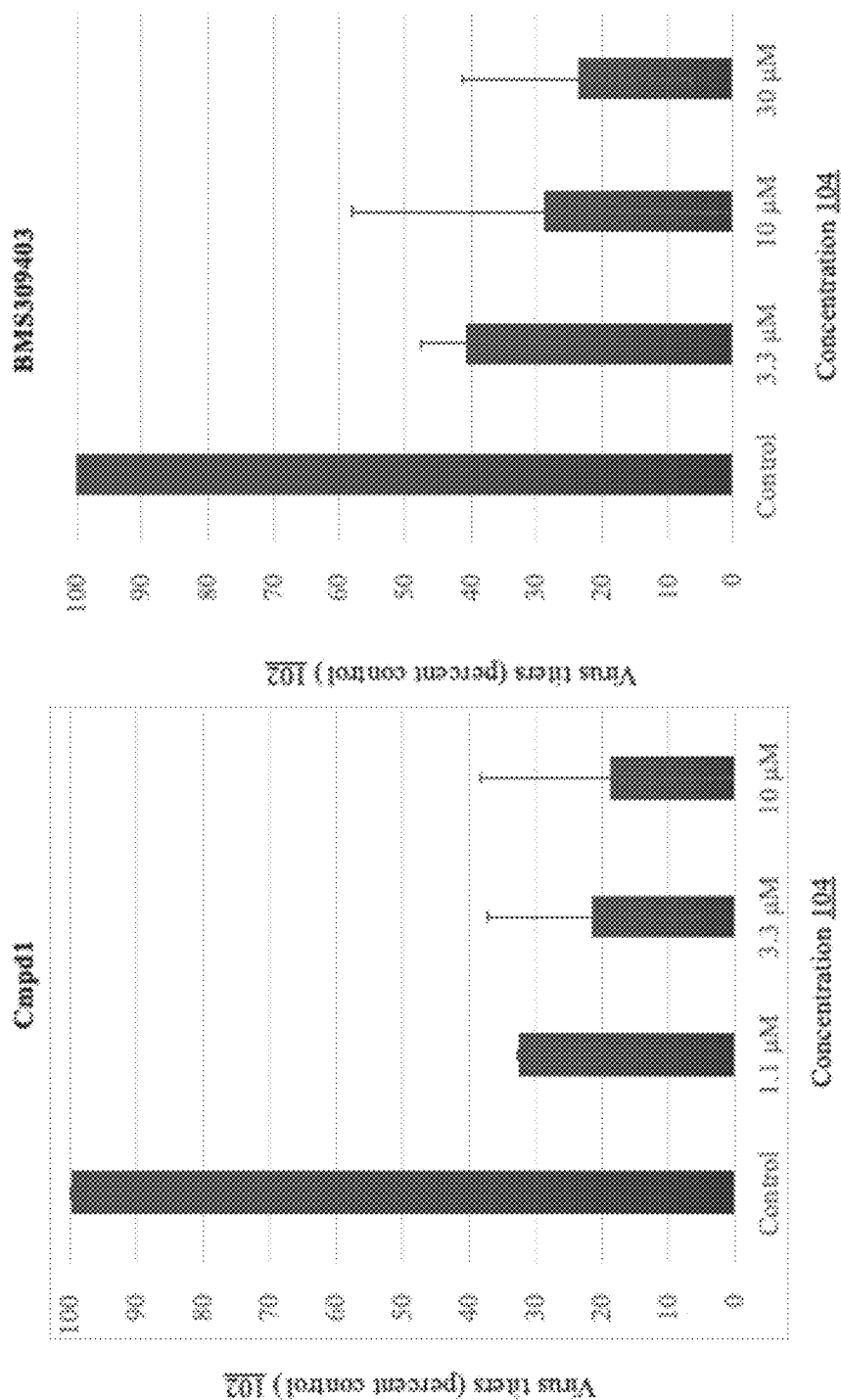

FIG. 1A and FIG. 1B depict graphical charts showing the virus yield obtained from cells 5 treated with the corresponding compounds and vehicle control (DMSO). More specifically, FIG. 1 includes a graph for the vehicle control (DMSO) and different FABP4 modulating compounds and a second graph for the FABP4 modulating compounds 2-((2'-(5-Ethyl-3,4-diphenyl-1H-pyrazol-1-yl)-[1,1'-biphenyl]-3-yl)oxy)acetic acid (Compound 21), referred to as BMS309403 in the art, 6-chloro-4-phenyl-2-(piperidin-1-yl)-3-(1H-tetrazol-5-yl)quinoline (Compound 22), 5-((3-chloro-2-methylphenoxy)methyl)-2-phenyl-[1,2,4]triazolo[1,5-alpyrimidin-7(4H)-one (Compound 23), 3-(5-cyclopropyl-3-(3,5-dimethyl-1H-pyrazol-4-yl)-2-(3-isopropoxyphenyl)-1H-indol-1-yl)propanoic acid (Compound 24) and their corresponding vehicle control. Each of the graphs include an x-axis associated with compound name and a y-axis associated with a viral titer in TCID50/ml. Data are shown as mean (+standard deviation) of two or three biological replicates.

According to one embodiment of the invention, compounds of the invention demonstrate antiviral activity against coronavirus. The subject matter of the present invention is particularly advantageous due to its unexpected results with coronavirus. For example, as described herein, compounds of the invention is particularly efficacious in treating coronavirus.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method for treating a viral disease in a subject comprising administering to said subject a therapeutically effective dose of one or more of the compounds described in Formula (I):

Formula (I)

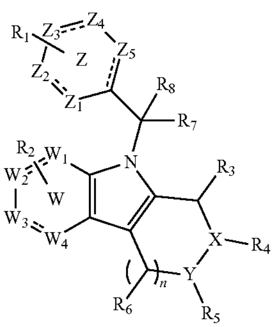

wherein:

$W_{14}$ and $Z_1$-$Z_5$ are each independently —C, —CH, $CH_2$, O, S, or N;

X is independently CH or N;

Y is CH;

n is a number between 0 and 3;

one or more $R^1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, wherein the substituted cycloaryl or cycloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, and $SO_2NH_2$;

one or more $R^2$'s on the ring W are independently selected from the group consisting of: CN, OH, $CHF_2$, $CH_2F$, $CF_3$, COOH, $CONH_2$, $B(OH)_2$, $B(OR)_2$, an acid isostere, a halogen, and a bicyclic heteroaryl;

$R^7$ is hydrogen or CN, COOH, $CONH_2$, $B(OH)_2$, $B(OR)_2$ or an acid isostere;

R is alkyl;

$R^3$, $R^4$, $R^5$ or $R^5$, or $R^6$ is each independently selected from:

(1) hydrogen;

(2) substituted or unsubstituted alkyl or ether having 2 to 12 carbon atoms, (3) a substituted amine, or (4) —$(CH_2)_m$ G, wherein m is 1 to 12 and G is independently selected from:

(a) cycloalkyl containing 3 to 6 carbon atoms, (b) aryl or heteroaryl, (c) $CF_3$, $CF_2H$ or $CFH_2$, or (d) a heterocycle, provided that $R^3$, $R^4$, $R^5$, $R^5$, or $R^5$ are not all hydrogen; and wherein the acid isostere is selected from the group consisting of and 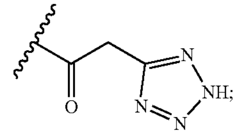 or pharmaceutically acceptable salts or stereoisomers thereof.

2. The method according to claim 1, wherein $R^1$ and $R^2$ are both present and each is independently CN, COOH, or $CONH_2$.

3. The method according to claim 1, wherein the $R_1$ on the ring Z is the CN.

4. The method according to claim 1, wherein the $R^1$ on the ring Z comprise the CN and/or the halogen.

5. The method according to claim 1, wherein each of the one or more compounds are a pure optical isomer.

6. The method according to claim 1 for use in the prophylaxis or treatment of viral disorders by acting on the fatty acid binding protein FABP4.

7. The method according to claim 6, wherein the viral disorders are selected from common cold, SARS, and COVID-19.

8. The method according to claim 1, wherein the one or more compounds are delivered as pharmaceutical compositions.

9. A method for treating a viral disease in a subject comprising administering to said subject a therapeutically effective dose of one or more compounds described in Formula (II):

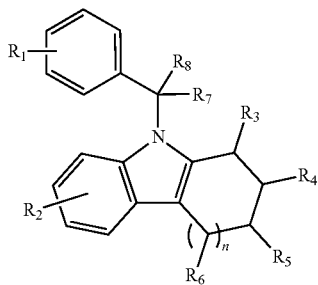

Formula (II)

Wherein:
n=0, 1, or 2;
$R_1$ is selected from the group consisting of: CN, COOH, $CONH_2$, $B(OH)_2$, $B(OR)_2$, an acid isostere, and a halogen;
$R_2$ is selected from the group consisting of: CN, COOH, $CONH_2$, $B(OH)_2$, $B(OR)_2$, an acid isostere, a halogen, and a bicyclic compound;
$R_7$ is hydrogen or CN, COOH, $CONH_2$, $B(OH)_2$, $B(OR)$, or an acid isostere;
R is alkyl;
$R_3$, $R_4$, $R_5$ or $R_8$, or $R_6$ when n is not zero, is each independently selected from:
(1) hydrogen;
(2) alkyl having 1 to 12 carbon atoms, or
(3) —$(CH_2)_mG$, wherein m is 1 to 12 and G is independently selected from:
(a) cycloalkyl containing 3 to 6 carbon atoms,
(b) aryl or heteroaryl, or
(c) $CF_3$, $CF_2H$ or $CFH_2$;
provided that G is not a nitrogen or oxygen-containing group; and
provided that $R^3$, $R^4$, $R^5$, $R_1$, or $R_2$ are not all hydrogen; or pharmaceutically acceptable salts thereof.

10. The method according to claim 9, wherein $R^1$ and $R^2$ are both present, and each is independently CN, COOH, or $CONH_2$.

11. The method according to claim 9, wherein each of the one or more compounds are a pure optical isomer.

12. The method according to claim 9 for use in the prophylaxis or treatment of viral disorders by acting on the fatty acid binding protein FABP4.

13. The method according to claim 12, wherein the viral disorders are selected from common cold, SARS, and COVID-19.

14. The method according to claim 9, wherein the one or more compounds are delivered as pharmaceutical compositions.

15. A method for treating a viral disease in a subject comprising administering to said subject a therapeutically effective dose of one or more of the compounds described in Formula (III):

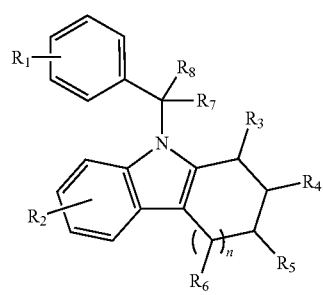

Formula (III)

Wherein:
n=0, 1, or 2;
$R_1$ and $R_2$ are each independently halogen, alkyl, cycloalkyl, aryl, heteroaryl, CN, COOH, $CONH_2$, $B(OH)_2$, $B(OR)_2$, or an acid isostere;
$R_7$ is hydrogen, alkyl, cycloalkyl, aryl, heteroaryl, CN, COOH, $CONH_2$, $B(OH)_2$, $B(OR)_2$ or an acid isostere;
R is alkyl;
$R_3$, $R_4$, $R_5$ or $R_8$, or $R_6$ when n is not zero, are each independently selected from:
(1) hydrogen;
(2) alkyl having 1 to 12 carbon atoms, or
(3) —$(CH_2)_mG$, wherein m is 1 to 12 and G is independently selected from:
(a) cycloalkyl containing 3 to 6 carbon atoms;
(b) aryl or heteroaryl; or
(c) $CF_3$, $CF_2H$, or $CFH_2$;
provided that $R^3$, $R^4$, $R^5$, $R^5$, or $R^5$ are not all hydrogen;
or pharmaceutically acceptable salts or stereoisomers thereof.

16. The method according to claim 15, wherein each of the one or more compounds are a pure optical isomer.

17. The method according to claim 15 for use in the prophylaxis or treatment of viral disorders by acting on the fatty acid binding protein FABP4.

18. The method according to claim 17, wherein the viral disorders are selected from common cold, SARS, and COVID-19.

19. The method according to claim 15, wherein the one or more compounds are delivered as pharmaceutical compositions.

20. A method for treating a viral disease in a subject comprising administering to said subject a therapeutically effective dose of one or more of the of compounds described in Formula (IV):

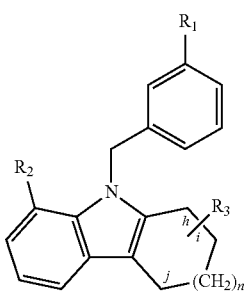

Formula (IV)

Wherein:

n=0, 1 or 2;

$R_1$ and $R_2$ are each independently CN, COOH or $CONH_2$;

$R_3$ is independently selected from:
- (1) alkyl having 1 to 12 carbon atoms;
- (2) $-(CH_2)_m G$, wherein m is 1 to 12 and G is independently selected from:
  - (a) cycloalkyl containing 3 to 6 carbon atoms;
  - (b) phenyl; and
  - provided that G is not a nitrogen or oxygen-containing group;

or pharmaceutically acceptable salts thereof.

21. The method according to claim 20, wherein: n=2 and $R^3$ is attached to the h-, i- or j-position.

22. The method according to claim 20, wherein each of the one or more compounds are a pure optical isomer.

23. The method according to claim 20 for use in the prophylaxis or treatment of viral disorders by acting on the fatty acid binding protein FABP4.

24. The method according to claim 23, wherein the viral disorders are selected from common cold, SARS, and COVID-19.

25. The method according to claim 20, wherein the one or more compounds are delivered as pharmaceutical compositions.

26. A method for treating a viral disease in a subject comprising administering to said subject a therapeutically effective dose of one or more of the compounds selected from the group consisting of:

5-[(3-cyanophenyl)methyl]-2-fluoro-7-hexyl-5H,6H,7H,8H,9H,10H-cyclohepta[b]indole-4-carboxylic acid, 5-[(6-cyanopyridin-2-yl)methyl]-7-hexyl-5H,6H,7H,8H,9H,10H-cyclohepta[b]indole-4-carboxylic acid, 5-[(6-carbamoylpyridin-2-yl)methyl]-7-hexyl-5H,6H,7H,8H,9H,10H-cyclohepta[b]indole-4-carboxylic acid, 6-({4-carboxy-7-hexyl-5H,6H,7H,8H,9H,10H-cyclohepta[b]indol-5-yl}methyl)pyridine-2-carboxylic acid, 5-[(3-cyano-2-fluorophenyl)methyl]-7-hexyl-5H,6H,7H,8H,9H,10H-cyclohepta[b]indole-4-carboxylic acid, 5-[(1,3-benzoxazol-6-yl)methyl]-7-hexyl-5H,6H,7H,8H,9H,10H-cyclohepta[b]indole-4-carboxylic acid, 5-[(1,3-benzoxazol-5-yl)methyl]-7-hexyl-5H,6H,7H,8H,9H,10H-cyclohepta[b]indole-4-carboxylic acid, 5-[(6-fluoropyridin-2-yl)methyl]-7-hexyl-5H,6H,7H,8H,9H,10H-cyclohepta[b]indole-4-carboxylic acid, 5-[(2-fluoropyridin-4-yl)methyl]-7-hexyl-5H,6H,7H,8H,9H,10H-cyclohepta[b]indole-4-carboxylic acid, 7-hexyl-5-{[6-(trifluoromethyl)pyridin-2-yl]methyl}-5H,6H,7H,8H,9H,10H-cyclohepta[b]indole-4-carboxylic acid, 7-hexyl-5-{[2-(trifluoromethyl)pyridin-4-yl]methyl}-5H,6H,7H,8H,9H,10H-cyclohepta[b]indole-4-carboxylic acid, 5-[(5-cyanopyridin-3-yl)methyl]-7-hexyl-5H,6H,7H,8H,9H,10H-cyclohepta[b]indole-4-carboxylic acid, 5-[(5-cyanothiophen-2-yl)methyl]-7-hexyl-5H,6H,7H,8H,9H,10H-cyclohepta[b]indole-4-carboxylic acid, 5-[(4-cyanothiophen-2-yl)methyl]-7-hexyl-5H,6H,7H,8H,9H,10H-cyclohepta[b]indole-4-carboxylic acid, 5-[(5-cyanofuran-2-yl)methyl]-7-hexyl-5H,6H,7H,8H,9H,10H-cyclohepta[b]indole-4-carboxylic acid, 5-[(3,5-dimethyl-1,2-oxazol-4-yl)methyl]-7-hexyl-5H,6H,7H,8H,9H,10H-cyclohepta[b]indole-4-carboxylic acid, 5-(3-cyanobenzoyl)-7-hexyl-5H,6H,7H,8H,9H,10H-cyclohepta[b]indole-4-carboxylic acid, 5-[(1,3-benzoxazol-7-yl)methyl]-7-hexyl-5H,6H,7H,8H,9H,10H-cyclohepta[b]indole-4-carboxylic acid, 5-[(5-cyanothiophen-3-yl)methyl]-7-hexyl-5H,6H,7H,8H,9H,10H-cyclohepta[b]indole-4-carboxylic acid, 7-hexyl-5-[(1H-indol-4-yl)methyl]-5H,6H,7H,8H,9H,10H-cyclohepta[b]indole-4-carboxylic acid, 5-[(3-carbamoylphenyl)methyl]-7-propyl-5H,6H,7H,8H,9H,10H-cyclohepta[b]indole-4-carboxylic acid, 7-butyl-5-[(3-carbamoylphenyl)methyl]-5H,6H,7H,8H,9H,10H-cyclohepta[b]indole-4-carboxylic acid, 7-butyl-5-[(3-cyanophenyl)methyl]-5H,6H,7H,8H,9H,10H-cyclohepta[b]indole-4-carboxylic acid, 7-butyl-5-[(pyridin-3-yl)methyl]-5H,6H,7H,8H,9H,10H-cyclohepta[b]indole-4-carboxylic acid, 7-butyl-5-[(3-methylphenyl)methyl]-5H,6H,7H,8H,9H,10H-cyclohepta[b]indole-4-carboxylic acid, 7-butyl-5-[(3-methoxyphenyl)methyl]-5H,6H,7H,8H,9H,10H-cyclohepta[b]indole-4-carboxylic acid, 7-butyl-5-[(3-chlorophenyl)methyl]-5H,6H,7H,8H,9H,10H-cyclohepta[b]indole-4-carboxylic acid, 7-butyl-5-[(3-hydroxyphenyl)methyl]-5H,6H,7H,8H,9H,10H-cyclohepta[b]indole-4-carboxylic acid, 7-butyl-5-[(2-methoxypyridin-4-yl)methyl]-5H,6H,7H,8H,9H,10H-cyclohepta[b]indole-4-carboxylic acid, 7-butyl-5-[(4-carbamoylphenyl)methyl]-5H,6H,7H,8H,9H,10H-cyclohepta[b]indole-4-carboxylic acid, 7-butyl-5-[(2-carbamoylphenyl)methyl]-5H,6H,7H,8H,9H,10H-cyclohepta[b]indole-4-carboxylic acid, 7-butyl-5-[(4-methylphenyl)methyl]-5H,6H,7H,8H,9H,10H-cyclohepta[b]indole-4-carboxylic acid, 7-butyl-5-[(2-cyanophenyl)methyl]-5H,6H,7H,8H,9H,10H-cyclohepta[b]indole-4-carboxylic acid, 7-butyl-5-[(2-methylphenyl)methyl]-5H,6H,7H,8H,9H,10H-cyclohepta[b]indole-4-carboxylic acid, 7-butyl-5-[(2-fluorophenyl)methyl]-5H,6H,7H,8H,9H,10H-cyclohepta[b]indole-4-carboxylic acid, 5-[(3-carbamoylphenyl)methyl]-7-pentyl-5H,6H,7H,8H,9H,10H-cyclohepta[b]indole-4-carboxylic acid, 5-[(3-cyanophenyl)methyl]-7-pentyl-5H,6H,7H,8H,9H,10H-cyclohepta[b]indole-4-carboxylic acid, 5-[(3-carbamoylphenyl)methyl]-7-(2-phenylethyl)-5H,6H,7H,8H,9H,10H-cyclohepta[b]indole-4-carboxylic acid, 5-[(3-cyanophenyl)methyl]-7-(2-phenylethyl)-5H,6H,7H,8H,9H,10H-cyclohepta[b]indole-4-carboxylic acid, 5-[(3-carbamoylphenyl)methyl]-7-hexyl-5H,6H,7H,8H,9H,10H-cyclohepta[b]indole-4-carboxylic acid, 5-[(3-cyanophenyl)methyl]-7-hexyl-5H,6H,7H,8H,9H,10H-cyclohepta[b]indole-4-carboxylic acid, 5-[(3-carbamoylphenyl)methyl]-7-octyl-5H,6H,7H,8H,9H,10H-cyclohepta[b]indole-4-carboxylic acid, 5-[(3-cyanophenyl)methyl]-7-octyl-5H,6H,7H,8H,9H,10H-cyclohepta[b]indole-4-carboxylic acid, 5-[(3-fluorophenyl)methyl]-7-hexyl-5H,6H,7H,8H,9H,10H-cyclohepta[b]indole-4-carboxylic acid, 7-hexyl-5-[(pyridin-3-yl)methyl]-5H,6H,7H,8H,9H,10H-cyclohepta[b]indole-4-carboxylic acid, 7-hexyl-5-[(3-methylphenyl)methyl]-5H,6H,7H,8H,9H,10H- cyclohepta[b]indole-4-carboxylic acid, 7-hexyl-5-[(3-methoxyphenyl)methyl]-5H,6H,7H,8H,9H,10H-cyclohepta[b]indole-4-carboxylic acid, 5-[(3-chlorophenyl)methyl]-7-hexyl-5H,6H,7H,8H,9H,10H-cyclohepta[b]indole-4-carboxylic acid, 7-hexyl-5-[(2-methoxypyridin-4-yl)methyl]-5H,6H,7H,8H,9H,10H-cyclohepta[b]indole-4-carboxylic acid, 5-[(3-carboxyphenyl)methyl]-7-hexyl-5H,6H,7H,8H,9H,10H-cyclohepta[b]indole-4-carboxylic acid, 5-[(4-carbamoylphenyl)methyl]-7-hexyl-5H,6H,7H,8H,9H,10H-cyclohepta[b]indole-4-carboxylic acid, 5-[(2-carbamoylphenyl)methyl]-7-hexyl-5H,6H,7H,8H,9H,10H-cyclohepta[b]indole-4-carboxylic acid, 7-hexyl-5-[(4-methylphenyl)methyl]-5H,6H,7H,8H,9H,10H-cyclohepta[b]indole-4-carboxylic acid, 5-[(4-cyanophenyl)methyl]-7-hexyl-5H,6H,7H,8H,9H,10H-cyclohepta[b]indole-4-carboxylic acid, 5-[(2-cyanophenyl)methyl]-7-hexyl-5H,6H,7H,8H,9H,10H-cyclohepta[b]indole-4-carboxylic acid, 7-hexyl-5-[(2-methylphenyl)methyl]-5H,6H,7H,8H,9H,10H-cyclohepta[b]indole-4-carboxylic acid, 5-[(2-fluorophenyl)methyl]-7-hexyl-5H,6H,7H,8H,9H,10H-cyclohepta[b]indole-4-carboxylic acid, 5-[(4-fluorophenyl)methyl]-7-hexyl-5H,6H,7H,8H,9H,10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H,10H-cyclohepta[b]indole-4-carboxylic acid, 6-butyl-5-[(3-cyanophenyl)methyl]-5H,6H,7H,8H,9H,10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3-ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H,10H-cyclohepta[b]indole-4-carboxylic acid, 5-[(3-cyanophenyl)methyl]-10-ethyl-5H,6H,7H,8H,9H,10H-cyclohepta[b]indole-4-carboxylic acid, 5-[(3-carbamoylphenyl)methyl]-10-propyl-5H,6H,7H,8H,9H,10H-cyclohepta[b]indole-4-carboxylic acid, 5-[(3-cyanophenyl)methyl]-10-propyl-5H,6H,7H,8H,9H,10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H,10H-cyclohepta[b]indole-4-carboxylic acid, 10-butyl-5-[(3-cyanophenyl)methyl]-5H,6H,7H,8H,9H,10H-cyclohepta[b]indole-4-carboxylic acid, 5-[(3-carbamoylphenyl)methyl]-10-pentyl-5H,6H,7H,8H,9H,10H-cyclohepta[b]indole-4-carboxylic acid, 5-[(3-cyanophenyl)methyl]-10-pentyl-5H,6H,7H,8H,9H, 10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3-carbamoylphenyl)methyl]-7-ethyl-5H,6H,7H,8H,9H,10H-cyclohepta[b]indole-4-carboxylic acid, 5-[(3-cyanophenyl)methyl]-7-ethyl-5H,6H,7H,8H,9H,10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H,10H-cyclohepta[b]indol-4-yl} formamido)acetic acid, 2-({7-butyl-5-[(3-cyanophenyl)methyl]-5H,6H,7H,8H,9H,10H-cyclohepta[b]indol-4-yl} formamido)acetic acid, 7-butyl-5-[(3-carbamoylphenyl)methyl]-N-(2-hydroxyethyl)-5H,6H,7H,8H,9H,10H-cyclohepta[b]indole-4-carboxamide, 7-butyl-5-[(3-cyanophenyl)methyl]—N-(2-hydroxyethyl)-5H,6H,7H,8H,9H,10H-cyclohepta[b]indole-4-carboxamide, 7-butyl-5-[(3-fluorophenyl)methyl]-5H,6H,7H,8H,9H,10H-cyclohepta[b]indole-4-carboxylic acid, and 7-butyl-5-[(3-carboxyphenyl)methyl]-5H,6H,7H,8H,9H,10H-cyclohepta[b]indole-4-carboxylic acid, or pharmaceutically acceptable salts or stereoisomers thereof.

27. The method according to claim 26, wherein each of the one or more compounds are a pure optical isomer.

28. The method according to claim 26 for use in the prophylaxis or treatment of viral disorders by acting on the fatty acid binding protein FABP4.

29. The method according to claim 28, wherein the viral disorders are selected from common cold, SARS, and COVID-19.

30. The method according to claim 26, wherein the one or more compounds are delivered as pharmaceutical compositions.

31. A method for treating a viral disease in a subject comprising administering to said subject a therapeutically effective dose of one or more of the compounds described in Formula (I):

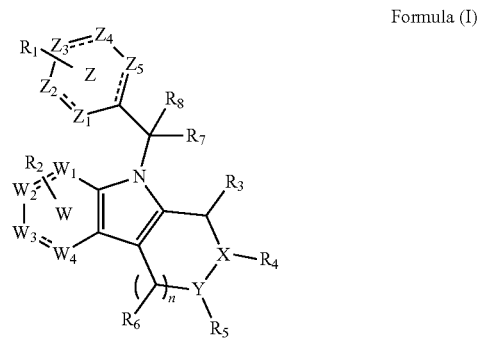

Formula (I)

wherein:

$W_{14}$ and $Z_1$-$Z$, are each independently —C, —CH, $CH_2$, O, S, or N;

X is independently CH or N;

Y is CH;

n is a number between 0 and 3;

one or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, wherein the substituted cycloaryl or cycloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, and $SO_2NH_2$, wherein the halogen is not fluorine;

one or more $R_2$'s on the ring W are independently selected from the group consisting of: CN, OH, $CHF_2$, $CH_2F$, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, B(OR), or an acid isostere;

R is alkyl;

$R_3$, $R_4$, $R_5$ or $R_8$, or $R_6$ is each independently selected from:

(1) hydrogen;

(2) alkyl or ether having 1 to 12 carbon atoms, (3) a substituted amine, or (4) —$(CH_2)_m$ G, wherein m is 1 to 12 and G is independently selected from:

(a) cycloalkyl containing 3 to 6 carbon atoms, (b) aryl or heteroaryl, (c) $CF_3$, $CF_2H$ or $CFH_2$, or (d) a heterocycle, provided that $R^3$, $R^4$, $R^5$, $R^5$, or $R^5$ are not all hydrogen; and wherein the acid isostere is selected from the group consisting of

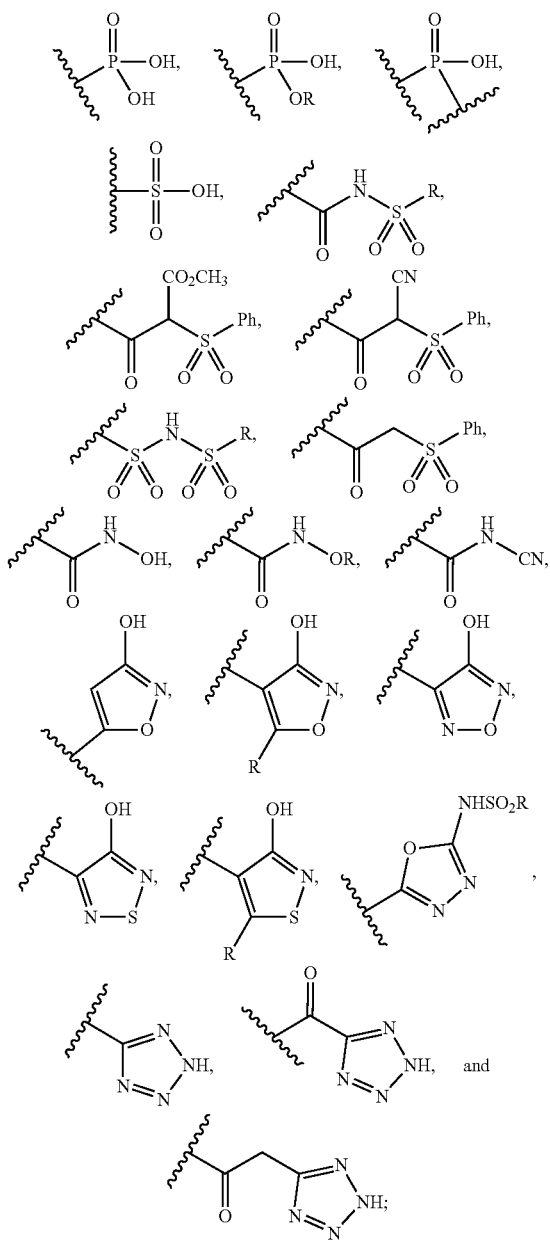

or pharmaceutically acceptable salts or stereoisomers thereof.

32. The method according to claim 1, wherein the Formula I includes more than one $R^1$, and more than one $R^2$.

33. The method according to claim 1, wherein $R^3$, $R^4$, $R^5$, $R^8$, or $R^6$ when n is not zero, is each independently alkyl having 4 carbon atoms.

34. The method according to claim 1, wherein $R^3$, $R^4$, $R^5$, $R^8$, or $R^6$ when n is not zero, is each independently alkyl having 5 carbon atoms.

35. The method according to claim 1, wherein $R^3$, $R^4$, $R^5$, $R^8$, or $R^6$ when n is not zero, is each independently alkyl having 6 carbon atoms.

36. The method according to claim 1, wherein the $R^1$ on the ring Z is the halogen.

37. The method according to claim 1, wherein the $R^1$ on the ring Z is the $CF_3$.

38. The method according to claim 1, wherein the $R^2$ on the ring W is the halogen.

39. The method according to claim 1, wherein the $R^1$ on the ring Z is the CN and/or the halogen, and wherein the $R^2$ on the ring W is another halogen.

40. The method according to claim 39, wherein the halogen is identical to the other halogen.

41. The method according to claim 39, wherein the halogen differs from the other halogen.

42. The method according to claim 9, wherein the Formula II includes more than one $R^1$, and more than one $R^2$.

43. The method according to claim 9, wherein $R^3$, $R^4$, $R^5$, $R^8$, or $R^6$ when n is not zero, is each independently alkyl having 4 carbon atoms.

44. The method according to claim 9, wherein $R^3$, $R^4$, $R^5$, $R^8$, or $R^6$ when n is not zero, is each independently alkyl having 5 carbon atoms.

45. The method according to claim 9, wherein $R^3$, $R^4$, $R^5$, $R^8$, or $R^6$ when n is not zero, is each independently alkyl having 6 carbon atoms.

46. The method according to claim 15, wherein $R^3$, $R^4$, $R^5$, $R^8$, or $R^6$ when n is not zero, is each independently alkyl having 4 carbon atoms.

47. The method according to claim 15, wherein $R^3$, $R^4$, $R^5$, $R^8$, or $R^6$ when n is not zero, is each independently alkyl having 5 carbon atoms.

48. The method according to claim 15, wherein $R^3$, $R^4$, $R^5$, $R^8$, or $R^6$ when n is not zero, is each independently alkyl having 6 carbon atoms.

49. The method according to claim 20, wherein n=0, $R^3$ is attached to the h-, i- or j- position.

50. The method according to claim 20, wherein n=1, $R^3$ is attached to the h-, i- or j- position.

* * * * *